(12) United States Patent
Stuiver et al.

(10) Patent No.: US 6,864,076 B2
(45) Date of Patent: *Mar. 8, 2005

(54) ANTIFUNGAL PROTEINS, DNA CODING THEREFORE, AND HOSTS INCORPORATING SAME

(75) Inventors: Maarten Hendrik Stuiver, Oegstgeest (NL); Jerome Hubertus Henricus Victor Custers, Leiden (NL); Marianne Beatrix Sela-Buurlage, Kefar Bilu (IL); Leo Sjoerd Melchers, Leiden (NL); Wessel Lageweg, Monnickendam (NL); Anne Silene Ponstein, Leiden (NL); Johanna Pieternella Els Van Deventer-Troost, Delft (NL)

(73) Assignee: Syngenta Mogen B.V., Leiden (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

(21) Appl. No.: 09/258,031

(22) Filed: Feb. 25, 1999

(65) Prior Publication Data

US 2002/0168735 A1 Nov. 14, 2002

Related U.S. Application Data

(63) Continuation of application No. PCT/EP97/04923, filed on Sep. 4, 1997.

(51) Int. Cl.[7] .............................. C12N 9/04; C07H 21/04
(52) U.S. Cl. ....................... 435/190; 435/91.4; 435/183; 435/25; 800/279; 530/350; 536/23.1; 536/23.2; 536/23.6
(58) Field of Search ............................. 435/190, 91.4, 435/183, 25; 424/94.4; 800/279

(56) References Cited

FOREIGN PATENT DOCUMENTS

| WO | 9514784 | 6/1995 |
|---|---|---|
| WO | 9521924 | 8/1995 |
| WO | 9521929 | 8/1995 |
| WO | WO 96/40935 | * 12/1996 |

OTHER PUBLICATIONS

Hu et al. Cloning and expression of a PR5–like from Arabidopsis: Inhibition of fungal growth by bacterially expressed protein, Plant Molecular Biology 34: 949–957, Aug. 1997.*

Woloshuk et al., Pathogen–Induced Proteins with Inhibitory Activity toward Phytophthora infestans, The Plant Cell 3: 619–628, Jun. 1991.*

Wu, G., et al.: "Disease Resistance Conferred by . . . in Transgenic Potato Plants" The Plant Cell, vol. 7, Oct. 1995,pp. 1357–1368, XP002065951.

Krivitzky, M. et al.: "The Arabidopsis Thaliana Transcribed Genome: The GDR CDNA Program" EMBL Sequence Data Library, Heidelberg, Germany, XP002025476: Accession No.: F19886, Mar. 1996.

Kay Kwang–AE Kim et al: "Glucose Oxidase as the Antifungal Principle of . . . Flavus" Canadian Journal of Microbiology: vol. 36, No. 11, Nov. 1990, pp. 760–764, XP000602906.

Dittrich, H. and Kutchan, T.M.: Molecular Cloning, Expression, and Induction of . . . of the , PNAS, vol. 88, Nov. 1991, pp. 9969–9973, XP002025475.

* cited by examiner

Primary Examiner—Richard Hutson
(74) Attorney, Agent, or Firm—Ladas & Parry

(57) ABSTRACT

The present invention provides an isolated protein obtainable from a plant source which has antifungal activity, specifically anti-Phytophthora activity and/or anti-Pythium activity and a molecular weight of about 55–65 kDa as judged by SDS PAGE-electrophoresis, an isolated DNA sequence comprising an open reading frame capable of encoding a protein according to the invention, preferably characterized in that it comprises an open reading frame which is capable of encoding a protein depicted in SEQ ID NO. 16, SEQ ID NO. 57, SEQ ID NO. 70, SEQ ID NO. 72 or SEQ ID NO. 74 or muteins thereof, and DNA capable of hybridizing therewith under stringent conditions. The invention further comprises plants incorporating chimeric DNA capable of encoding a protein according to the invention, and wherein the protein is expressed. Also shown is the carbohydrate and preferably hexose oxidating activity of said protein. Also methods are provided for combating fungi, especially Phytophthora and Pythium species, using a protein or a host cell capable of producing the protein.

6 Claims, 12 Drawing Sheets

RIGHT

LEFT

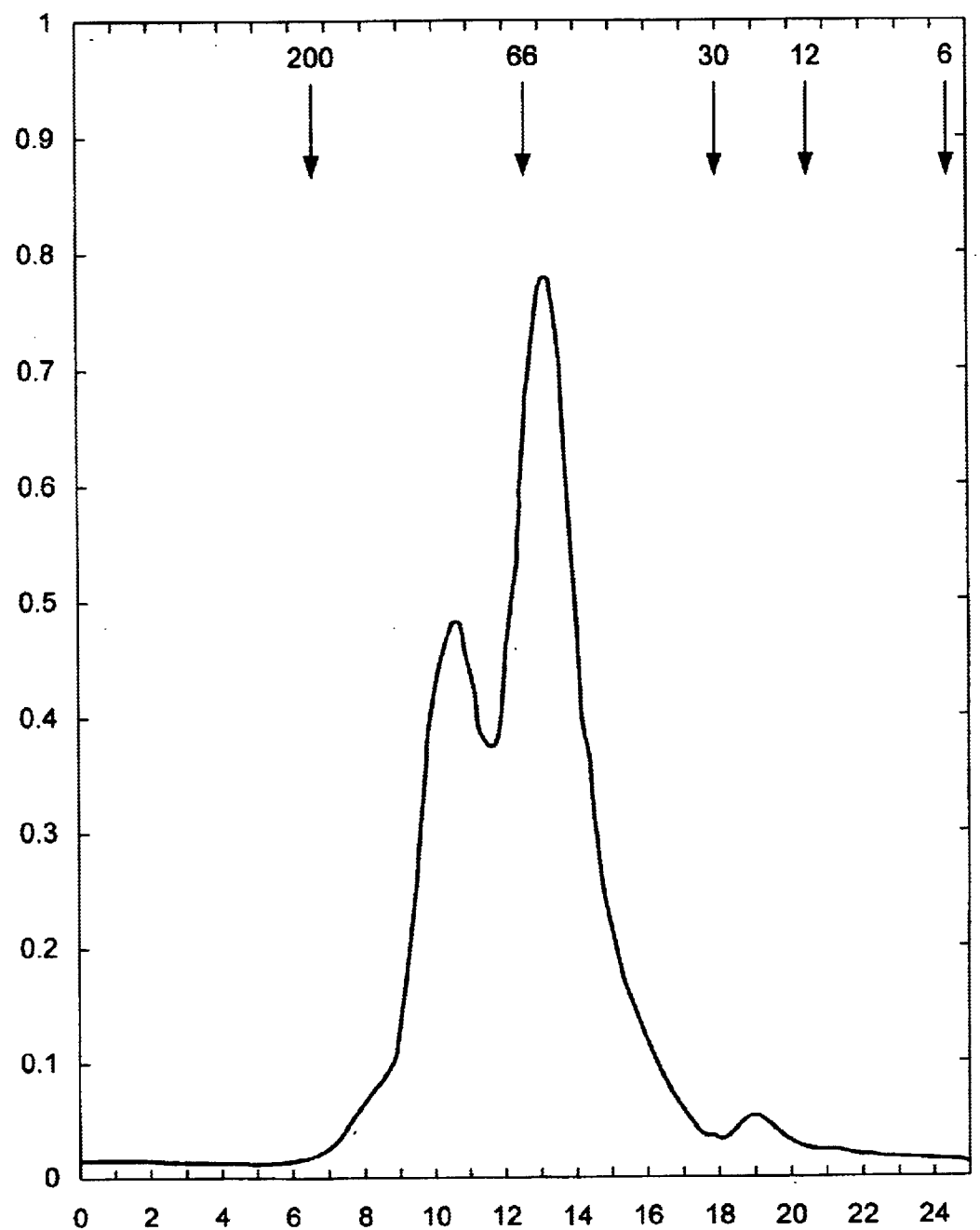
F I G. 6A

```
MS59    1   --------MQTSILTLLLLLSTQSSATGRSITD-RFIQCHDRADPSFP
WL64    1   MAITYSFNFKSYIFPLLLVLLSTHSSATSTSIID-RITQCLNMRADPSFP
At26    1   ------------------------TSRRNSE-TPTQCITSHSDDKHP
At27    1   ---------------------SIQD-QFINCYXRNTHVSID
EcBBE   1   ------MEHKTPIFFSLSIFLSLLNCALGG--ND--LLSCLTFNGVRNH-
PsBBE   1   -----MMCRSLTLRFFLFIVL-LQTCVRGGDVNDNLLSSCLNSHGVHNE-

MS59    42  ITGEVYTPGN--SSFPTVLQNYIRNLRFNETTTPKPFLIITAEHVSHIQA
WL64    50  LSGQLYTDDN--SSFPSVLQAYIRNLRFNESTPKPILIITALHPSHIQA
At26    23  ISPAIFFSQN--GSYSSVLQANIRNLRFNTTSTPKPFLIIAATHESHVQA
At27    20  LEKTLFTDAKNVSLFNQVIESTAQNLQELAKSMRKPGFHFRPIHQSQVQA
EcBBE   40  --TVFSADSD--SDFNRFCHLSHQNPLEQNSLISKPSAILLPGSKEELSN
PsBBE   44  --TTLSTDTN--SDYFKLLEASMQHPLEAKPTVSKPSFIVMPGSKEELSS

MS59    90  AVVCGKQNRLLLKTRSGGHDYEGLSYLTNTNQPFFIVDHFNLRSINVDIE
WL64    98  AVVCAKTHRLLMKTRSGGHDYEGLSYVTNSNQPFFVVDHFNLRSVDVDVA
At26    71  AITCGKRKNLQMKIRSGGHDYDGLSYVTYSGKPFFVLDHFNLRSVDVDVA
At27    70  SIICSKKLGIHFRVRSGGHDFEALSYVSRIEKPFILLDLSKLKQINVDIE
EcBBE   86  TIRCIRKGSWTIRLRSGGHSYEGLSYTSDT--PFILIDLMNLNRVSIDLE
PsBBE   90  TVHCCTRESWTIRLRSGGHSYEGLSYTADT--PFVIVDMMHLWRISIDVL

MS59    140 QETAWVQAGATLGEVYYRIAEKSNKHGFPAGVCPTVGVGHFSGGGYGNL
WL64    148 DETAWVQAGATLGEVYYRIAEKSNSHAFPAGVCPTVGVGHFSGGGYGNL
At26    121 SKTAWVQTGAILGEVYYYIMEKSKTLAYPAGICPTVGVGHISGGGYGNM
At27    120 SNEAWVQPGATLGELYYRIAEKSKIHGFPAGLCTBVCISGYMFGGGYGTL
EcBBE   134 SETAWVESGSTLGELYYALFESSSKLGFTAGWCPTVGTGHISGGGFGNK
PsBBE   138 SETAWVESGATLGELYYAKAQSTDTLGFTAGWCPTVGSSGHISGGGFGNM

MS59    190 MRKYGLSVDNIVDAQIIDVNGKLLDRKSMGEDLFWAITGGGGVSFGVVLA
WL64    198 MGKYGLSVDNIVDAQLIDVNGKLLNRKSMGEDLFWAITGGGGVSFGVVTA
At26    171 MRKYGLTVDNTIDARMVDVNCKILDRELMGEDLYWAINGCGGGSYGVVLA
At27    170 MRKYGLAGDNVLDVKMVDANGKLLDRAAMGEDLFWAIRGGGGASFGIVLA
EcBBE   184 SRKYGLAADNVVDAILIDANGAILDRQAMGEDVFWAIRGGGGVNGAIYA
PsBBE   188 SRKYGLAADNVVDAILIDSNGAILDRSKMGPDVFWAIRGGGGVNGAIYA

MS59    240 YKIKLVRVPEYJTVFTIERREEQNLS-TIAERMVQVADKLDRDLFLRNTF
WL64    248 YKIKLVRVPTTVTVFNVQRTSEQNLS-TIAHRMIQVADKLDMDLFLRNKF
At26    221 YKINLVEVPENVTVFRISRTLEQNAT-DIIHRMQQVAPKLPDELFIRTVI
At27    220 WKIKLVPVPKTVTVFTVTKTLEQDARLKTISKMQQISSRIIELIHIRVVL
EcBBE   234 WKIKLLPVPEKVTVFRVTKNVAIDEATSLLHKMQTVAELLEDF----TL
PsBBE   238 WKIKLLPVPEKLTVFRVTKNVGIEDASSLLHKMQYVADSLDEDF----TV

MS59    289 SVINDTNG-GKTVRAIFPTLYLGNSRNLVTLLNKDFPELGLQESDCTEMS
WL64    297 NVINNTNG-EKTIRGLFPTLYLGNSTALVALLHKDFPELGVEISDCIEHS
At26    270 DVVNGTVSSQKTVRTTFIAMFGDTTTLLSILNRRFPELGLVRSDCTETS
At27    270 RAAGNDGN--KTVTMTYLGQFLGEKGTILKVMENATPELGLTQKDCTEHS
EcBBE   280 SVLGGADE--KQVWLTMLGFHFSLKTVAKSTFDLLFDEIGIVEEDYLEHS
PsBBE   284 SVLGGVNG--NDAWLMFLGDHLGRKDAAKTIIDEKFPELGIVDKEFQEMS
```

FIG. 10A

```
MS59    338  NVESVLYYTGFPSGTPTTALLSRTP-QRLNPFKIKSDYVQNPISKRQFEF
WL64    346  WIESVLFYTNFPIGTPTTALLSRTP-QRLNPFKIKSDYVKNTSKQGFES
At26    320  WIQSVLFWDNIQVGSSETLLLQRN--QPVNYLKRKSDYVREPISRTGLES
At27    318  WIEAALFHGFPTGSEIEILLQLKSPLGKDYFKATSDFVKEPIPVIGFKG
EcBBE   328  WGESFAYLAGLET---VSQLNWRFLKFDERAFKTKVDLTKEPLPSKAFYG
PsBBE   332  WGESMAFLSGLDT---ISELNWRFLKFDERAFKTKVDFTKVSVPLNVFRH

MS59      1  FLFERLKELENQMLAFNPYGGRHSEISEFAKPFPHRSGNIAKIQYEVNME
WL64      1  SLFERMKELENQMLAFNPYGGRHSEISEFAKPFPHRSGNIAKIQYEVMWD
At26      1  SLWKKMIELEIPTMAFNPYGGEHGRISSTVPFPTRAGNLWKIQYGANWR
At27      1  GLFKRLIEGNTTSLNWTPYGGMHSKIPESAIPFPHRNGTLFKILYYARWL
EcBBE     1  GLLERLSKEPNGSIALNGFGGQHSKISSDFTPPPHRSGTRLMVEYIVANN
PsBBE     1  HALEMLSEQPGGSIALHGFGGKHSEISTDFTPFPHRKGTKLMFEMIIAWN

MS59     51  DLSDEAENRYLNFTRLMYDYMTPFVSKNPRKAFLNYRDLDIG-INSHG--
WL64     51  ELGVEAANRYLNFTRVMYDYMTPFVSKNPREAFLNYRDLDIG-VNSHG--
At26     51  DET--LTDRYMELTRKLYQFHTPFVSKNPROSFPNYRDVDLG-INSHHG-
At27     51  END-KTSSRKINWIKEIYNHEAPLVSSNPROAYVNYRDLDFG-QMKWN--
EcBBE    51  QSEQKKKTEFEDWLEKVYEFHKPFVSKNPRLGYVNHIDLDLG-IDWGNKT
PsBBE    51  QDEESKIGEFSEWLAKFYDYLEPFVSKEPRVGYVNHIDLDIGGIDWRNKS

MS59     98  -RNAMTEGMV-YSHKYFHETNYKRLVSVKTKVDPDNFFRNEQSIPTLSS-
WL64     98  -KNAKGEGMV-YSHKYFHETNYKRLTMVKTRVDPSHFFRNEQSIPTLSSS
At26     97  KISSYVEGKR-YSKKYFAG-NFSRLVKIKTRVDSGHFFRNEQSIPVLP--
At27     97  AKVNFIEAKI-WSPKYFHG-NFDRLVKIKTKVDPENFFRHQSIPPMPY-
EcBBE   101  VVNNAIEISKSWSESYFLS-NYERLIRAKTLIDPNHVFNKPQSIPPMANF
PsBBE   101  STTMAVEIARNWSERYFSS-NYERLVKAKTLIDPNHVFNPSIPPMMKF

MS59         ------------------
WL64    146  WK----------------
At26         ------------------
At27         ------------------
EcBBE   150  D--YLEKTLGSDGGEVVI
PsBBE   150  EEIYHLKEL---------
```

FIG. 10B

SEQUENCE LISTING (1) GENERAL INFORMATION:

(iii) NUMBER OF SEQUENCES: 77

(2) INFORMATION FOR SEQ ID NO: 1:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO -continued (v) FRAGMENT TYPE: internal (vi) ORIGINAL SOURCE:
            (A) ORGANISM: Helianthus annuus
            (B) STRAIN: cv. zebulon (xi) SEQUENCE DESCRIPTION: SEQ ID NO: 1:

Ser Ile Asn Val Asp Ile Glu Gln Glu Thr Ala Trp Val Gln Ala Gly
1               5                   10                  15

Ala Thr Leu Gly Glu Val Tyr Tyr Arg
            20                  25

(2) INFORMATION FOR SEQ ID NO: 2:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
            (A) ORGANISM: Helianthus annuus
            (B) STRAIN: cv. zebulon (xi) SEQUENCE DESCRIPTION: SEQ ID NO: 2:

Asp Pro Ser Phe Pro Ile Thr Gly Glu Val Tyr Thr Pro Gly Xaa Ser
1               5                   10                  15

Ser Phe Pro Thr Val Leu Gln Asn Tyr
            20                  25

(2) INFORMATION FOR SEQ ID NO: 3:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (ix) FEATURE:
            (A) NAME/KEY: misc_feature
            (B) LOCATION: 1
            (D) OTHER INFORMATION: /function= "primer"

(xi) SEQUENCE DESCRIPTION: SEQ ID NO: 3:

AACTTCTCCN AGNGTNGCNC CNGCTTGNAC CCA                                      33

(2) INFORMATION FOR SEQ ID NO: 4:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (ix) FEATURE:

(A) NAME/KEY: misc_feature
        (B) LOCATION: 1
        (D) OTHER INFORMATION: /function= "primer"

(xi) SEQUENCE DESCRIPTION: SEQ ID NO: 4:

GATCCNTCTT TCCCNATTAC TGGNGAGGTT TA                                          32

(2) INFORMATION FOR SEQ ID NO: 5:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Helianthus annuus
        (B) STRAIN: cv. zebulon (ix) FEATURE:
        (A) NAME/KEY: CDS
        (B) LOCATION: 1..354

(xi) SEQUENCE DESCRIPTION: SEQ ID NO: 5:

```
GAT CCG TCT TTC CCG ATT ACT GGG GAG GTT TAC ACT CCC GGA AAC TCA        48
Asp Pro Ser Phe Pro Ile Thr Gly Glu Val Tyr Thr Pro Gly Asn Ser
 1               5                  10                  15

TCT TTT CCT ACC GTC TTG CAA AAC TAC ATC CGA AAC CTT CGG TTC AAT        96
Ser Phe Pro Thr Val Leu Gln Asn Tyr Ile Arg Asn Leu Arg Phe Asn
             20                  25                  30

GAA ACT ACC ACA CCA AAA CCC TTT TTA ATC ATC ACA GCC GAA CAT GTT       144
Glu Thr Thr Thr Pro Lys Pro Phe Leu Ile Ile Thr Ala Glu His Val
         35                  40                  45

TCC CAC ATT CAG GCA GCT GTG GTT TGT GGC AAA CAA AAC CGG TTG CTA       192
Ser His Ile Gln Ala Ala Val Val Cys Gly Lys Gln Asn Arg Leu Leu
     50                  55                  60

CTG AAA ACC AGA AGC GGT GGT CAT GAT TAT GAA GGT CTT TCC TAC CTT       240
Leu Lys Thr Arg Ser Gly Gly His Asp Tyr Glu Gly Leu Ser Tyr Leu
 65                  70                  75                  80

ACA AAC ACA AAC CAA CCC TTC TTC ATT GTG GAC ATG TTC AAT TTA AGG       288
Thr Asn Thr Asn Gln Pro Phe Phe Ile Val Asp Met Phe Asn Leu Arg
                 85                  90                  95

TCC ATA AAC GTA GAT ATC GAA CAA GAA ACC GCA TGG GTC CAA GCC GGC       336
Ser Ile Asn Val Asp Ile Glu Gln Glu Thr Ala Trp Val Gln Ala Gly
            100                 105                 110

GCC ACC CTC GGA GAA GTT                                                354
Ala Thr Leu Gly Glu Val
        115
```

(2) INFORMATION FOR SEQ ID NO: 6:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 6:

```
Asp Pro Ser Phe Pro Ile Thr Gly Glu Val Tyr Thr Pro Gly Asn Ser
 1               5                  10                  15
```

```
Ser Phe Pro Thr Val Leu Gln Asn Tyr Ile Arg Asn Leu Arg Phe Asn
            20                  25                  30

Glu Thr Thr Thr Pro Lys Pro Phe Leu Ile Ile Thr Ala Glu His Val
        35                  40                  45

Ser His Ile Gln Ala Ala Val Val Cys Gly Lys Gln Asn Arg Leu Leu
    50                  55                  60

Leu Lys Thr Arg Ser Gly Gly His Asp Tyr Glu Gly Leu Ser Tyr Leu
65                  70                  75                  80

Thr Asn Thr Asn Gln Pro Phe Phe Ile Val Asp Met Phe Asn Leu Arg
                85                  90                  95

Ser Ile Asn Val Asp Ile Glu Gln Glu Thr Ala Trp Val Gln Ala Gly
            100                 105                 110

Ala Thr Leu Gly Glu Val
        115

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /function= "primer"

(xi) SEQUENCE DESCRIPTION: SEQ ID NO: 7:

CAGGCAGCTG TGGTTTGTGG C                                          21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /function= "primer"

(xi) SEQUENCE DESCRIPTION: SEQ ID NO: 8:

GTCCACAATG AAGAAGGGTT G                                          21

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear
```

```
        (ii) MOLECULE TYPE: cDNA (iii) HYPOTHETICAL: NO (iv) ANTI-SENSE: NO (ix) FEATURE:
             (A) NAME/KEY: misc_feature
             (B) LOCATION: 1
             (D) OTHER INFORMATION: /function= "primer"

(xi) SEQUENCE DESCRIPTION: SEQ ID NO: 9:

ACGTAGATAT CGAACAAGAA ACCGC                                         25

(2) INFORMATION FOR SEQ ID NO: 10:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

GCTTTACTAC ACGGGCTTCC CCAG                                          24

(2) INFORMATION FOR SEQ ID NO: 11:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 11:

CTGGGGAAGC CCGTGTAGTA AAGC                                          24

(2) INFORMATION FOR SEQ ID NO: 12:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 12:

GGTACTCCAA CCACGGCGCT C                                             21

(2) INFORMATION FOR SEQ ID NO: 13:

(i) SEQUENCE CHARACTERISTICS:
             (A) LENGTH: 25 base pairs
             (B) TYPE: nucleic acid
             (C) STRANDEDNESS: single
```

```
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

CGGGAAGTTG CAGAAGATTG GGTTG                                                 25

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

GAGCAAGAGA AGAAGGAGAC                                                       20

(2) INFORMATION FOR SEQ ID NO: 15:

(i) SEQUENCE CHARACTERISTICS:
        (A) LENGTH: 1784 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Helianthus annuus
        (B) STRAIN: Zebulon (ix) FEATURE:
        (A) NAME/KEY: CDS
        (B) LOCATION: 21..1608

(xi) SEQUENCE DESCRIPTION: SEQ ID NO: 15:

ATATCACATC TTCTTTCAAC ATG CAA ACT TCC ATT CTT ACT CTC CTT CTT               50
                     Met Gln Thr Ser Ile Leu Thr Leu Leu Leu
                      1               5                  10

CTC TTG CTC TCA ACC CAA TCT TCT GCA ACT TCC CGT TCC ATT ACA GAT             98
Leu Leu Leu Ser Thr Gln Ser Ser Ala Thr Ser Arg Ser Ile Thr Asp
             15                  20                  25

CGC TTC ATT CAA TGT TTA CAC GAC CGG GCC GAC CCT TCA TTT CCG ATA            146
Arg Phe Ile Gln Cys Leu His Asp Arg Ala Asp Pro Ser Phe Pro Ile
         30                  35                  40

ACC GGA GAG GTT TAC ACT CCC GGA AAC TCA TCT TTT CCT ACC GTC TTG            194
Thr Gly Glu Val Tyr Thr Pro Gly Asn Ser Ser Phe Pro Thr Val Leu
     45                  50                  55

CAA AAC TAC ATC CGA AAC CTT CGG TTC AAT GAA ACT ACC ACA CCA AAA            242
Gln Asn Tyr Ile Arg Asn Leu Arg Phe Asn Glu Thr Thr Thr Pro Lys
 60                  65                  70

CCC TTT TTA ATC ATC ACA GCC GAA CAT GTT TCC CAC ATT CAG GCA GCT            290
Pro Phe Leu Ile Ile Thr Ala Glu His Val Ser His Ile Gln Ala Ala
 75                  80                  85                  90
```

-continued

| | | |
|---|---|---|
| GTG GTT TGT GGC AAA CAA AAC CGG TTG CTA CTG AAA ACC AGA AGC GGT<br>Val Val Cys Gly Lys Gln Asn Arg Leu Leu Leu Lys Thr Arg Ser Gly<br>95 100 105 | 338 | |
| GGT CAT GAT TAT GAA GGT CTT TCC TAC CTT ACA AAC ACA AAC CAA CCC<br>Gly His Asp Tyr Glu Gly Leu Ser Tyr Leu Thr Asn Thr Asn Gln Pro<br>110 115 120 | 386 | |
| TTC TTC ATT GTG GAC ATG TTC AAT TTA AGG TCC ATA AAC GTA GAT ATC<br>Phe Phe Ile Val Asp Met Phe Asn Leu Arg Ser Ile Asn Val Asp Ile<br>125 130 135 | 434 | |
| GAA CAA GAA ACC GCA TGG GTC CAA GCC GGT GCG ACT CTT GGT GAA GTG<br>Glu Gln Glu Thr Ala Trp Val Gln Ala Gly Ala Thr Leu Gly Glu Val<br>140 145 150 | 482 | |
| TAC TAT CGA ATA GCG GAG AAA AGT AAC AAG CAT GGT TTT CCG GCA GGG<br>Tyr Tyr Arg Ile Ala Glu Lys Ser Asn Lys His Gly Phe Pro Ala Gly<br>155 160 165 170 | 530 | |
| GTT TGT CCA ACG GTT GGC GTT GGT GGG CAT TTT AGT GGT GGT GGG TAT<br>Val Cys Pro Thr Val Gly Val Gly Gly His Phe Ser Gly Gly Gly Tyr<br>175 180 185 | 578 | |
| GGT AAT TTG ATG AGA AAA TAT GGT TTG TCG GTT GAT AAT ATT GTT GAT<br>Gly Asn Leu Met Arg Lys Tyr Gly Leu Ser Val Asp Asn Ile Val Asp<br>190 195 200 | 626 | |
| GCT CAA ATA ATA GAT GTG AAT GGC AAG CTT TTG GAT CGA AAG AGT ATG<br>Ala Gln Ile Ile Asp Val Asn Gly Lys Leu Leu Asp Arg Lys Ser Met<br>205 210 215 | 674 | |
| GGT GAG GAT TTG TTT TGG GCG ATC ACC GGC GGT GGT GGT GTT AGT TTT<br>Gly Glu Asp Leu Phe Trp Ala Ile Thr Gly Gly Gly Gly Val Ser Phe<br>220 225 230 | 722 | |
| GGT GTG GTT CTA GCC TAC AAA ATC AAA CTA GTT CGT GTT CCG GAG GTT<br>Gly Val Val Leu Ala Tyr Lys Ile Lys Leu Val Arg Val Pro Glu Val<br>235 240 245 250 | 770 | |
| GTG ACC GTG TTT ACC ATT GAA AGA AGA GAG GAA CAA AAC CTC AGC ACC<br>Val Thr Val Phe Thr Ile Glu Arg Arg Glu Glu Gln Asn Leu Ser Thr<br>255 260 265 | 818 | |
| ATC GCG GAA CGA TGG GTA CAA GTT GCT GAT AAG CTA GAT AGA GAT CTT<br>Ile Ala Glu Arg Trp Val Gln Val Ala Asp Lys Leu Asp Arg Asp Leu<br>270 275 280 | 866 | |
| TTC CTT CGA ATG ACC TTT AGT GTC ATA AAC GAT ACC AAC GGT GGA AAG<br>Phe Leu Arg Met Thr Phe Ser Val Ile Asn Asp Thr Asn Gly Gly Lys<br>285 290 295 | 914 | |
| ACA GTC CGT GCT ATC TTT CCA ACG TTG TAC CTT GGA AAC TCG AGG AAT<br>Thr Val Arg Ala Ile Phe Pro Thr Leu Tyr Leu Gly Asn Ser Arg Asn<br>300 305 310 | 962 | |
| CTT GTT ACA CTT TTG AAT AAA GAT TTC CCC GAG TTA GGG TTG CAA GAA<br>Leu Val Thr Leu Leu Asn Lys Asp Phe Pro Glu Leu Gly Leu Gln Glu<br>315 320 325 330 | 1010 | |
| TCG GAT TGT ACT GAA ATG AGT TGG GTT GAG TCT GTG CTT TAC TAC ACG<br>Ser Asp Cys Thr Glu Met Ser Trp Val Glu Ser Val Leu Tyr Tyr Thr<br>335 340 345 | 1058 | |
| GGC TTC CCC AGT GGT ACT CCA ACC ACG GCG CTC TTA AGC CGT ACT CCT<br>Gly Phe Pro Ser Gly Thr Pro Thr Thr Ala Leu Leu Ser Arg Thr Pro<br>350 355 360 | 1106 | |
| CAA AGA CTC AAC CCA TTC AAG ATC AAA TCC GAT TAT GTG CAA AAT CCT<br>Gln Arg Leu Asn Pro Phe Lys Ile Lys Ser Asp Tyr Val Gln Asn Pro<br>365 370 375 | 1154 | |
| ATT TCT AAA CGA CAG TTC GAG TTC ATC TTC GAA AGG CTG AAA GAA CTT<br>Ile Ser Lys Arg Gln Phe Glu Phe Ile Phe Glu Arg Leu Lys Glu Leu<br>380 385 390 | 1202 | |
| GAA AAC CAA ATG TTG GCT TTC AAC CCA TAT GGT GGT AGA ATG AGT GAA<br>Glu Asn Gln Met Leu Ala Phe Asn Pro Tyr Gly Gly Arg Met Ser Glu | 1250 | |

-continued

| | |
|---|---|
| ATA TCC GAA TTC GCA AAG CCT TTC CCA CAT AGA TCG GGT AAC ATA GCG<br>Ile Ser Glu Phe Ala Lys Pro Phe Pro His Arg Ser Gly Asn Ile Ala<br>                        415                                  420                                425 | 298 |
| AAA ATT CAA TAC GAA GTA AAC TGG GAG GAT CTT AGC GAT GAA GCC GAA<br>Lys Ile Gln Tyr Glu Val Asn Trp Glu Asp Leu Ser Asp Glu Ala Glu<br>                    430                                  435                              440 | 346 |
| AAT CGT TAC TTG AAT TTC ACA AGG CTG ATG TAT GAT TAC ATG ACC CCA<br>Asn Arg Tyr Leu Asn Phe Thr Arg Leu Met Tyr Asp Tyr Met Thr Pro<br>                445                                  450                                  455 | 394 |
| TTT GTG TCG AAA AAC CCT AGA AAA GCA TTT TTG AAC TAT AGG GAT TTG<br>Phe Val Ser Lys Asn Pro Arg Lys Ala Phe Leu Asn Tyr Arg Asp Leu<br>            460                                  465                                  470 | 442 |
| GAT ATT GGT ATC AAC AGC CAT GGC AGG AAT GCT TAT ACT GAA GGA ATG<br>Asp Ile Gly Ile Asn Ser His Gly Arg Asn Ala Tyr Thr Glu Gly Met<br>475                                480                                  485                              490 | 490 |
| GTT TAT GGG CAC AAG TAT TTC AAA GAG ACA AAT TAC AAG AGG CTA GTA<br>Val Tyr Gly His Lys Tyr Phe Lys Glu Thr Asn Tyr Lys Arg Leu Val<br>                        495                                  500                              505 | 538 |
| AGT GTG AAG ACT AAA GTT GAT CCT GAC AAC TTC TTT AGG AAT GAG CAA<br>Ser Val Lys Thr Lys Val Asp Pro Asp Asn Phe Phe Arg Asn Glu Gln<br>                  510                                  515                                520 | 586 |
| AGC ATC CCA ACT TTG TCA TCT T GAAGAACGTA CATATATAAA TAAATACCTT<br>Ser Ile Pro Thr Leu Ser Ser<br>            525 | 1638 |
| TGTGCATGGT ATTTTCAGGG TGTTAAAGTG ATATTCAGAT ATTTATGATA GAATTTTG | 1698 |
| TTGTATTTTA TACAATCAAA ATTGTATGGT TCTCCGAATT TCTCTTTTTA ATTCTGAA | 1758 |
| ATACATATTA GTATTGTCAA AAAAAA | 1784 |

(2) INFORMATION FOR SEQ ID NO: 16:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO: 16:

Met Gln Thr Ser Ile Leu Thr Leu Leu Leu Leu Leu Ser Thr Gln
1                5                    10                    15

Ser Ser Ala Thr Ser Arg Ser Ile Thr Asp Arg Phe Ile Gln Cys Leu
              20                        25                        30

His Asp Arg Ala Asp Pro Ser Phe Pro Ile Thr Gly Glu Val Tyr Thr
              35                        40                        45

Pro Gly Asn Ser Ser Phe Pro Thr Val Leu Gln Asn Tyr Ile Arg Asn
    50                        55                        60

Leu Arg Phe Asn Glu Thr Thr Pro Lys Pro Phe Leu Ile Ile Thr
65                        70                        75                        80

Ala Glu His Val Ser His Ile Gln Ala Val Val Cys Gly Lys Gln
                  85                        90                        95

Asn Arg Leu Leu Leu Lys Thr Arg Ser Gly Gly His Asp Tyr Glu Gly
            100                        105                        110

Leu Ser Tyr Leu Thr Asn Thr Asn Gln Pro Phe Phe Ile Val Asp Met
            115                        120                        125

Phe Asn Leu Arg Ser Ile Asn Val Asp Ile Glu Gln Glu Thr Ala Trp
    130                        135                        140

-continued

```
Val Gln Ala Gly Ala Thr Leu Gly Glu Val Tyr Tyr Arg Ile Ala Glu
145                 150                 155                 160

Lys Ser Asn Lys His Gly Phe Pro Ala Gly Val Cys Pro Thr Val Gly
                165                 170                 175

Val Gly Gly His Phe Ser Gly Gly Tyr Gly Asn Leu Met Arg Lys
            180                 185                 190

Tyr Gly Leu Ser Val Asp Asn Ile Val Asp Ala Gln Ile Ile Asp Val
        195                 200                 205

Asn Gly Lys Leu Leu Asp Arg Lys Ser Met Gly Glu Asp Leu Phe Trp
    210                 215                 220

Ala Ile Thr Gly Gly Gly Val Ser Phe Gly Val Val Leu Ala Tyr
225                 230                 235                 240

Lys Ile Lys Leu Val Arg Val Pro Glu Val Thr Val Phe Thr Ile
                245                 250                 255

Glu Arg Arg Glu Glu Gln Asn Leu Ser Thr Ile Ala Glu Arg Trp Val
                260                 265                 270

Gln Val Ala Asp Lys Leu Asp Arg Asp Leu Phe Leu Arg Met Thr Phe
            275                 280                 285

Ser Val Ile Asn Asp Thr Asn Gly Gly Lys Thr Val Arg Ala Ile Phe
        290                 295                 300

Pro Thr Leu Tyr Leu Gly Asn Ser Arg Asn Leu Val Thr Leu Leu Asn
305                 310                 315                 320

Lys Asp Phe Pro Glu Leu Gly Leu Gln Glu Ser Asp Cys Thr Glu Met
                325                 330                 335

Ser Trp Val Glu Ser Val Leu Tyr Tyr Thr Gly Phe Pro Ser Gly Thr
                340                 345                 350

Pro Thr Thr Ala Leu Leu Ser Arg Thr Pro Gln Arg Leu Asn Pro Phe
            355                 360                 365

Lys Ile Lys Ser Asp Tyr Val Gln Asn Pro Ile Ser Lys Arg Gln Phe
        370                 375                 380

Glu Phe Ile Phe Glu Arg Leu Lys Glu Leu Glu Asn Gln Met Leu Ala
385                 390                 395                 400

Phe Asn Pro Tyr Gly Gly Arg Met Ser Glu Ile Ser Glu Phe Ala Lys
                405                 410                 415

Pro Phe Pro His Arg Ser Gly Asn Ile Ala Lys Ile Gln Tyr Glu Val
            420                 425                 430

Asn Trp Glu Asp Leu Ser Asp Glu Ala Glu Asn Arg Tyr Leu Asn Phe
        435                 440                 445

Thr Arg Leu Met Tyr Asp Tyr Met Thr Pro Phe Val Ser Lys Asn Pro
    450                 455                 460

Arg Lys Ala Phe Leu Asn Tyr Arg Asp Leu Asp Ile Gly Ile Asn Ser
465                 470                 475                 480

His Gly Arg Asn Ala Tyr Thr Glu Gly Met Val Tyr Gly His Lys Tyr
                485                 490                 495

Phe Lys Glu Thr Asn Tyr Lys Arg Leu Val Ser Val Lys Thr Lys Val
            500                 505                 510

Asp Pro Asp Asn Phe Phe Arg Asn Glu Gln Ser Ile Pro Thr Leu Ser
        515                 520                 525

Ser
```

(2) INFORMATION FOR SEQ ID NO: 17:

(i) SEQUENCE CHARACTERISTICS:
        (A) LENGTH: 27 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 17:

CCGCCATGGA GACTTCCATT CTTACTC                                              27

(2) INFORMATION FOR SEQ ID NO: 18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 18:

GCCGGATCCT CAAGATGACA AAGTTGGGAT GCT                                       33

(2) INFORMATION FOR SEQ ID NO: 19:

(i) SEQUENCE CHARACTERISTICS:
        (A) LENGTH: 1589 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Helianthus annuus
        (B) STRAIN: Zebulon (ix) FEATURE:
        (A) NAME/KEY: CDS
        (B) LOCATION: 1..1590

(xi) SEQUENCE DESCRIPTION: SEQ ID NO: 19:

ATG GAG ACT TCC ATT CTT ACT CTC CTT CTT CTC TTG CTC TCA ACC CAA            48
Met Glu Thr Ser Ile Leu Thr Leu Leu Leu Leu Leu Leu Ser Thr Gln
 1               5                  10                  15

TCT TCT GCA ACT TCC CGT TCC ATT ACA GAT CGC TTC ATT CAA TGT TTA            96
Ser Ser Ala Thr Ser Arg Ser Ile Thr Asp Arg Phe Ile Gln Cys Leu
                20                  25                  30

CAC GAC CGG GCC GAC CCT TCA TTT CCG ATA ACC GGA GAG GTT TAC ACT           144
His Asp Arg Ala Asp Pro Ser Phe Pro Ile Thr Gly Glu Val Tyr Thr
            35                  40                  45

CCC GGA AAC TCA TCT TTT CCT ACC GTC TTG CAA AAC TAC ATC CGA AAC           192
Pro Gly Asn Ser Ser Phe Pro Thr Val Leu Gln Asn Tyr Ile Arg Asn
 50                  55                  60

CTT CGG TTC AAT GAA ACT ACC ACA CCA AAA CCC TTT TTA ATC ATC ACA           240
Leu Arg Phe Asn Glu Thr Thr Thr Pro Lys Pro Phe Leu Ile Ile Thr
 65                  70                  75                  80

GCC GAA CAT GTT TCC CAC ATT CAG GCA GCT GTG GTT TGT GGC AAA CAA           288
```

```
                Ala Glu His Val Ser His Ile Gln Ala Ala Val Val Cys Gly Lys Gln
                                85              90                  95

AAC CGG TTG CTA CTG AAA ACC AGA AGC GGT GGT CAT GAT TAT GAA GGT                    336
Asn Arg Leu Leu Leu Lys Thr Arg Ser Gly Gly His Asp Tyr Glu Gly
            100                 105                 110

CTT TCC TAC CTT ACA AAC ACA AAC CAA CCC TTC TTC ATT GTG GAC ATG                    384
Leu Ser Tyr Leu Thr Asn Thr Asn Gln Pro Phe Phe Ile Val Asp Met
        115                 120                 125

TTC AAT TTA AGG TCC ATA AAC GTA GAT ATC GAA CAA GAA ACC GCA TGG                    432
Phe Asn Leu Arg Ser Ile Asn Val Asp Ile Glu Gln Glu Thr Ala Trp
    130                 135                 140

GTC CAA GCC GGT GCG ACT CTT GGT GAA GTG TAC TAT CGA ATA GCG GAG                    480
Val Gln Ala Gly Ala Thr Leu Gly Glu Val Tyr Tyr Arg Ile Ala Glu
145                 150                 155                 160

AAA AGT AAC AAG CAT GGT TTT CCG GCA GGG GTT TGT CCA ACG GTT GGC                    528
Lys Ser Asn Lys His Gly Phe Pro Ala Gly Val Cys Pro Thr Val Gly
                165                 170                 175

GTT GGT GGG CAT TTT AGT GGT GGT GGG TAT GGT AAT TTG ATG AGA AAA                    576
Val Gly Gly His Phe Ser Gly Gly Gly Tyr Gly Asn Leu Met Arg Lys
            180                 185                 190

TAT GGT TTG TCG GTT GAT AAT ATT GTT GAT GCT CAA ATA ATA GAT GTG                    624
Tyr Gly Leu Ser Val Asp Asn Ile Val Asp Ala Gln Ile Ile Asp Val
        195                 200                 205

AAT GGC AAG CTT TTG GAT CGA AAG AGT ATG GGT GAG GAT TTG TTT TGG                    672
Asn Gly Lys Leu Leu Asp Arg Lys Ser Met Gly Glu Asp Leu Phe Trp
    210                 215                 220

GCG ATC ACC GGC GGT GGT GGT GTT AGT TTT GGT GTG GTT CTA GCC TAC                    720
Ala Ile Thr Gly Gly Gly Gly Val Ser Phe Gly Val Val Leu Ala Tyr
225                 230                 235                 240

AAA ATC AAA CTA GTT CGT GTT CCG GAG GTT GTG ACC GTG TTT ACC ATT                    768
Lys Ile Lys Leu Val Arg Val Pro Glu Val Val Thr Val Phe Thr Ile
                245                 250                 255

GAA AGA AGA GAG GAA CAA AAC CTC AGC ACC ATC GCG GAA CGA TGG GTA                    816
Glu Arg Arg Glu Glu Gln Asn Leu Ser Thr Ile Ala Glu Arg Trp Val
            260                 265                 270

CAA GTT GCT GAT AAG CTA GAT AGA GAT CTT TTC CTT CGA ATG ACC TTT                    864
Gln Val Ala Asp Lys Leu Asp Arg Asp Leu Phe Leu Arg Met Thr Phe
        275                 280                 285

AGT GTC ATA AAC GAT ACC AAC GGT GGA AAG ACA GTC CGT GCT ATC TTT                    912
Ser Val Ile Asn Asp Thr Asn Gly Gly Lys Thr Val Arg Ala Ile Phe
    290                 295                 300

CCA ACG TTG TAC CTT GGA AAC TCG AGG AAT CTT GTT ACA CTT TTG AAT                    960
Pro Thr Leu Tyr Leu Gly Asn Ser Arg Asn Leu Val Thr Leu Leu Asn
305                 310                 315                 320

AAA GAT TTC CCC GAG TTA GGG TTG CAA GAA TCG GAT TGT ACT GAA ATG1                   008
Lys Asp Phe Pro Glu Leu Gly Leu Gln Glu Ser Asp Cys Thr Glu Met
                325                 330                 335

AGT TGG GTT GAG TCT GTG CTT TAC TAC ACG GGC TTC CCC AGT GGT ACT                    1056
Ser Trp Val Glu Ser Val Leu Tyr Tyr Thr Gly Phe Pro Ser Gly Thr
            340                 345                 350

CCA ACC ACG GCG CTC TTA AGC CGT ACT CCT CAA AGA CTC AAC CCA TTC                    1104
Pro Thr Thr Ala Leu Leu Ser Arg Thr Pro Gln Arg Leu Asn Pro Phe
        355                 360                 365

AAG ATC AAA TCC GAT TAT GTG CAA AAT CCT ATT TCT AAA CGA CAG TTC                    1152
Lys Ile Lys Ser Asp Tyr Val Gln Asn Pro Ile Ser Lys Arg Gln Phe
    370                 375                 380

GAG TTC ATC TTC GAA AGG ATG AAA GAA CTT GAA AAC CAA ATG TTG GCG                    1200
Glu Phe Ile Phe Glu Arg Met Lys Glu Leu Glu Asn Gln Met Leu Ala
385                 390                 395                 400
```

```
TTC AAC CCA TAT GGT GGT AGA ATG AGT GAA ATA TCC GAA TTC GCA AAG      1248
Phe Asn Pro Tyr Gly Gly Arg Met Ser Glu Ile Ser Glu Phe Ala Lys
            405                 410                 415

CCT TTC CCA CAT AGA TCG GGT AAC ATA GCG AAG ATT CAA TAC GAA GTA      1296
Pro Phe Pro His Arg Ser Gly Asn Ile Ala Lys Ile Gln Tyr Glu Val
            420                 425                 430

AAC TGG GAG GAT CTT AGC GAT GAA GCC GAA AAT CGT TAC TTG AAT TTC      1344
Asn Trp Glu Asp Leu Ser Asp Glu Ala Glu Asn Arg Tyr Leu Asn Phe
            435                 440                 445

ACA AGG CTG ATG TAT GAT TAC ATG ACT CCA TTT GTG TCG AAA AAC CCT      1392
Thr Arg Leu Met Tyr Asp Tyr Met Thr Pro Phe Val Ser Lys Asn Pro
    450                 455                 460

AGA GAA GCA TTT TTG AAC TAT AGG GAT TTG GAT ATT GGT ATC AAC AGC      1440
Arg Glu Ala Phe Leu Asn Tyr Arg Asp Leu Asp Ile Gly Ile Asn Ser
465                 470                 475                 480

CAT GGC AGG AAT GCT TAT ACT GAA GGA ATG GTT TAT GGG CAC AAA TAT      1488
His Gly Arg Asn Ala Tyr Thr Glu Gly Met Val Tyr Gly His Lys Tyr
            485                 490                 495

TTC AAA GAG ACA AAT TAC AAG AGG CTA GTA AGT GTG AAG ACT AAA GTT      1536
Phe Lys Glu Thr Asn Tyr Lys Arg Leu Val Ser Val Lys Thr Lys Val
            500                 505                 510

GAT CCT GAC AAC TTC TTT AGG AAT GAG CAA AGC ATC CCA ACT TTG TCA      1584
Asp Pro Asp Asn Phe Phe Arg Asn Glu Gln Ser Ile Pro Thr Leu Ser
            515                 520                 525

TCT TG                                                                1589
Ser
    530

(2) INFORMATION FOR SEQ ID NO: 20:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO: 20:

Met Glu Thr Ser Ile Leu Thr Leu Leu Leu Leu Leu Ser Thr Gln
  1               5                  10                  15

Ser Ser Ala Thr Ser Arg Ser Ile Thr Asp Arg Phe Ile Gln Cys Leu
              20                  25                  30

His Asp Arg Ala Asp Pro Ser Phe Pro Ile Thr Gly Glu Val Tyr Thr
          35                  40                  45

Pro Gly Asn Ser Ser Phe Pro Thr Val Leu Gln Asn Tyr Ile Arg Asn
      50                  55                  60

Leu Arg Phe Asn Glu Thr Thr Thr Pro Lys Pro Phe Leu Ile Ile Thr
 65                  70                  75                  80

Ala Glu His Val Ser His Ile Gln Ala Val Val Cys Gly Lys Gln
              85                  90                  95

Asn Arg Leu Leu Leu Lys Thr Arg Ser Gly His Asp Tyr Glu Gly
              100                 105                 110

Leu Ser Tyr Leu Thr Asn Thr Asn Gln Pro Phe Ile Val Asp Met
          115                 120                 125

Phe Asn Leu Arg Ser Ile Asn Val Asp Ile Glu Gln Glu Thr Ala Trp
          130                 135                 140

Val Gln Ala Gly Ala Thr Leu Gly Glu Val Tyr Tyr Arg Ile Ala Glu
145                 150                 155                 160

Lys Ser Asn Lys His Gly Phe Pro Ala Gly Val Cys Pro Thr Val Gly
```

```
                165                 170                 175
Val Gly Gly His Phe Ser Gly Gly Tyr Gly Asn Leu Met Arg Lys
            180                 185                 190

Tyr Gly Leu Ser Val Asp Asn Ile Val Asp Ala Gln Ile Ile Asp Val
            195                 200                 205

Asn Gly Lys Leu Leu Asp Arg Lys Ser Met Gly Glu Asp Leu Phe Trp
            210                 215                 220

Ala Ile Thr Gly Gly Gly Val Ser Phe Gly Val Leu Ala Tyr
225             230                 235                 240

Lys Ile Lys Leu Val Arg Val Pro Glu Val Thr Val Phe Thr Ile
            245                 250                 255

Glu Arg Arg Glu Glu Gln Asn Leu Ser Thr Ile Ala Glu Arg Trp Val
            260                 265                 270

Gln Val Ala Asp Lys Leu Asp Arg Asp Leu Phe Leu Arg Met Thr Phe
            275                 280                 285

Ser Val Ile Asn Asp Thr Asn Gly Gly Lys Thr Val Arg Ala Ile Phe
            290                 295                 300

Pro Thr Leu Tyr Leu Gly Asn Ser Arg Asn Leu Val Thr Leu Leu Asn
305             310                 315                 320

Lys Asp Phe Pro Glu Leu Gly Leu Gln Glu Ser Asp Cys Thr Glu Met
            325                 330                 335

Ser Trp Val Glu Ser Val Leu Tyr Tyr Thr Gly Phe Pro Ser Gly Thr
            340                 345                 350

Pro Thr Thr Ala Leu Leu Ser Arg Thr Pro Gln Arg Leu Asn Pro Phe
            355                 360                 365

Lys Ile Lys Ser Asp Tyr Val Gln Asn Pro Ile Ser Lys Arg Gln Phe
            370                 375                 380

Glu Phe Ile Phe Glu Arg Met Lys Glu Leu Glu Asn Gln Met Leu Ala
385             390                 395                 400

Phe Asn Pro Tyr Gly Gly Arg Met Ser Glu Ile Ser Glu Phe Ala Lys
            405                 410                 415

Pro Phe Pro His Arg Ser Gly Asn Ile Ala Lys Ile Gln Tyr Glu Val
            420                 425                 430

Asn Trp Glu Asp Leu Ser Asp Glu Ala Glu Asn Arg Tyr Leu Asn Phe
            435                 440                 445

Thr Arg Leu Met Tyr Asp Tyr Met Thr Pro Phe Val Ser Lys Asn Pro
450             455                 460

Arg Glu Ala Phe Leu Asn Tyr Arg Asp Leu Asp Ile Gly Ile Asn Ser
465             470                 475                 480

His Gly Arg Asn Ala Tyr Thr Glu Gly Met Val Tyr Gly His Lys Tyr
            485                 490                 495

Phe Lys Glu Thr Asn Tyr Lys Arg Leu Val Ser Val Lys Thr Lys Val
            500                 505                 510

Asp Pro Asp Asn Phe Phe Arg Asn Glu Gln Ser Ile Pro Thr Leu Ser
            515                 520                 525

Ser (2) INFORMATION FOR SEQ ID NO: 21:

(i) SEQUENCE CHARACTERISTICS:
        (A) LENGTH: 350 base pairs
        (B) TYPE: nucleic acid
        (C) STRANDEDNESS: double
        (D) TOPOLOGY: linear
```

(ii) MOLECULE TYPE: cDNA to mRNA (iii) HYPOTHETICAL: NO (iv) ANTI-SENSE: NO (vi) ORIGINAL SOURCE:
             (A) ORGANISM: Arabidopsis thaliana
             (B) STRAIN: ecotype Columbia (ix) FEATURE:
             (A) NAME/KEY: CDS
             (B) LOCATION: 2..350

(xi) SEQUENCE DESCRIPTION: SEQ ID NO: 21:

GAGAAACTCG GAGACTTTCA CACAATGCCT AACCTCAAAC TCCGACCCCA AACATCCCAT      60

CTCCCCCGCT ATCTTCTTCT CCGGAAATGG CTCCTACTCC TCCGTATTAC AAGCCAACA      120

CCGTAACCTC CGCTTCAACA CCACCTCAAC TCCGAAACCC TTCCTCATAA TCGCCGCAA      180

ACATGAATCC CATGTGCAAG CCGCGATTAC TTGCGGGAAA CGCCACAACC TTCAGATGA      240

AATCAGAAGT GGAGGCCACG ACTACGATGG CTTGTCATAC GTTACATACT CTGGCAAAC      300

GTTCTTCGTC CTCGACATGT TTAACCTCCG TTCGGTGGAT GTCGACGTGG               350

(2) INFORMATION FOR SEQ ID NO: 22:

(i) SEQUENCE CHARACTERISTICS:
            (A) LENGTH: 278 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: Arabidopsis thaliana
             (B) STRAIN: ecotype Columbia (ix) FEATURE:
             (A) NAME/KEY: CDS
             (B) LOCATION: 2..278

(xi) SEQUENCE DESCRIPTION: SEQ ID NO: 22:

GGCATGGATC TCCGCCGGAG CGACTCTCGG AGAGGTTTAT TATCGGATTT GGGAGAAAAG      60

CAGAGTCCAT GGATTCCCCG CCGGAGTTTG ACCGACGGTT GGTGTTGGTG GGCATTTAA      120

CGGCGGTGGT TACGGTAACA TGGTGAGGAA GTTTGGATTA TCTGTGGATT ACGTTGAGG      180

TGCCAAGATC GTCGATGTAA ACNGTCGGGT TTTAGATCGG AAAGCAATGG GTGAGGATC      240

GTTCTGGGCG ATTACCGGTG GAGGAGGAGG TAGCGTAC                            278

(2) INFORMATION FOR SEQ ID NO: 23:

(i) SEQUENCE CHARACTERISTICS:
            (A) LENGTH: 345 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:

(A) ORGANISM: Arabidopsis thaliana
        (B) STRAIN: ecotype Columbia (ix) FEATURE:
        (A) NAME/KEY: CDS
        (B) LOCATION: 2..345

(xi) SEQUENCE DESCRIPTION: SEQ ID NO: 23:

```
TGGACATATT AGCGGAGGAG GATTCGGTAC AATAATGAGG AAATACGGTT TAGCGTCTGA      60

TAACGTTGTG GACGCACGTT TGATGGATGT AAATGGGAAA ACTCTTGACC GGAAAACGA      120

GGGAGAGGAT TTGTTTTGGG CGCTTAGAGG CGGTGGAGCT GCGAGTTTTG GCGTTGTCT      180

GTCGTGGAAG GTTAAGCTTG CTAGGGTTCC TGAAAAGGTA ACTTGTTTCA TAAGTCAAC      240

TCCGATGGGA CCTAGCATGA ACAAGCTTGT TCATAGATGG CAATCCATAG GATCAAGAN      300

GCTAGACGAA GATTTATTCA TCAGAGTCAA TATTGACAAC AGTCT                    345
```

(2) INFORMATION FOR SEQ ID NO: 24:

(i) SEQUENCE CHARACTERISTICS:
        (A) LENGTH: 695 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 1..695

(xi) SEQUENCE DESCRIPTION: SEQ ID NO: 24:

```
GTTCGTTAAA ACCTATCCTN NANGGGCNAA AGNATATCAA AGNTTGNTTA NGNAACCCAA     60

NATTTCTGAA CTGGCCNCCT TCGGTGGTAT ATGNCNAAAN CCCTTGAATC TGCGNANCC     120

ATTCCGCATA GAAACGGAAC CCTCTTCAAG ATTCTCTATT TACNCGAACT GNCTAGANN    180

AATGACAAGA CATCGAGTAG NAAAATCAAC TGGATCAAAG AGATATACAA TTACATGGC    240

CCTTATGTCT CAAGCAATCC AAGACAAGCA TATGTGAACT ACAGAGATCT AGACTTCGG    300

CAGAACAAGA ACAACGCAAA GGTTAACTTC ATTGAAGCTA AAATCTGGGG ACCTAAGTA    360

TTCAAAGGCA ATTTTGACAG ATTGGTGAAG ATTAAAACCA AGGTTGATCC AGAGAACTT    420

TTCAGGCACG AGCAGAGTAT CCCACCTATG CCCTACTAGA AGCTAGGTTC ATGAAACCA    480

TAACATTATC AAAAATAAGR ATAAATGRTA ATTGTATACA ACATGATTCG KCTTTCTTT    540

TTTCAGACAA TGTGGACACT ACTCTAAANT AAAAWGTCNA TTTACCTTAA AAAAAAAAT    600

ATCCCCNNTA ANANAAAANT GGGGGGGCCN TTTTTGGGGN TCCCGGTTTT NGGACGGGG    660

GCTTTNGGGG GGCTTGGNNT TTTTTTNGGN GCCCC                              695
```

(2) INFORMATION FOR SEQ ID NO: 25:

(i) SEQUENCE CHARACTERISTICS:
        (A) LENGTH: 495 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: Arabidopsis thaliana
             (B) STRAIN: ecotype Columbia (ix) FEATURE:
             (A) NAME/KEY: CDS
             (B) LOCATION: 2..495

(xi) SEQUENCE DESCRIPTION: SEQ ID NO: 25:

TCTGTTTTNA GGCAGAGCAG AGGAAGTTGT TGCTTTGCTT GGTAAGGAGT TTCCTGAATT      60

NAGTTTAAAG AAGGAGAACT GTTCGGAGAT GACTTGGTTT CAGTCAGCTT TATGGTGGG     120

TAATCGTGTT AACCCTACTC ANATTGATCC WAAAGTGTTT CTCGATCGGA ATCTTGATA     180

AGCGAATTTC GGAAAGAGGA AATCGGATTA CGTTGCGAGT AAGATTCCTA GAGATGGGA     240

TAAGYCTTTT TCCAAGARGA TGMCTGACCT GGGGAAAAYC GGGCTTGTTT TTAAWCCGT     300

TGGTGGGAAA ATGGCGGAGG TTACGGTTAA CGCGACGCCG TTTCCNCACC GAAGCAAGC     360

TTTTAAGATT CAGTACTCGG TGACTTNGCA AGAAAACTCT NTCGAGATAG AGAAAGGGT     420

TCTTGAATCA GGCTAACGTC CTTATAGGTT CATGACCGGG TTTTTNAGCA AGANCCCTG     480

AATNCTTACT TNAAT                                                     495

(2) INFORMATION FOR SEQ ID NO: 26:

(i) SEQUENCE CHARACTERISTICS:
            (A) LENGTH: 204 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: Arabidopsis thaliana
             (B) STRAIN: ecotype Columbia (ix) FEATURE:
             (A) NAME/KEY: CDS
             (B) LOCATION: 1..204

(xi) SEQUENCE DESCRIPTION: SEQ ID NO: 26:

AAATTAAAAC AAATCAATGT TGATATTGAA TCCAATAGTG CTTGGTTTCA ACCTGGTGCT      60

ACGCTTGGTG AGCTTTACTA CAGAATTNCA GAGAAGAGCA AAATCCATGG ATTTCCNGC     120

GGTTTNTNCA CAAGCNTAGG CATAGGTGGG TATATNANAG GCGGTGGATA CGGTACCTT     180

ATGAGGAAGT ATGGTCTTNC GGGA                                           204

(2) INFORMATION FOR SEQ ID NO: 27:

(i) SEQUENCE CHARACTERISTICS:
            (A) LENGTH: 491 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Arabidopsis thaliana
            (B) STRAIN: ecotype Columbia (ix) FEATURE:
            (A) NAME/KEY: CDS
            (B) LOCATION: 2..491

(xi) SEQUENCE DESCRIPTION: SEQ ID NO: 27:

```
GAGATTTCTC GAGCAAGATA CTCCACTGAT GATCTTTGAG CCATTGGGTG GGAAAATCAG      60

CAAGATTTCA GAAACAGAAT CTCCATATCC ACACAGAAGA GGTAATCTGT ATAATATAC     120

GTACATGGTG AAATGAAAG TGAATGANGT CGAGGAGATG AACAAACATG TCAGGTGGA      180

GAGATCGTTA CACGATTACA TGACTCCGTA TGTTTCTAAA TCGCCGAGAG GAGCTTATT     240

GANTTACAGA GATCTTGATT TGGGCTCGAC CAAAGGGATT AACACGGGTT TCGGAGATG     300

AAGGAAATGG NNGGGTGAGN CTTTTTTCAA AGGTAATTTC CAAGGGGTTA GGTTTTGGT     360

AAAGGGGAGG TTTNNCCCAN CAAATTTTTT TTCAGGANCC GGCCANGNTT TTCCCCCCC     420

TNTTTTTNGG NCCCCAATCN AAANCCCCGT TTTAAAAGGG GGGCCATTTC NTTTTTTNC     480

NNTTAAAAGG G                                                          491
```

(2) INFORMATION FOR SEQ ID NO: 28:

(i) SEQUENCE CHARACTERISTICS:
            (A) LENGTH: 407 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Arabidopsis thaliana
            (B) STRAIN: ecotype Columbia (ix) FEATURE:
            (A) NAME/KEY: CDS
            (B) LOCATION: 3..407

(xi) SEQUENCE DESCRIPTION: SEQ ID NO: 28:

```
ATTTGTTCGT GAGGTTAACT TTGACTTTAG TCAACGGTAC GAAGCCTGGT GAGAATACGG      60

TTTTAGCGAC TTTCATTGGG ATGTATTTAG GCCGGTCGGA TAAGCTGTTG ACCGTNATG     120

ACCGGGATTT CCCGGAGTTG AAGCTGAAGA AAACCGATTN TACCGAGATG AGATGGATC     180

ATTCGGTTCT GTTTTGGGAC GATTATCCGG TTGGTACACC GACTTCTGTG CTACTAAAT     240

CGCTAGTCGC AAAAAAGTTG TTCATGAAAC GAAAATCGGA CTACGTGAAG CGTCTNATT    300

TCGAGAACCC GATCTCNNGT TTGATACTCA AGAAATTTGT AGAGGTTNNG AAAGTTAAA    360

TNAATTTGGA TCCGCATTNN GGNANNNATG GTGAAACCCC NNGTTNT                  407
```

(2) INFORMATION FOR SEQ ID NO: 29:

(i) SEQUENCE CHARACTERISTICS:
            (A) LENGTH: 360 base pairs
            (B) TYPE: nucleic acid
            (C) STRANDEDNESS: double
            (D) TOPOLOGY: linear

```
    (ii) MOLECULE TYPE: cDNA to mRNA (iii) HYPOTHETICAL: NO (iv) ANTI-SENSE: NO (vi) ORIGINAL SOURCE:
         (A) ORGANISM: Arabidopsis thaliana
         (B) STRAIN: ecotype Columbia (ix) FEATURE:
         (A) NAME/KEY: CDS
         (B) LOCATION: 3..360

(xi) SEQUENCE DESCRIPTION: SEQ ID NO: 29:

ACGGCGTCGT ATTGGCCTAC AAAATAAACC TTGTTGAAGT CCCAGAAAAC GTCACCGTTT        60

TCAGAATCTC CCGGACGTTA GAACAAAATG CGACGGATAT CATTCACCGG TGGCAACAA        120

TTGCACCGAA GCTTCCCGAC GAGCTTTTCA TAAGANCAGT CATTGACGTA NAAACGGCA        180

TGTTTCATNN CTCAAAAGAC CGTCAGACAA CATTCATAGC AATGTTTCTA GGAGACACG        240

CAACTCTACT GTCGATATTA AACCGGAGAT TCCCAGAATT GGGTTTGGTC CGGTCTGAC        300

GTACCGNAAC AAGCNNTTGG ATCCAATCTG TGCTATTTTT GGGACAAATA TCCCAGGTT        360

(2) INFORMATION FOR SEQ ID NO: 30:

(i) SEQUENCE CHARACTERISTICS:
         (A) LENGTH: 427 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (A) ORGANISM: Arabidopsis thaliana
         (B) STRAIN: ecotype Columbia (ix) FEATURE:
         (A) NAME/KEY: CDS
         (B) LOCATION: 3..427

(xi) SEQUENCE DESCRIPTION: SEQ ID NO: 30:

TCTTCACTGT CACCAAAACG TTAGAACAAG ACGCAAGATT GAAGACTATT TCTAAGTGGC        60

AACAAATTTC ATCCAAGATT ATTGAAGAGA TACACATCCG AGTGGTACTC AGAGCAGCT        120

GAAATGATGG AAACAAGACT GTGACAATGA CCTACCTAGG TCAGTTTCTT GGCGAGAAA        180

GCACCTTGCT GAAGGTTATG GAGAAGGCTT TTCCAGAACT AGGGTTAACT CAAAAGGAT        240

GTACTGAAAT GAGCTGGATT GAAGCCGCCC TTTTCCATGG TGGRTTTCCA ACAGGKTCT        300

CTATTGAAAT TTTGCTTMAG CTCAAGTCGC CTYTAGGAAA AGRTTWCTTC AAAGCAACG        360

CGGATTTCGT TAAAGAACCT WTTCCTGTGA TAGGGCTCAA AGGAATATTC AAAAGATTG        420

TTGAAGG                                                               427

(2) INFORMATION FOR SEQ ID NO: 31:

(i) SEQUENCE CHARACTERISTICS:
         (A) LENGTH: 437 base pairs
         (B) TYPE: nucleic acid
         (C) STRANDEDNESS: double
         (D) TOPOLOGY: linear (ii) MOLECULE TYPE: cDNA to mRNA
```

(iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 1..437

(xi) SEQUENCE DESCRIPTION: SEQ ID NO: 31:

```
GTTGTACTAT CATNGAAGAT TAAGTTAGTC GATGTTCCGT CCACGGTCAC CGNGTTTAAA        60

GTCCAGAAAC ATNAGGAGAA AGAGGCCGTT AGGNTCATCA ACAAGTGGCA GTATGTTGC        120

GATAAGGTCC CTGAAGATCT TTTCATCAGC GCAACGTTGG NGAGATCAAA CGGAAACTC        180

GTGCAGGCTT TGTTTACTGG ACTCTATCTT GGNCCGGTGA ATAATNTCTT GGCCTTGAT        240

GAAGAAAAGT TTCCAGANTT AGGTCTTGAT ATCCAAGNCT GCACAGAGAT GAGTTGGGC        300

GAATCTGCAC TCTGGTNTNC TGNTTTCNCT AAAGGAGAGN CTCCTTGGGT GTTCCNCGC        360

GATCGGNAGC GGNCAATTTN TGGNCTTTCA AGGGGAAAGN CGGCTTTTTN CAAGAACCC        420

NTACCCGGGG TTCAATT                                                      437
```

(2) INFORMATION FOR SEQ ID NO: 32:

(i) SEQUENCE CHARACTERISTICS:
        (A) LENGTH: 441 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana (ix) FEATURE:
        (A) NAME/KEY: CDS
        (B) LOCATION: 1..441

(xi) SEQUENCE DESCRIPTION: SEQ ID NO: 32:

```
GCGGACCCTA TAGATCANNA TGTGCTACTG ANAGAAGAGG AAGCCAAGAA CAAGCCGGAG        60

ACAGATAAAT ATCTGAAATG GGNCGATANC GTTTACGAAT TTATGACNCC ATATGTTTC        120

AAATCTCCAA GAGGAGCTTA TGTCAATTTC AAGGATATGG ATTTGGGTAT GTATCTTGG        180

AAGAAGAAGA CAAAGTACGA GGAAGGAAAG AGTTGGGGAG TGAAGTATTT CAAGAACAA        240

TTCGAGAGAT TGGTGAGAGT GAAGACTAGG GTTGATCCAA CAGATTTCTT CTGCGATGA        300

CAGAGCATTC CTCTGGTGAA CAAAGTTACC TGAAGATATC ATTTGAAGTT TTTTATTAG        360

CCCTTTTCTC TGTGAAATCA TCTGTGCGTG TTGAATATTA TGCGTCAAGT GTGTAACTT        420

TGTGTGTGAT TGTGAATTGT G                                                 441
```

(2) INFORMATION FOR SEQ ID NO: 33:

(i) SEQUENCE CHARACTERISTICS:
        (A) LENGTH: 502 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (A) ORGANISM: Arabidopsis thaliana
    (B) STRAIN: ecotype Columbia (ix) FEATURE:
    (A) NAME/KEY: CDS
    (B) LOCATION: 2..502

(xi) SEQUENCE DESCRIPTION: SEQ ID NO: 33:

```
CTGGCTTAAC ACAACGTCGT TTTGGGCCAA TTACCCGGCG GGTACACCCA AGAGCATCCT      60

TCTAGATAGG CCTCCGACGA ATTCAGTGTC ATTTAAGAGT AAATCGGATT TTGTCAAAA      120

ACCAATACCC AAAAAAGGTT TAGAGAAGCT TTGGAAGACA ATGTTTAAAT TCAACAGTA      180

CGTCTCGTTG CAATTCAACC CTTACGGTGG AGTGATGGAC CGGATTCCGG CAACGGCCA      240

CGCTTTTCCT CATCGGAAAG GAAACTTGTT CAAGGTTCAA TACNCTACGA TGTGGTTTG      300

CGCAAACGCC ACACAGAGTA GCCNGGCTAT GATGAATGAG CTTTTTGAGG TGGCGGGAC      360

GTACGTGNGT CAAGTAAACC CGAGANANGG CTTCCTTTAA NTTCAGAGNC CATCGNTNT      420

NGGAGCAANN CCAAGTGGGG GGGNCCAACC GGGGGNTNAA ANCNNAGNTC TTNGGGGGC      480

CAGAATTTCC TTNGGGGAAT TT                                              502
```

(2) INFORMATION FOR SEQ ID NO: 34:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 2..400

(xi) SEQUENCE DESCRIPTION: SEQ ID NO: 34:

```
NGGGAATTGC NCGAGGNAAG TTGTACCCAA TTCCTGGACC ACCATTGGTT TCCCAAGAAN      60

CCCGAGACAA CCGTTTTTCA ATNACCGTGA TGTTGATTTG GGTATTAATT CTCATAATG      120

TAAAATCAGT AGTTATGTGG AAGGTAAACG TTACGGGAAG AAGTATTTCG CAGGTAATT      180

CGAGAGATTG GTGAAGATTA AGACGAGAGT TGATAGTGGT AATTTCTTTA GGAACGAAC      240

GAGTATTCCT GTGTTACCAT AAGTGTATTT ATTTGATTAT TGGTTAGTGA AATTTGTTG      300

TGTATAATGA TTATATGTCG TATTTTTATT TATTATTAGT AATTTATAAA GTTTGATAT      360

AAATACAAAT AGTATAATAA GATAGTTTCT TTTAGTAAAA                           400
```

(2) INFORMATION FOR SEQ ID NO: 35:

(i) SEQUENCE CHARACTERISTICS:
        (A) LENGTH: 383 base pairs (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 2..383

(xi) SEQUENCE DESCRIPTION: SEQ ID NO: 35:

| | | | | | |
|---|---|---|---|---|---|
| CAACTCTAAT | GGGAACACCT | ACTTCGATCG | AATGTCGATG | GGGGAAGAGC | TTTTCTGGGC | 60 |
| GGTTCGAGGA | GGTGGAGCCG | CGAGTTTCGG | CATCGTGATG | GGATACAAAA | TCCGGTTGG | 120 |
| TCCGGTTCCG | GAGAAAGTTA | CGGTTTTTAG | CGTCGGAAAA | ACCGTCGGAG | AAGGAGCCG | 180 |
| TGATCTTATA | ATGAAGTGGC | AGAACTTCTC | TCATAGTACG | GNTCGGAATT | TNTTTGTGA | 240 |
| GCTGANTTTT | GANTTTAGTC | AACGGTGCAA | AGCCGGGTGA | AAAAAAGGTT | TTAGNGNCT | 300 |
| TCANTTTGGN | TGNAANCTTG | GGGGTTTTAT | NAGAACGGTT | AACCGGGATT | NANCCCGNG | 360 |
| TTTCCCGGGG | TTAAAACCTT | NGG | | | 383 |

(2) INFORMATION FOR SEQ ID NO: 36:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 1..354

(xi) SEQUENCE DESCRIPTION: SEQ ID NO: 36:

| | | | | | |
|---|---|---|---|---|---|
| ATCAATGTTC | TTACTAAACG | TACACGAGCA | TCGTTGGCTT | TCAAGGCTAA | ATCTGATTTT | 60 |
| NTTCAAGAAC | CGATNCCTAA | AACCGCGATT | TCGAAGCTTT | GGAGACGGTT | GCAAGAACC | 120 |
| GAAGCAGAGC | ATGCTCAGCT | AATTTNCACN | CCATTTGGTG | GTAAAATGAG | TNAGATTGC | 180 |
| GATTACGAAA | CACCATTTCC | GCATAGGAAG | GGGAATATAT | ATNAGATTCA | GTACTTGAA | 240 |
| TACTGGAGAG | GAGACGTGAA | AGAGAAGTAT | ATTGAGATNG | GTGGAGGAGA | GTTTACGGT | 300 |
| GNTATNAGTA | AGTTTTTTGG | CGAAGTNTNC | CNAGAGGNGN | CTTNNTNTAA | ACCT | 354 |

(2) INFORMATION FOR SEQ ID NO: 37:

(i) SEQUENCE CHARACTERISTICS:
        (A) LENGTH: 403 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: Arabidposis thaliana
             (B) STRAIN: ecotype Columbia (ix) FEATURE:
             (A) NAME/KEY: CDS
             (B) LOCATION: 2..403

(xi) SEQUENCE DESCRIPTION: SEQ ID NO: 37:

TTTTTTAGTA CACTAATAAT CAAATGGAAT GAGAAATGAA GCCACAAAAG TATCTGCAAT        60

CAAAATATCC TGCTATCTCC ATCTCAAGCT CTCAATAGTA TCCTCTCCGA AAGTGAAAT        120

AACATTTCAA ACTCTATTTC TTGGTGGAAT CGATAGACTG ATTCCTCTGA TGAACCAGA       180

GTTTCCGGAA CTCGGCTTAC GATCTCAAGA CTGTTCGGAA ATGAGCTGGA TCGAATCGA       240

AATGTTCTTC AACTGGAGAT CAGGACAGCC GTTAGAGATT TTGCTCAACA GAGACCTAA       300

GATTCGAGGA TCAGTATTTC AAAGCAAAGT CAGGATTATG GTTCAAAAAC CCGTTCCTG       360

AAACGTTTTT CGAAGAGGTA TCCAAGGGGT TTCTCGAGCA AGT                        403

(2) INFORMATION FOR SEQ ID NO: 38:

(i) SEQUENCE CHARACTERISTICS:
             (A) LENGTH: 260 base pairs
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: Arabidopsis thaliana
             (B) STRAIN: ecotype Columbia (ix) FEATURE:
             (A) NAME/KEY: CDS
             (B) LOCATION: 1..260

(xi) SEQUENCE DESCRIPTION: SEQ ID NO: 38:

GAGATGAGTT GGATTAANTC TGTACTCTGG TTTGCTGATT TCCCTAAAGG AGAATCTCTT        60

NGTGTTCTCA CGAATCGTAA GCGTACATCT CTATCTTTNA AAGGCAAAGA TGATTTTAT      120

CAAGAACCGA TACCCGAGGC TGCAATTNAA GAGATATGGA GGCGATTAGA AGCCCCCNA       180

GCTCGGCTTG GAAAGATCAT ATTAACTCCA TTTGGTGGGA AAATNAGTGA AATGGCAGA       240

TACGTANCAC CATTCCCACA                                                  260

(2) INFORMATION FOR SEQ ID NO: 39:

(i) SEQUENCE CHARACTERISTICS:
             (A) LENGTH: 605 base pairs
             (B) TYPE: nucleic acid
             (C) STRANDEDNESS: double
             (D) TOPOLOGY: linear (ii) MOLECULE TYPE: cDNA to mRNA (iii) HYPOTHETICAL: NO

```
    (iv) ANTI-SENSE: NO (vi) ORIGINAL SOURCE:
         (A) ORGANISM: Arabidopsis thaliana
         (B) STRAIN: ecotype Columbia (ix) FEATURE:
         (A) NAME/KEY: CDS
         (B) LOCATION: 2..605

(xi) SEQUENCE DESCRIPTION: SEQ ID NO: 39:

CTCTTGCATA TTCGCTGCAA GGATGGGAAA TTCAAAACCA CTCCCTACAA TTTTTTGTAT      60

TATAGTTTCA GTCTTGTATT TTTAATTCTA TTGCATAACA CCAACTTCTT CATCAGCCT      120

CATCCAAGAT CAATTCATAA ACTGTGTCAA AAGAAACACA CATGTTTCTT TTCCACTCG      180

GAAAACGTTA TTCACCCCTG CGAAAAACGT CTCTTTGTTC AACCAAGTCC TTGANTCGA      240

GGCTCAAAAT CTCCAGTTCT TGGCAAAATC CATGCCTAAA CCGGGRTTCA TATTCAGAC      300

GATTCACCAG TCTCAAGTCC AAGSTTCCAT CATTTGTTCA AMGRAACTCG GGNTTCATT      360

TNGTGTTTGA NGTGGCGGTC ACGATTTTCG AGGCCTTTGT NTTTATGTTT CACGGTTTG      420

AAAAACCGTT TATATTACTC GGCCTGTCAA ANTTGNANNC AAAATCANAT GTTGGATAT      480

GNATTCCAAA TAGGTNCTTG GGGTNAACCT GGTGGCTANC GTTTGGTGAG CTTTTACTT      540

CAAGAATTTG CANGNGGANG TGCAAAGATT CCATGGGATT TCCCGGGGGG TTTNTTGCA      600

AATGT                                                                 605

(2) INFORMATION FOR SEQ ID NO: 40:

(i) SEQUENCE CHARACTERISTICS:
        (A) LENGTH: 464 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (A) ORGANISM: Arabidopsis thaliana
         (B) STRAIN: ecotype Columbia (ix) FEATURE:
         (A) NAME/KEY: CDS
         (B) LOCATION: 2..464

(xi) SEQUENCE DESCRIPTION: SEQ ID NO: 40:

AACACAAAAC TCTTCCATTT GGCTTCTCTC TTGCATATTC GTTGCAAGGA TGGGAAATTC      60

AAAACCACTC CCTACAATTN CTTGTATTAT CGTTTCAGTC TTGTATTTTN NATTCTATT     120

CATAACACCA ACTTCTTCAT CAGCCTCCAT CCAAGNTCAA TTCATAAACT GTGTCAAAA     180

GAACACACAT GTTTCTTTTC CACTCGAGNA AACGGTATTC ACTCCTGCGG AAAACGGCT     240

TNTTATTCAA CGGGTCCNTG AATCGACGGG TCAAAATCTC CAGTTCTTGG NAAAATCCA     300

GNCTAAACCG GGGTTCATAT TCAGGCCGGT TCACCAGTCT CAAGTCCAAG NTTCCATCA     360

TTGTTCAAAG GAACTCGGGA TTCATTTCCG CGNTAGAAGT GGCGGGCANN GGTTTCGGG     420

CCTGTCTNTT GNTTANGGGN AGGAAAACCG GTTNTATTNC TCGG                     464

(2) INFORMATION FOR SEQ ID NO: 41:

(i) SEQUENCE CHARACTERISTICS:
```

```
        (A) LENGTH: 386 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 1..386

(xi) SEQUENCE DESCRIPTION: SEQ ID NO: 41:

TCGGGAGCCC ANGNTAAATT ANNTGAAAAT GGGGNCGNAT ANCCGTTTAC NGAATTTTAT      60

GACNCCCAAT ATGTTTCGAA ATCTCAAAGA NNGGGANCTT ATGTCAATTT CAAGGATAT     120

GATTTGGGTA TGTATCTTGG AAAGNAGAAG ACAAAGTACG AGGAAGGAAA GAGTTGGGG     180

GTGAAGTATT TCAAGAACAA TTTCGAGAGA TTGGTGAGAG TGAAGACTAG GGTTGATCC     240

ACAGATTTCN TCTGCGATGA ACAGAGCATT CCTCTGGTGN ACAAAGTTAC CTGAAGATA     300

CATTTGAAGT TTTTTATTAG TCCCTTTTCT CTGTGAAATC ATCTGTGCGT GTTGAATAN     360

ATGCGTCAAG TGTGTAACTT ATGTGT                                        386

(2) INFORMATION FOR SEQ ID NO: 42:

(i) SEQUENCE CHARACTERISTICS:
        (A) LENGTH: 377 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 1..377

(xi) SEQUENCE DESCRIPTION: SEQ ID NO: 42:

TACCATAGGG AGGTGGTGNA AGATTTTGTA TGTAGNCTTA GGGGAAGGCG AGTAGTATGG      60

TGGTGGTGGG GAGCTGTAAA CGTATGGTGG TGGTGGAGAT TTGTATGTGG GCTGGTTAA     120

TTCATTGAAG CTAAAATCTG GGGACCTAAG TACTTCAAAG GCAATTTTGA CAGATTGGT     180

AAGATTAAAA CCAAGGTTGA TCCAGAGAAC TTCTTCAGGC ACGAGCAGAG TATCCCACC     240

ATGCCCTACT AGAAGCTAGG TTCATGAAAC CAATAACATT ATCAAAAATA AGAATAAAT     300

ATAATTGTAT ACAACATGAT TCGTCTTTCT TTATTTCAGA CAATGTGGAC ACTACTCTA     360

ATAAAATGTC ATTTACC                                                  377

(2) INFORMATION FOR SEQ ID NO: 43:

(i) SEQUENCE CHARACTERISTICS:
        (A) LENGTH: 377 base pairs
```

(B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 1..377

(xi) SEQUENCE DESCRIPTION: SEQ ID NO: 43:

```
TACCATAGGG AGGTGGTGNA AGATTTTGTA TGTAGNCTTA GGGGAAGGCG AGTAGTATGG      60

TGGTGGTGGG GAGCTGTAAA CGTATGGTGG TGGTGGAGAT TTGTATGTGG GCTGGTTAA      120

TTCATTGAAG CTAAAATCTG GGACCTAAG TACTTCAAAG GCAATTTTGA CAGATTGGT      180

AAGATTAAAA CCAAGGTTGA TCCAGAGAAC TTCTTCAGGC ACGAGCAGAG TATCCCACC      240

ATGCCCTACT AGAAGCTAGG TTCATGAAAC CAATAACATT ATCAAAAATA AGAATAAAT      300

ATAATTGTAT ACAACATGAT TCGTCTTTCT TTATTTCAGA CAATGTGGAC ACTACTCTA      360

ATAAAATGTC ATTTACC                                                    377
```

(2) INFORMATION FOR SEQ ID NO: 44:

(i) SEQUENCE CHARACTERISTICS:
        (A) LENGTH: 346 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: ecotype Columbia (ix) FEATURE:
        (A) NAME/KEY: CDS
        (B) LOCATION: 2..346

(xi) SEQUENCE DESCRIPTION: SEQ ID NO: 44:

```
GAGCTGTGGA TATGGTCACA AATGGCAATC GGTTGGTCCG AAAACTGATC CGAATCTTTT      60

TATGAGAATN TTGATTCAAC CAGTGACGAG GAAGAAGGTA AAGACTGTGA GAGCTTCTN      120

GGTTGCCCTN TTTTNAGGCN AGACAGATGA AGTTTTTGCT TTCCTTAGTA AGGAGTTTC      180

TGAATTGGGT TTAAAGAAGG AGAATTNTTC GGAGATGACT TGGTTTCANT CTGCTTTAT      240

GTGGACAAT CGTCTTAATG CTACTCAGGT TGATCCTAAA GTNTTTCTTG ATCGGAATC      300

CGATACCTCG AGTTTCGGTA AGAGGAAATC GGATTACGTC GCGACT                   346
```

(2) INFORMATION FOR SEQ ID NO: 45:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: Arabidopsis thaliana
             (B) STRAIN: ecotype Columbia (ix) FEATURE:
             (A) NAME/KEY: CDS
             (B) LOCATION: 2..261

(xi) SEQUENCE DESCRIPTION: SEQ ID NO: 45:

```
ATGGGGTGAG ACTTATTTCA AAGGTAATTT CAAGAGATTA GGTTTGGTTA AAGGGAAGNT      60

TGATCCAACA AATTTCTTCA GGAACGAACA GAGTATTCCT CCTCTGTTTT GAGTCCTCA       120

TACAAAACCA GATATAAAAG ATGTCATTTC ATTTTTTCAA TTATAATAGA TAATGTAAC       180

TTCTGCTACA ATTGTAAAAG TGAGATGTAC CCAATACGGT TTAAGCGGAC CGAGAATAG       240

CAATTCAAAG ACCAAATTCT G                                                261
```

(2) INFORMATION FOR SEQ ID NO: 46:

(i) SEQUENCE CHARACTERISTICS:
             (A) LENGTH: 478 base pairs
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: Arabidopsis thaliana
             (B) STRAIN: ecotype Columbia (ix) FEATURE:
             (A) NAME/KEY: CDS
             (B) LOCATION: 1..478

(xi) SEQUENCE DESCRIPTION: SEQ ID NO: 46:

```
GCTCAAAGGA CTAACCATGA AAACTTCCTC AAGTGTCTCT CTCACCGANT CAACGAGGAC      60

GACTCAAGAN TTATACACAC ATCAAAAGAT CCTTCGTATT TNTCAATCTT GATTTCTTC       120

ATACAAAATC CAAGTTTCTC TGTTCTCGAA ACACCTAAAC CGGTTTCAAT CATCACTCC       180

GTTCAAGCCA CCGATGTTCA ATCTACGNTT AAATNCGCAC GGNCTTCACG GGTATACAC      240

ATCAGGGCTA GGAGTGGTNG TCATGACTAC GGAGGTTTAT CTTTACATTG GCTTAAAAA     300

CANNCCGTTC GTTNNTCATT GATTTNNAGA AATCTTCCGG GCTTATTTAA CATNTAAGA      360

GTTTGATAAN CCGGNNCCNG TTTGGGGTTC AAATCCCGGT GGCTTACAAA NTTNGGGGG     420

ATTGTNCCTA TGAGGTTTGG AAAATTAANG CAAAATNTTT TGGGCCTTCC CGGCCGGT      478
```

(2) INFORMATION FOR SEQ ID NO: 47:

(i) SEQUENCE CHARACTERISTICS:
             (A) LENGTH: 579 base pairs
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Arabidopsis thaliana
            (B) STRAIN: ecotype Columbia (ix) FEATURE:
            (A) NAME/KEY: CDS
            (B) LOCATION: 2..579

(xi) SEQUENCE DESCRIPTION: SEQ ID NO: 47:

GGCCGTTAGG ATCATCAAGA AATGGCAATA TGCTGCAGAT AAGGTTCCTG ATGATCTTTT      60

CATTAGGACA ACATTGGAGA GATCAAACAA GAACGCAGTA CACGCTTTGT TCACTGGAC      120

ATATATTGGT CCGGTGAACA ATCTATTGGC GTTGATGGAA GAAAAGTTTC CGGAACTAG      180

TCTTGAGAAA GAAGGTTGTG AAGAGATGAG TTGGATTGAG TCTGTACTCT GGTTTGCTG      240

TTTCCCTAAA GGAGAATCTC TTGGTGTTCT CACGAATCGT GAGCGTACAT CTCTATCTT      300

CAAAGGCAAA GATGATTTTG TCCAAGAACC GATACCCGAG GCTGCAATTC AAGAGATAT      360

GAGGCGATTA GAAGCCCCCG AGGCTCGGCT TGGAAAGATC ATATTAACTC CATTTGGGT      420

NGGNAAAATG AGTGAAATGG CAGAGNCCGA ACCACCAATT CCCACANNCG AGGGAGGGG      480

ACCCCTNTGN GGNTCAGAAT GTGGTTCCTG GNNNNNAAGN GGGNGCCAGN ACCAANCCG      540

GNCNGTAAAN CNTGNAATGG GCCNAACCCG TNCCGGATT                           579

(2) INFORMATION FOR SEQ ID NO: 48:

(i) SEQUENCE CHARACTERISTICS:
            (A) LENGTH: 252 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Oryza sativa
            (B) STRAIN: Nipponbare, subsp. japonica
            (D) DEVELOPMENTAL STAGE: etiolated shoot (8 days old)

(ix) FEATURE:
            (A) NAME/KEY: CDS
            (B) LOCATION: 3..252

(xi) SEQUENCE DESCRIPTION: SEQ ID NO: 48:

TGTCCTGGAA GGTCCGCCTC GTGCAGGTTN CGACGACGGT GACGGTGTTC GTCGTCGGGA      60

GGAACGTCGA CCAGGGCGCC GCNGACGTCG TCGCCAGATG GCAAGACGTC GCGCCGAGC      120

TCCCTCCCGA GCTCACCATA CGGGTGATCG TNCGAGGGCA GCGCGCCACG TTCCAGTCG      180

TGTACCTCGG CTCGTGCGCC GACCTGGTGC CGACGATGAG CAGCATGTTC CCGGAGCTC      240

GGATGACGAT TG                                                        252

(2) INFORMATION FOR SEQ ID NO: 49:

(i) SEQUENCE CHARACTERISTICS:
            (A) LENGTH: 21 amino acids
            (B) TYPE: amino acid
            (C) STRANDEDNESS: single
            (D) TOPOLOGY: linear

```
    (ii) MOLECULE TYPE: protein (iii) HYPOTHETICAL: NO (vi) ORIGINAL SOURCE:
         (A) ORGANISM: Lactuca sativa
         (B) STRAIN: lollo bionda (ix) FEATURE:
         (A) NAME/KEY: Modified-site
         (B) LOCATION: 12
         (D) OTHER INFORMATION: /label= Ambiguous
             /note= "Xaa = Cys or Ser"

(ix) FEATURE:
         (A) NAME/KEY: Modified-site
         (B) LOCATION: 20..21
         (D) OTHER INFORMATION: /label= ambiguous
             /note= "Xaa-Xaa probably is Ser-Phe"

(xi) SEQUENCE DESCRIPTION: SEQ ID NO: 49:

Thr Ser Thr Ser Ile Ile Asp Arg Phe Thr Gln Xaa Leu Asn Asn Arg
1               5                   10                  15

Ala Asp Pro Xaa Xaa
            20

(2) INFORMATION FOR SEQ ID NO: 50:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: protein (iii) HYPOTHETICAL: NO (vi) ORIGINAL SOURCE:
         (A) ORGANISM: Lactuca sativa
         (B) STRAIN: lollo bionda (ix) FEATURE:
         (A) NAME/KEY: Modified-site
         (B) LOCATION: 1
         (D) OTHER INFORMATION: /label= ambiguous
             /note= "Xaa = probably Ser"

(ix) FEATURE:
         (A) NAME/KEY: Modified-site
         (B) LOCATION: 3
         (D) OTHER INFORMATION: /label= unknown (ix) FEATURE:
         (A) NAME/KEY: Modified-site
         (B) LOCATION: 5
         (D) OTHER INFORMATION: /label= ambiguous
             /note= "Xaa = probably Ser"

(ix) FEATURE:
         (A) NAME/KEY: Modified-site
         (B) LOCATION: 12
         (D) OTHER INFORMATION: /label= ambiguous
             /note= "Xaa = probably Trp"

(ix) FEATURE:
         (A) NAME/KEY: Modified-site
         (B) LOCATION: 24
         (D) OTHER INFORMATION: /label= ambiguous
             /note= "Xaa = probably Tyr"

(xi) SEQUENCE DESCRIPTION: SEQ ID NO: 50:

Xaa Ile Xaa Val Xaa Ile Glu Asp Glu Thr Ala Xaa Val Gln Ala Gly
1               5                   10                  15
```

```
Ala Thr Leu Gly Glu Val Tyr Xaa
            20
```

(2) INFORMATION FOR SEQ ID NO: 51:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Lactuca sativa
        (B) STRAIN: lollo bionda (xi) SEQUENCE DESCRIPTION: SEQ ID NO: 51:

```
Ala Asp Pro Ser Phe Pro Leu Ser Gly Gln Leu Tyr Tyr Pro
 1               5                  10
```

(2) INFORMATION FOR SEQ ID NO: 52:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 52:

```
ACTTCTACTT CTATTATTGA TAGGTTTACT CA                                 32
```

(2) INFORMATION FOR SEQ ID NO: 53:

(i) SEQUENCE CHARACTERISTICS:
        (A) LENGTH: 405 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Lactuca sativa
        (B) STRAIN: lollo bionda (ix) FEATURE:
        (A) NAME/KEY: CDS
        (B) LOCATION: 1..405

(xi) SEQUENCE DESCRIPTION: SEQ ID NO: 53:

```
ACT TCT ACT TCT ATT ATT GAT AGG TTT ACT CAA TGT CTA AAC AAC CGA        48
Thr Ser Thr Ser Ile Ile Asp Arg Phe Thr Gln Cys Leu Asn Asn Arg
 1               5                  10                  15

GCT GAC CCT TCT TTC CCG CTC AGT GGA CAA CTT TAC ACT CCC GAT AAC        96
Ala Asp Pro Ser Phe Pro Leu Ser Gly Gln Leu Tyr Thr Pro Asp Asn
                20                  25                  30

TCC TCT TTT CCA TCC GTC TTG CAA GCT TAC ATC CGG AAC CTC CGA TTC       144
Ser Ser Phe Pro Ser Val Leu Gln Ala Tyr Ile Arg Asn Leu Arg Phe
         35                  40                  45
```

```
AAT GAA TCC ACG ACT CCC AAA CCC ATC TTA ATC ATC ACC GCC TTA CAC       192
Asn Glu Ser Thr Thr Pro Lys Pro Ile Leu Ile Ile Thr Ala Leu His
 50                  55                  60

CCT TCA CAC ATT CAA GCA GCT GTT GTG TGC GCC AAA ACA CAC CGC CTG       240
Pro Ser His Ile Gln Ala Ala Val Val Cys Ala Lys Thr His Arg Leu
 65                  70                  75                  80

CTA ATG AAA ACC AGA AGC GGA GGC CAT GAT TAT GAG GGG CTT TCC TAT       288
Leu Met Lys Thr Arg Ser Gly Gly His Asp Tyr Glu Gly Leu Ser Tyr
                 85                  90                  95

GTG ACC AAT TCG AAC CAA CCC TTT TTT GTT GTT GAC ATG TTC AAC TTA       336
Val Thr Asn Ser Asn Gln Pro Phe Phe Val Val Asp Met Phe Asn Leu
                100                 105                 110

CGC TCC ATA AAC GTG AGT ATT GAA GAT GAA ACT GCA TGG GTC CAA GCC       384
Arg Ser Ile Asn Val Ser Ile Glu Asp Glu Thr Ala Trp Val Gln Ala
                115                 120                 125

GGC GCC ACC CTC GGA GAA GTT                                           405
Gly Ala Thr Leu Gly Glu Val
    130                 135
```

(2) INFORMATION FOR SEQ ID NO: 54:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 54:

```
Thr Ser Thr Ser Ile Ile Asp Arg Phe Thr Gln Cys Leu Asn Asn Arg
 1               5                  10                  15

Ala Asp Pro Ser Phe Pro Leu Ser Gly Gln Leu Tyr Thr Pro Asp Asn
                20                  25                  30

Ser Ser Phe Pro Ser Val Leu Gln Ala Tyr Ile Arg Asn Leu Arg Phe
                35                  40                  45

Asn Glu Ser Thr Thr Pro Lys Pro Ile Leu Ile Ile Thr Ala Leu His
 50                  55                  60

Pro Ser His Ile Gln Ala Ala Val Val Cys Ala Lys Thr His Arg Leu
 65                  70                  75                  80

Leu Met Lys Thr Arg Ser Gly Gly His Asp Tyr Glu Gly Leu Ser Tyr
                 85                  90                  95

Val Thr Asn Ser Asn Gln Pro Phe Phe Val Val Asp Met Phe Asn Leu
                100                 105                 110

Arg Ser Ile Asn Val Ser Ile Glu Asp Glu Thr Ala Trp Val Gln Ala
                115                 120                 125

Gly Ala Thr Leu Gly Glu Val
    130                 135
```

(2) INFORMATION FOR SEQ ID NO: 55:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 55:

```
CACGTTTATG GAGCGTAAGT TGAAC                                            25
```

(2) INFORMATION FOR SEQ ID NO: 56:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 56:

```
CACCCTTCAC ACATTCAAGC AGC                                          23
```

(2) INFORMATION FOR SEQ ID NO: 57:

(i) SEQUENCE CHARACTERISTICS:
        (A) LENGTH: 1981 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Lactuca sativa
        (B) STRAIN: lollo bionda (ix) FEATURE:
        (A) NAME/KEY: CDS
        (B) LOCATION: 7..1626

(ix) FEATURE:
        (A) NAME/KEY: unsure
        (B) LOCATION: replace(372, "g")

(ix) FEATURE:
        (A) NAME/KEY: unsure
        (B) LOCATION: replace(379, "g")

(ix) FEATURE:
        (A) NAME/KEY: unsure
        (B) LOCATION: replace(786, "t")

(ix) FEATURE:
        (A) NAME/KEY: unsure
        (B) LOCATION: replace(1105..1106, "ga")
        (D) OTHER INFORMATION: /note= "also possible "gg" and "aa""

(xi) SEQUENCE DESCRIPTION: SEQ ID NO: 57:

```
ACAAAA ATG GCA ATT ACC TAT TCT TTC AAC TTC AAA TCT TAT ATT TTT        48
       Met Ala Ile Thr Tyr Ser Phe Asn Phe Lys Ser Tyr Ile Phe
        1               5                  10

CCT CTC CTC CTT GTC TTG CTC TCT ACC CAT TCA TCA GCG ACT TCA ACT        96
Pro Leu Leu Leu Val Leu Leu Ser Thr His Ser Ser Ala Thr Ser Thr
 15              20                  25                  30

TCC ATT ATA GAT CGC TTC ACC CAA TGT CTA AAC AAC CGA GCT GAC CCT       144
Ser Ile Ile Asp Arg Phe Thr Gln Cys Leu Asn Asn Arg Ala Asp Pro
                35                  40                  45

TCT TTC CCG CTC AGT GGA CAA CTT TAC ACT CCC GAT AAC TCC TCT TTT       192
Ser Phe Pro Leu Ser Gly Gln Leu Tyr Thr Pro Asp Asn Ser Ser Phe
             50                  55                  60

CCA TCC GTC TTG CAA GCT TAC ATC CGG AAC CTC CGA TTC AAT GAA TCC       240
Pro Ser Val Leu Gln Ala Tyr Ile Arg Asn Leu Arg Phe Asn Glu Ser
 65                  70                  75
```

-continued

```
ACG ACT CCC AAA CCC ATC TTA ATC ATC ACC GCC TTA CAC CCT TCA CAC      288
Thr Thr Pro Lys Pro Ile Leu Ile Ile Thr Ala Leu His Pro Ser His
     80              85                  90

ATT CAA GCA GCT GTT GTG TGC GCC AAA ACA CAC CGC CTG CTA ATG AAA      336
Ile Gln Ala Ala Val Val Cys Ala Lys Thr His Arg Leu Leu Met Lys
 95             100                 105                 110

ACC AGA AGC GGA GGC CAT GAT TAT GAG GGG CTT TCC TAT GTG ACC AAT      384
Thr Arg Ser Gly Gly His Asp Tyr Glu Gly Leu Ser Tyr Val Thr Asn
                115                 120                 125

TCG AAC CAA CCC TTT TTT GTT GTT GAC ATG TTC AAC TTA CGC TCC ATA      432
Ser Asn Gln Pro Phe Phe Val Val Asp Met Phe Asn Leu Arg Ser Ile
         130                 135                 140

AAC GTG AGT ATT GAA GAT GAA ACT GCA TGG GTC CAA GCT GGT GCG ACT      480
Asn Val Ser Ile Glu Asp Glu Thr Ala Trp Val Gln Ala Gly Ala Thr
             145                 150                 155

CTT GGT GAA GTC TAC TAC CGA ATA GCA GAG AAA AGC AAC AGT CAT GCT      528
Leu Gly Glu Val Tyr Tyr Arg Ile Ala Glu Lys Ser Asn Ser His Ala
        160                 165                 170

TTT CCG GCT GGC GTT TGC CCT ACT GTT GGA GTT GGT GGC CAT TTT AGT      576
Phe Pro Ala Gly Val Cys Pro Thr Val Gly Val Gly Gly His Phe Ser
175             180                 185                     190

GGT GGT GGT TAT GGT AAC TTG ATG GGA AAA TAC GGC CTT TCT GTT GAC      624
Gly Gly Gly Tyr Gly Asn Leu Met Gly Lys Tyr Gly Leu Ser Val Asp
                195                 200                 205

AAT ATT GTC GAT GCT CAG TTA ATC GAT GTG AAT GGT AAA CTT CTG AAT      672
Asn Ile Val Asp Ala Gln Leu Ile Asp Val Asn Gly Lys Leu Leu Asn
            210                 215                 220

CGG AAA TCA ATG GGT GAA GAT CTT TTT TGG GCC ATC ACA GGT GGT GGT      720
Arg Lys Ser Met Gly Glu Asp Leu Phe Trp Ala Ile Thr Gly Gly Gly
        225                 230                 235

GGT GTC AGC TTT GGT GTG GTT GTA GCG TAC AAG ATC AAA CTG GTT CGT      768
Gly Val Ser Phe Gly Val Val Val Ala Tyr Lys Ile Lys Leu Val Arg
    240                 245                 250

GTT CCT ACC ACT GTG ACC GTT TTT AAC GTA CAA AGA ACA TCC GAG CAG      816
Val Pro Thr Thr Val Thr Val Phe Asn Val Gln Arg Thr Ser Glu Gln
255             260                 265                 270

AAC CTA AGC ACC ATA GCC CAC CGA TGG ATA CAA GTT GCG GAT AAG CTC      864
Asn Leu Ser Thr Ile Ala His Arg Trp Ile Gln Val Ala Asp Lys Leu
                275                 280                 285

GAT AAT GAC CTT TTC CTT CGA ATG ACC TTT AAC GTG ATA AAC AAC ACA      912
Asp Asn Asp Leu Phe Leu Arg Met Thr Phe Asn Val Ile Asn Asn Thr
            290                 295                 300

AAT GGC GAA AAG ACG ATA CGT GGT TTG TTT CCA ACA CTG TAC CTC GGA      960
Asn Gly Glu Lys Thr Ile Arg Gly Leu Phe Pro Thr Leu Tyr Leu Gly
        305                 310                 315

AAC TCT ACC GCT CTT GTT GCC CTC CTG AAC AAG GAT TTC CCT GAA TTA     1008
Asn Ser Thr Ala Leu Val Ala Leu Leu Asn Lys Asp Phe Pro Glu Leu
    320                 325                 330

GGT GTA GAA ATT TCA GAT TGT ATT GAA ATG AGT TGG ATC GAG TCT GTT     1056
Gly Val Glu Ile Ser Asp Cys Ile Glu Met Ser Trp Ile Glu Ser Val
335             340                 345                 350

CTT TTC TAC ACA AAC TTC CCC ATT GGT ACT CCG ACC ACT GCT CTT CTA     1104
Leu Phe Tyr Thr Asn Phe Pro Ile Gly Thr Pro Thr Thr Ala Leu Leu
                355                 360                 365

AGC CGT ACA CCT CAA AGA CTA AAC CCA TTC AAA ATC AAA TCT GAT TAC     1152
Ser Arg Thr Pro Gln Arg Leu Asn Pro Phe Lys Ile Lys Ser Asp Tyr
            370                 375                 380

GTA AAA AAC ACT ATT TCC AAA CAG GGA TTC GAA TCC ATA TTT GAA AGG     1200
Val Lys Asn Thr Ile Ser Lys Gln Gly Phe Glu Ser Ile Phe Glu Arg
```

```
                385                 390                 395
ATG AAA GAA CTC GAA AAC CAA ATG CTA GCT TTC AAC CCT TAT GGT GGA    1248
Met Lys Glu Leu Glu Asn Gln Met Leu Ala Phe Asn Pro Tyr Gly Gly
    400                 405                 410

AGA ATG AGC GAA ATT TCC GAA TTT GCA AAG CCT TTT CCC CAT CGA TCA    1296
Arg Met Ser Glu Ile Ser Glu Phe Ala Lys Pro Phe Pro His Arg Ser
415                 420                 425                 430

GGG AAT ATA GCG AAG ATC CAA TAC GAA GTA AAC TGG GAT GAA CTT GGC    1344
Gly Asn Ile Ala Lys Ile Gln Tyr Glu Val Asn Trp Asp Glu Leu Gly
                435                 440                 445

GTT GAA GCA GCC AAT CGG TAC TTG AAC TTC ACA AGG GTG ATG TAT GAT    1392
Val Glu Ala Ala Asn Arg Tyr Leu Asn Phe Thr Arg Val Met Tyr Asp
        450                 455                 460

TAT ATG ACT CCG TTT GTT TCT AAG AAC CCC AGG GAA GCA TTT CTG AAC    1440
Tyr Met Thr Pro Phe Val Ser Lys Asn Pro Arg Glu Ala Phe Leu Asn
            465                 470                 475

TAC AGG GAT TTA GAT ATT GGT GTC AAC AGT CAT GGC AAG AAT GCT TAC    1488
Tyr Arg Asp Leu Asp Ile Gly Val Asn Ser His Gly Lys Asn Ala Tyr
480                 485                 490

GGT GAA GGA ATG GTT TAT GGG CAC AAG TAT TTC AAA GAG ACG AAT TAT    1536
Gly Glu Gly Met Val Tyr Gly His Lys Tyr Phe Lys Glu Thr Asn Tyr
495                 500                 505                 510

AAG AGG CTA ACG ATG GTG AAG ACG AGG GTT GAT CCT AGC AAT TTT TTT    1584
Lys Arg Leu Thr Met Val Lys Thr Arg Val Asp Pro Ser Asn Phe Phe
                515                 520                 525

AGG AAT GAG CAA AGT ATC CCA ACT TTG TCA TCT TCA TGG AAG            1626
Arg Asn Glu Gln Ser Ile Pro Thr Leu Ser Ser Ser Trp Lys
                530                 535                 540

TAAATTCTAA ATTCACTTGT GAAATTGAAT AAAAGTATGG CTTTTTCAAG GTCATGGT    1686

CCAGATTCAG ATGATATTGA TATAATTTTG ACTTGTATTT ATACAAACAA AATTATAT    1746

TATTTTTCTG AATTTAGATT TTCCATTCTT TGGAAAAATA TACGAACATT GATGTTGA    1806

TTTTTAAGAA TTATAGATTT TGAACATTGT GAACAATGAA TAAACCGAGG ACTTCCCT    1866

GGTTTTTTTT ATAAGTATGT AATAGCATGT CTTTAATCAA GATAACCGAT CATTGGAT    1926

AATTTATTAT TATAAACCTT ATTTAAAAAA AAAAAAAAAA AAAAAAAAAA AAAAA       1981

(2) INFORMATION FOR SEQ ID NO: 58:

(i) SEQUENCE CHARACTERISTICS:
        (A) LENGTH: 540 amino acids
        (B) TYPE: amino acid
        (D) TOPOLOGY: linear (ii) MOLECULE TYPE: protein (xi) SEQUENCE DESCRIPTION: SEQ ID NO: 58:

Met Ala Ile Thr Tyr Ser Phe Asn Phe Lys Ser Tyr Ile Phe Pro Leu
 1               5                  10                  15

Leu Leu Val Leu Leu Ser Thr His Ser Ser Ala Thr Ser Thr Ser Ile
                20                  25                  30

Ile Asp Arg Phe Thr Gln Cys Leu Asn Asn Arg Ala Asp Pro Ser Phe
            35                  40                  45

Pro Leu Ser Gly Gln Leu Tyr Thr Pro Asp Asn Ser Ser Phe Pro Ser
        50                  55                  60

Val Leu Gln Ala Tyr Ile Arg Asn Leu Arg Phe Asn Glu Ser Thr Thr
65                  70                  75                  80

Pro Lys Pro Ile Leu Ile Thr Ala Leu His Pro Ser His Ile Gln
                85                  90                  95
```

-continued

```
Ala Ala Val Val Cys Ala Lys Thr His Arg Leu Leu Met Lys Thr Arg
            100                 105                 110

Ser Gly Gly His Asp Tyr Glu Gly Leu Ser Tyr Val Thr Asn Ser Asn
        115                 120                 125

Gln Pro Phe Phe Val Val Asp Met Phe Asn Leu Arg Ser Ile Asn Val
    130                 135                 140

Ser Ile Glu Asp Glu Thr Ala Trp Val Gln Ala Gly Thr Leu Gly
145                 150                 155                 160

Glu Val Tyr Tyr Arg Ile Ala Glu Lys Ser Asn Ser His Ala Phe Pro
                165                 170                 175

Ala Gly Val Cys Pro Thr Val Gly Val Gly His Phe Ser Gly Gly
            180                 185                 190

Gly Tyr Gly Asn Leu Met Gly Lys Tyr Gly Leu Ser Val Asp Asn Ile
        195                 200                 205

Val Asp Ala Gln Leu Ile Asp Val Asn Gly Lys Leu Leu Asn Arg Lys
    210                 215                 220

Ser Met Gly Glu Asp Leu Phe Trp Ala Ile Thr Gly Gly Gly Gly Val
225                 230                 235                 240

Ser Phe Gly Val Val Val Ala Tyr Lys Ile Lys Leu Val Arg Val Pro
                245                 250                 255

Thr Thr Val Thr Val Phe Asn Val Gln Arg Thr Ser Glu Gln Asn Leu
            260                 265                 270

Ser Thr Ile Ala His Arg Trp Ile Gln Val Ala Asp Lys Leu Asp Asn
        275                 280                 285

Asp Leu Phe Leu Arg Met Thr Phe Asn Val Ile Asn Asn Thr Asn Gly
    290                 295                 300

Glu Lys Thr Ile Arg Gly Leu Phe Pro Thr Leu Tyr Leu Gly Asn Ser
305                 310                 315                 320

Thr Ala Leu Val Ala Leu Leu Asn Lys Asp Phe Pro Glu Leu Gly Val
                325                 330                 335

Glu Ile Ser Asp Cys Ile Glu Met Ser Trp Ile Glu Ser Val Leu Phe
            340                 345                 350

Tyr Thr Asn Phe Pro Ile Gly Thr Pro Thr Thr Ala Leu Leu Ser Arg
        355                 360                 365

Thr Pro Gln Arg Leu Asn Pro Phe Lys Ile Lys Ser Asp Tyr Val Lys
    370                 375                 380

Asn Thr Ile Ser Lys Gln Gly Phe Glu Ser Ile Phe Glu Arg Met Lys
385                 390                 395                 400

Glu Leu Glu Asn Gln Met Leu Ala Phe Asn Pro Tyr Gly Gly Arg Met
                405                 410                 415

Ser Glu Ile Ser Glu Phe Ala Lys Pro Phe Pro His Arg Ser Gly Asn
            420                 425                 430

Ile Ala Lys Ile Gln Tyr Glu Val Asn Trp Asp Glu Leu Gly Val Glu
        435                 440                 445

Ala Ala Asn Arg Tyr Leu Asn Phe Thr Arg Val Met Tyr Asp Tyr Met
    450                 455                 460

Thr Pro Phe Val Ser Lys Asn Pro Arg Glu Ala Phe Leu Asn Tyr Arg
465                 470                 475                 480

Asp Leu Asp Ile Gly Val Asn Ser His Gly Lys Asn Ala Tyr Gly Glu
                485                 490                 495

Gly Met Val Tyr Gly His Lys Tyr Phe Lys Glu Thr Asn Tyr Lys Arg
            500                 505                 510
```

```
Leu Thr Met Val Lys Thr Arg Val Asp Pro Ser Asn Phe Phe Arg Asn
        515                 520                 525

Glu Gln Ser Ile Pro Thr Leu Ser Ser Ser Trp Lys
    530                 535                 540
```

(2) INFORMATION FOR SEQ ID NO: 59:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 59:

GGTAATGATC TCCTTTCTTG TTTGACC                                                    27

(2) INFORMATION FOR SEQ ID NO: 60:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 60:

AGAGCGGCCG CTATATTACA ACTTCTCCAC CATCACTCCT C                          41

(2) INFORMATION FOR SEQ ID NO: 61:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 61:

GGTGATGTTA ATGATAATCT CCTC                                                        24

(2) INFORMATION FOR SEQ ID NO: 62:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 62:

AGAGCGGCCG CTACAATTCC TTCAACATGT AAATTTCCTC                          40

(2) INFORMATION FOR SEQ ID NO: 63:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (xi) SEQUENCE DESCRIPTION: SEQ ID NO: 63:

ACTTCCCGTA GAAACTCGGA GACTTTCACA CAATGC                            36

(2) INFORMATION FOR SEQ ID NO: 64:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 64:

TCCATCCAAG ATCAATTCAT AAACTGTGTC                                   30

(2) INFORMATION FOR SEQ ID NO: 65:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 65:

AGAGCGGCCG CTTTCATGAA CCTAGCTTCT AGTAGG                            36

(2) INFORMATION FOR SEQ ID NO: 66:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 66:

AGAGCGGCCG CGAAATGGCC CCCCTTTTAA AACGGGG                           37

(2) INFORMATION FOR SEQ ID NO: 67:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 67:

AGAGCGGCCG CAAATGATAT CTTCAGGTAA CTTTGTTCAC    40

(2) INFORMATION FOR SEQ ID NO: 68:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 68:

AGAGCGGCCG CATAATCAAA TAAATACACT TATGGTAACA CAG    43

(2) INFORMATION FOR SEQ ID NO: 69:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 69:

AGAGCGGCCG CTGGTTTTGT ATTGAGGACT CAAAACAG    38

(2) INFORMATION FOR SEQ ID NO: 70:

(i) SEQUENCE CHARACTERISTICS:
        (A) LENGTH: 1757 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana
        (B) STRAIN: Colombia (ix) FEATURE:
        (A) NAME/KEY: CDS
        (B) LOCATION: join(1..570, 801..1754)

(xi) SEQUENCE DESCRIPTION: SEQ ID NO: 70:

```
ACT TCC CGT AGA AAC TCG GAG ACT TTC ACA CAA TGC CTA ACC TCA AAC      48
Thr Ser Arg Arg Asn Ser Glu Thr Phe Thr Gln Cys Leu Thr Ser Asn
 1               5                  10                  15

TCC GAC CCC AAA CAT CCC ATC TCC CCC GCT ATC TTC TTC TCC GGA AAT      96
Ser Asp Pro Lys His Pro Ile Ser Pro Ala Ile Phe Phe Ser Gly Asn
             20                  25                  30

GGC TCC TAC TCC TCC GTA TTA CAA GCC AAC ATC CGT AAC CTC CGC TTC     144
Gly Ser Tyr Ser Ser Val Leu Gln Ala Asn Ile Arg Asn Leu Arg Phe
         35                  40                  45

AAC ACC ACC TCA ACT CCG AAA CCC TTC CTC ATA ATC GCC GCA ACA CAT     192
Asn Thr Thr Ser Thr Pro Lys Pro Phe Leu Ile Ile Ala Ala Thr His
     50                  55                  60

GAA TCC CAT GTG CAA GCC GCG ATT ACT TGC GGG AAA CGC CAC AAC CTT     240
```

```
                                                    -continued

Glu Ser His Val Gln Ala Ala Ile Thr Cys Gly Lys Arg His Asn Leu
 65                  70                  75                  80

CAG ATG AAA ATC AGA AGT GGA GGC CAC GAC TAC GAT GGC TTG TCA TAC         288
Gln Met Lys Ile Arg Ser Gly Gly His Asp Tyr Asp Gly Leu Ser Tyr
                 85                  90                  95

GTT ACA TAC TCT GGC AAA CCG TTC TTC GTC CTC GAC ATG TTT AAC CTC         336
Val Thr Tyr Ser Gly Lys Pro Phe Phe Val Leu Asp Met Phe Asn Leu
                100                 105                 110

CGT TCG GTG GAT GTC GAT GTG GCA AGT AAG ACC GCG TGG GTC CAA ACC         384
Arg Ser Val Asp Val Asp Val Ala Ser Lys Thr Ala Trp Val Gln Thr
            115                 120                 125

GGT GCC ATA CTC GGA GAA GTT TAT TAC TAT ATA TGG GAG AAG AGC AAA         432
Gly Ala Ile Leu Gly Glu Val Tyr Tyr Tyr Ile Trp Glu Lys Ser Lys
        130                 135                 140

ACC CTA GCT TAT CCC GCC GGA ATT TGT CCC ACG GTT GGT GTC GGT GGC         480
Thr Leu Ala Tyr Pro Ala Gly Ile Cys Pro Thr Val Gly Val Gly Gly
145                 150                 155                 160

CAT ATC AGT GGT GGA GGT TAC GGT AAC ATG ATG AGA AAA TAC GGT CTC         528
His Ile Ser Gly Gly Gly Tyr Gly Asn Met Met Arg Lys Tyr Gly Leu
                165                 170                 175

ACC GTA GAT AAT ACC ATC GAT GCA AGA ATG GTC GAC GTT AAT                 570
Thr Val Asp Asn Thr Ile Asp Ala Arg Met Val Asp Val Asn
            180                 185                 190

GGTATAATTG ATATCTCTAT TTTATATACT AATTAAATTT TATAGTGTGG ATCGGATAG        630

GATTTTGGTC CATCAATTAA AAACTTGGTG AACATAAAAT TAACCAAGCA ATCAATTTA        690

ACAAGCAACA TAATCATATA TATTTTTCTT ACATTTGTAT GTACCTGAAT ATTTATATT        750

ATGTTTATAT GTTCTCACTA TATTTTCACT TTTGTATTTG AAAATTTTTA GGA AAA          806
                                                        Gly Lys
ATT TTG GAT AGA AAA TTG ATG GGA GAA GAT CTC TAC TGG GCA ATA AAC         854
Ile Leu Asp Arg Lys Leu Met Gly Glu Asp Leu Tyr Trp Ala Ile Asn
            195                 200                 205

GGA GGA GGA GGA GGG AGC TAC GGC GTC GTA TTG GCC TAC AAA ATA AAC         902
Gly Gly Gly Gly Gly Ser Tyr Gly Val Val Leu Ala Tyr Lys Ile Asn
        210                 215                 220

CTT GTT GAA GTC CCA GAA AAC GTC ACC GTT TTC AGA ATC TCC CGG ACG         950
Leu Val Glu Val Pro Glu Asn Val Thr Val Phe Arg Ile Ser Arg Thr
225                 230                 235                 240

TTA GAA CAA AAT GCG ACG GAT ATC ATT CAC CGG TGG CAA CAA GTT GCA         998
Leu Glu Gln Asn Ala Thr Asp Ile Ile His Arg Trp Gln Gln Val Ala
                245                 250                 255

CCG AAG CTT CCC GAC GAG CTT TTC ATA AGA ACA GTC ATT GAC GTA GTA        1046
Pro Lys Leu Pro Asp Glu Leu Phe Ile Arg Thr Val Ile Asp Val Val
            260                 265                 270

AAC GGC ACT GTT TCA TCT CAA AAG ACC GTC AGG ACA ACA TTC ATA GCA        1094
Asn Gly Thr Val Ser Ser Gln Lys Thr Val Arg Thr Thr Phe Ile Ala
        275                 280                 285

ATG TTT CTA GGA GAC ACG ACA ACT CTA CTG TCG ATA TTA AAC CGG AGA        1142
Met Phe Leu Gly Asp Thr Thr Thr Leu Leu Ser Ile Leu Asn Arg Arg
290                 295                 300

TTC CCA GAA TTG GGT TTG GTC CGG TCT GAC TGT ACC GAA ACA AGC TGG        1190
Phe Pro Glu Leu Gly Leu Val Arg Ser Asp Cys Thr Glu Thr Ser Trp
305                 310                 315                 320

ATC CAA TCT GTG CTA TTC TGG ACA AAT ATC CAA GTT GGT TCG TCG GAG        1238
Ile Gln Ser Val Leu Phe Trp Thr Asn Ile Gln Val Gly Ser Ser Glu
                325                 330                 335

ACA CTT CTA CTC CAA AGG AAT CAA CCC GTG AAC TAC CTC AAG AGG AAA        1286
Thr Leu Leu Leu Gln Arg Asn Gln Pro Val Asn Tyr Leu Lys Arg Lys
            340                 345                 350
```

-continued

```
TCA GAT TAC GTA CGT GAA CCG ATT TCA AGA ACC GGT TTA GAG TCA ATT         1334
Ser Asp Tyr Val Arg Glu Pro Ile Ser Arg Thr Gly Leu Glu Ser Ile
        355                 360                 365

TGG AAG AAA ATG ATC GAG CTT GAA ATT CCG ACA ATG GCT TTC AAT CCA         1382
Trp Lys Lys Met Ile Glu Leu Glu Ile Pro Thr Met Ala Phe Asn Pro
370                 375                 380

TAC GGT GGT GAG ATG GGG AGG ATA TCA TTA CGG GTG ACT CCG TTC CCA         1430
Tyr Gly Gly Glu Met Gly Arg Ile Ser Leu Arg Val Thr Pro Phe Pro
385                 390                 395                 400

TAC AGA GCC GGT AAT CTC TGG AAG ATT CAG TAC GGT GCG AAT TGG AGA         1478
Tyr Arg Ala Gly Asn Leu Trp Lys Ile Gln Tyr Gly Ala Asn Trp Arg
                405                 410                 415

GAT GAG ACT TTA ACC GAC CGG TAC ATG GAA TTG ACG AGG AAG TTG TAC         1526
Asp Glu Thr Leu Thr Asp Arg Tyr Met Glu Leu Thr Arg Lys Leu Tyr
        420                 425                 430

CAA TTC ATG ACA CCA TTT GTT TCC AAG AAT CCG AGA CAA TCG TTT TTC         1574
Gln Phe Met Thr Pro Phe Val Ser Lys Asn Pro Arg Gln Ser Phe Phe
        435                 440                 445

AAT AAC CGT GAT GTT GAT TTG GGT ATT AAT TCT CAT AAT GGT AAA ATC         1622
Asn Asn Arg Asp Val Asp Leu Gly Ile Asn Ser His Asn Gly Lys Ile
450                 455                 460

AGT AGT TAT GTG GAA GGT AAA CGT TAC GGG AAG AAG TAT TTC GCA GGT         1670
Ser Ser Tyr Val Glu Gly Lys Arg Tyr Gly Lys Lys Tyr Phe Ala Gly
465                 470                 475                 480

AAT TTC GAG AGA TTG GTG AAG ATT AAG ACG AGA GTT GAT AGT GGT AAT         1718
Asn Phe Glu Arg Leu Val Lys Ile Lys Thr Arg Val Asp Ser Gly Asn
                485                 490                 495

TTC TTT AGG AAC GAA CAC AGT ATT CCT GTG TTA CCA TAA                     1757
Phe Phe Arg Asn Glu His Ser Ile Pro Val Leu Pro
                500                 505
```

(2) INFORMATION FOR SEQ ID NO: 71:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO: 71:

```
Thr Arg Arg Asn Ser Glu Thr Phe Thr Gln Cys Leu Thr Ser Asn
 1               5                  10                  15

Ser Asp Pro Lys His Pro Ile Ser Pro Ala Ile Phe Phe Ser Gly Asn
                20                  25                  30

Gly Ser Tyr Ser Ser Val Leu Gln Ala Asn Ile Arg Asn Leu Arg Phe
            35                  40                  45

Asn Thr Thr Ser Thr Pro Lys Pro Phe Leu Ile Ile Ala Ala Thr His
        50                  55                  60

Glu Ser His Val Gln Ala Ala Ile Thr Cys Gly Lys Arg His Asn Leu
65                  70                  75                  80

Gln Met Lys Ile Arg Ser Gly Gly His Asp Tyr Asp Gly Leu Ser Tyr
                85                  90                  95

Val Thr Tyr Ser Gly Lys Pro Phe Phe Val Leu Asp Met Phe Asn Leu
            100                 105                 110

Arg Ser Val Asp Val Asp Val Ala Ser Lys Thr Ala Trp Val Gln Thr
        115                 120                 125

Gly Ala Ile Leu Gly Glu Val Tyr Tyr Ile Trp Glu Lys Ser Lys
    130                 135                 140
```

```
Thr Leu Ala Tyr Pro Ala Gly Ile Cys Pro Thr Val Gly Val Gly Gly
145                 150                 155                 160

His Ile Ser Gly Gly Gly Tyr Gly Asn Met Met Arg Lys Tyr Gly Leu
                165                 170                 175

Thr Val Asp Asn Thr Ile Asp Ala Arg Met Val Asp Val Asn Gly Lys
            180                 185                 190

Ile Leu Asp Arg Lys Leu Met Gly Glu Asp Leu Tyr Trp Ala Ile Asn
            195                 200                 205

Gly Gly Gly Gly Gly Ser Tyr Gly Val Val Leu Ala Tyr Lys Ile Asn
            210                 215                 220

Leu Val Glu Val Pro Glu Asn Val Thr Val Phe Arg Ile Ser Arg Thr
225                 230                 235                 240

Leu Glu Gln Asn Ala Thr Asp Ile Ile His Arg Trp Gln Gln Val Ala
                245                 250                 255

Pro Lys Leu Pro Asp Glu Leu Phe Ile Arg Thr Val Ile Asp Val Val
            260                 265                 270

Asn Gly Thr Val Ser Ser Gln Lys Thr Val Arg Thr Thr Phe Ile Ala
            275                 280                 285

Met Phe Leu Gly Asp Thr Thr Thr Leu Leu Ser Ile Leu Asn Arg Arg
290                 295                 300

Phe Pro Glu Leu Gly Leu Val Arg Ser Asp Cys Thr Glu Thr Ser Trp
305                 310                 315                 320

Ile Gln Ser Val Leu Phe Trp Thr Asn Ile Gln Val Gly Ser Ser Glu
            325                 330                 335

Thr Leu Leu Leu Gln Arg Asn Gln Pro Val Asn Tyr Leu Lys Arg Lys
            340                 345                 350

Ser Asp Tyr Val Arg Glu Pro Ile Ser Arg Thr Gly Leu Glu Ser Ile
            355                 360                 365

Trp Lys Lys Met Ile Glu Leu Glu Ile Pro Thr Met Ala Phe Asn Pro
370                 375                 380

Tyr Gly Gly Glu Met Gly Arg Ile Ser Leu Arg Val Thr Pro Phe Pro
385                 390                 395                 400

Tyr Arg Ala Gly Asn Leu Trp Lys Ile Gln Tyr Gly Ala Asn Trp Arg
            405                 410                 415

Asp Glu Thr Leu Thr Asp Arg Tyr Met Glu Leu Thr Arg Lys Leu Tyr
            420                 425                 430

Gln Phe Met Thr Pro Phe Val Ser Lys Asn Pro Arg Gln Ser Phe Phe
            435                 440                 445

Asn Asn Arg Asp Val Asp Leu Gly Ile Asn Ser His Asn Gly Lys Ile
450                 455                 460

Ser Ser Tyr Val Glu Gly Lys Arg Tyr Gly Lys Lys Tyr Phe Ala Gly
465                 470                 475                 480

Asn Phe Glu Arg Leu Val Lys Ile Lys Thr Arg Val Asp Ser Gly Asn
            485                 490                 495

Phe Phe Arg Asn Glu His Ser Ile Pro Val Leu Pro
            500                 505
```

(2) INFORMATION FOR SEQ ID NO: 72:

(i) SEQUENCE CHARACTERISTICS:
        (A) LENGTH: 1527 base pairs
        (B) TYPE: nucleic acid
        (C) STRANDEDNESS: double
        (D) TOPOLOGY: linear

```
    (ii) MOLECULE TYPE: cDNA to mRNA (iii) HYPOTHETICAL: NO (iv) ANTI-SENSE: NO (vi) ORIGINAL SOURCE:
         (A) ORGANISM: Arabidopsis thaliana
         (B) STRAIN: Colombia (ix) FEATURE:
         (A) NAME/KEY: CDS
         (B) LOCATION: 1..1524

(xi) SEQUENCE DESCRIPTION: SEQ ID NO: 72:

ACT TCC CGT AGA AAC TCG GAG ACT TTC ACA CAA TGC CTA ACC TCA AAC      48
Thr Ser Arg Arg Asn Ser Glu Thr Phe Thr Gln Cys Leu Thr Ser Asn
 1               5                  10                  15

TCC GAC CCC AAA CAT CCC ATC TCC CCC GCT ATC TTC TTC TCC GGA AAT      96
Ser Asp Pro Lys His Pro Ile Ser Pro Ala Ile Phe Phe Ser Gly Asn
             20                  25                  30

GGC TCC TAC TCC TCC GTA TTA CAA GCC AAC ATC CGT AAC CTC CGC TTC     144
Gly Ser Tyr Ser Ser Val Leu Gln Ala Asn Ile Arg Asn Leu Arg Phe
         35                  40                  45

AAC ACC ACC TCA ACT CCG AAA CCC TTC CTC ATA ATC GCC GCA ACA CAT     192
Asn Thr Thr Ser Thr Pro Lys Pro Phe Leu Ile Ile Ala Ala Thr His
     50                  55                  60

GAA TCC CAT GTG CAA GCC GCG ATT ACT TGC GGG AAA CGC CAC AAC CTT     240
Glu Ser His Val Gln Ala Ala Ile Thr Cys Gly Lys Arg His Asn Leu
 65                  70                  75                  80

CAG ATG AAA ATC AGA AGT GGA GGC CAC GAC TAC GAT GGC TTG TCA TAC     288
Gln Met Lys Ile Arg Ser Gly Gly His Asp Tyr Asp Gly Leu Ser Tyr
                 85                  90                  95

GTT ACA TAC TCT GGC AAA CCG TTC TTC GTC CTC GAC ATG TTT AAC CTC     336
Val Thr Tyr Ser Gly Lys Pro Phe Phe Val Leu Asp Met Phe Asn Leu
            100                 105                 110

CGT TCG GTG GAT GTC GAC GTG GCA AGT AAG ACC GCG TGG GTC CAA ACC     384
Arg Ser Val Asp Val Asp Val Ala Ser Lys Thr Ala Trp Val Gln Thr
        115                 120                 125

GGT GCC ATA CTC GGA GAA GTT TAT TAC TAT ATA TGG GAG AAG AGC AAA     432
Gly Ala Ile Leu Gly Glu Val Tyr Tyr Tyr Ile Trp Glu Lys Ser Lys
    130                 135                 140

ACC CTA GCT TAT CCC GCC GGA ATT TGT CCC ACG GTT GGT GTC GGT GGC     480
Thr Leu Ala Tyr Pro Ala Gly Ile Cys Pro Thr Val Gly Val Gly Gly
145                 150                 155                 160

CAT ATC AGT GGT GGA GGT TAC GGT AAC ATG ATG AGA AAA TAC GGT CTC     528
His Ile Ser Gly Gly Gly Tyr Gly Asn Met Met Arg Lys Tyr Gly Leu
                165                 170                 175

ACC GTA GAT AAT ACC ATC GAT GCA AGA ATG GTC GAC GTA AAT GGA AAA     576
Thr Val Asp Asn Thr Ile Asp Ala Arg Met Val Asp Val Asn Gly Lys
            180                 185                 190

ATT TTG GAT AGA AAA TTG ATG GGA GAA GAT CTC TAC TGG GCA ATA AAC     624
Ile Leu Asp Arg Lys Leu Met Gly Glu Asp Leu Tyr Trp Ala Ile Asn
        195                 200                 205

GGA GGA GGA GGA GGG AGC TAC GGC GTC GTA TTG GCC TAC AAA ATA AAC     672
Gly Gly Gly Gly Gly Ser Tyr Gly Val Val Leu Ala Tyr Lys Ile Asn
    210                 215                 220

CTT GTT GAA GTC CCA GAA AAC GTC ACC GTT TTC AGA ATC TCC CGG ACG     720
Leu Val Glu Val Pro Glu Asn Val Thr Val Phe Arg Ile Ser Arg Thr
225                 230                 235                 240

TTA GAA CAA AAT GCG ACG GAT ATC ATT CAC CGG TGG CAA CAA GTT GCA     768
Leu Glu Gln Asn Ala Thr Asp Ile Ile His Arg Trp Gln Gln Val Ala
                245                 250                 255
```

```
CCG AAG CTT CCC GAC GAG CTT TTC ATA AGA ACA GTC ATT GAC GTA GTA    816
Pro Lys Leu Pro Asp Glu Leu Phe Ile Arg Thr Val Ile Asp Val Val
        260                 265                 270

AAC GGC ACT GTT TCA TCT CAA AAG ACC GTC AGG ACA ACA TTC ATA GCA    864
Asn Gly Thr Val Ser Ser Gln Lys Thr Val Arg Thr Thr Phe Ile Ala
            275                 280                 285

ATG TTT CTA GGA GAC ACG ACA ACT CTA CTG TCG ATA TTA AAC CGG AGA    912
Met Phe Leu Gly Asp Thr Thr Thr Leu Leu Ser Ile Leu Asn Arg Arg
290                 295                 300

TTC CCA GAA TTG GGT TTG GTC CGG TCT GAC TGT ACC GAA ACA AGC TGG    960
Phe Pro Glu Leu Gly Leu Val Arg Ser Asp Cys Thr Glu Thr Ser Trp
305                 310                 315                 320

ATC CAA TCT GTG CTA TTC TGG ACA AAT ATC CAA GTT GGT TCG TCG GAG   1008
Ile Gln Ser Val Leu Phe Trp Thr Asn Ile Gln Val Gly Ser Ser Glu
                325                 330                 335

ACA CTT CTA CTC CAA AGG AAT CAA CCC GTG AAC TAC CTC AAG AGG AAA   1056
Thr Leu Leu Leu Gln Arg Asn Gln Pro Val Asn Tyr Leu Lys Arg Lys
            340                 345                 350

TCA GAT TAC GTA CGT GAA CCG ATT TCA AGA ACC GGT TTA GAG TCA ATT   1104
Ser Asp Tyr Val Arg Glu Pro Ile Ser Arg Thr Gly Leu Glu Ser Ile
        355                 360                 365

TGG AAG AAA ATG ATC GAG CTT GAA ATT CCG ACA ATG GCT TTC AAT CCA   1152
Trp Lys Lys Met Ile Glu Leu Glu Ile Pro Thr Met Ala Phe Asn Pro
370                 375                 380

TAC GGT GGT GAG ATG GGG AGG ATA TCA TCT ACG GTG ACT CCG TTC CCA   1200
Tyr Gly Gly Glu Met Gly Arg Ile Ser Ser Thr Val Thr Pro Phe Pro
385                 390                 395                 400

TAC AGA GCC GGT AAT CTC TGG AAG ATT CAG TAC GGT GCG AAT TGG AGA   1248
Tyr Arg Ala Gly Asn Leu Trp Lys Ile Gln Tyr Gly Ala Asn Trp Arg
                405                 410                 415

GAT GAG ACT TTA ACC GAC CGG TAC ATG GAA TTG ACG AGG AAG TTG TAC   1296
Asp Glu Thr Leu Thr Asp Arg Tyr Met Glu Leu Thr Arg Lys Leu Tyr
            420                 425                 430

CAA TTC ATG ACA CCA TTT GTT TCC AAG AAT CCG AGA CAA TCG TTT TTC   1344
Gln Phe Met Thr Pro Phe Val Ser Lys Asn Pro Arg Gln Ser Phe Phe
        435                 440                 445

AAT TAC CGT GAT GTT GAT TTG GGT ATT AAT TCT CAT AAT GGG AAA ATC   1392
Asn Tyr Arg Asp Val Asp Leu Gly Ile Asn Ser His Asn Gly Lys Ile
450                 455                 460

AGT AGT TAT GTG GAA GGT AAA CGT TAC GGG AAG AAG TAT TTC GCA GGT   1440
Ser Ser Tyr Val Glu Gly Lys Arg Tyr Gly Lys Lys Tyr Phe Ala Gly
465                 470                 475                 480

AAT TTC GAG AGA TTG GTG AAG ATT AAG ACG AGA GTT GAT AGT GGT AAT   1488
Asn Phe Glu Arg Leu Val Lys Ile Lys Thr Arg Val Asp Ser Gly Asn
                485                 490                 495

TTC TTT AGG AAC GAA CAG AGT ATT CCT GTG TTA CCA TAA               1527
Phe Phe Arg Asn Glu Gln Ser Ile Pro Val Leu Pro
            500                 505
```

(2) INFORMATION FOR SEQ ID NO: 73:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO: 73:

```
Thr Ser Arg Arg Asn Ser Glu Thr Phe Thr Gln Cys Leu Thr Ser Asn
  1               5                  10                  15
```

-continued

Ser Asp Pro Lys His Pro Ile Ser Pro Ala Ile Phe Phe Ser Gly Asn
            20                  25                  30

Gly Ser Tyr Ser Ser Val Leu Gln Ala Asn Ile Arg Asn Leu Arg Phe
        35                  40                  45

Asn Thr Thr Ser Thr Pro Lys Pro Phe Leu Ile Ile Ala Ala Thr His
    50                  55                  60

Glu Ser His Val Gln Ala Ala Ile Thr Cys Gly Lys Arg His Asn Leu
65                  70                  75                  80

Gln Met Lys Ile Arg Ser Gly His Asp Tyr Asp Gly Leu Ser Tyr
                85                  90                  95

Val Thr Tyr Ser Gly Lys Pro Phe Val Leu Asp Met Phe Asn Leu
            100                 105                 110

Arg Ser Val Asp Val Asp Val Ala Ser Lys Thr Ala Trp Val Gln Thr
            115                 120                 125

Gly Ala Ile Leu Gly Glu Val Tyr Tyr Tyr Ile Trp Glu Lys Ser Lys
130                 135                 140

Thr Leu Ala Tyr Pro Ala Gly Ile Cys Pro Thr Val Gly Val Gly
145                 150                 155                 160

His Ile Ser Gly Gly Gly Tyr Gly Asn Met Met Arg Lys Tyr Gly Leu
                165                 170                 175

Thr Val Asp Asn Thr Ile Asp Ala Arg Met Val Asp Val Asn Gly Lys
            180                 185                 190

Ile Leu Asp Arg Lys Leu Met Gly Glu Asp Leu Tyr Trp Ala Ile Asn
            195                 200                 205

Gly Gly Gly Gly Ser Tyr Gly Val Val Leu Ala Tyr Lys Ile Asn
        210                 215                 220

Leu Val Glu Val Pro Glu Asn Val Thr Val Phe Arg Ile Ser Arg Thr
225                 230                 235                 240

Leu Glu Gln Asn Ala Thr Asp Ile Ile His Arg Trp Gln Gln Val Ala
                245                 250                 255

Pro Lys Leu Pro Asp Glu Leu Phe Ile Arg Thr Val Ile Asp Val Val
            260                 265                 270

Asn Gly Thr Val Ser Ser Gln Lys Thr Val Arg Thr Phe Ile Ala
        275                 280                 285

Met Phe Leu Gly Asp Thr Thr Thr Leu Leu Ser Ile Leu Asn Arg Arg
    290                 295                 300

Phe Pro Glu Leu Gly Leu Val Arg Ser Asp Cys Thr Glu Thr Ser Trp
305                 310                 315                 320

Ile Gln Ser Val Leu Phe Trp Thr Asn Ile Gln Val Gly Ser Ser Glu
                325                 330                 335

Thr Leu Leu Leu Gln Arg Asn Gln Pro Val Asn Tyr Leu Lys Arg Lys
            340                 345                 350

Ser Asp Tyr Val Arg Glu Pro Ile Ser Arg Thr Gly Leu Glu Ser Ile
        355                 360                 365

Trp Lys Lys Met Ile Glu Leu Glu Ile Pro Thr Met Ala Phe Asn Pro
370                 375                 380

Tyr Gly Gly Glu Met Gly Arg Ile Ser Ser Thr Val Thr Pro Phe Pro
385                 390                 395                 400

Tyr Arg Ala Gly Asn Leu Trp Lys Ile Gln Tyr Gly Ala Asn Trp Arg
                405                 410                 415

Asp Glu Thr Leu Thr Asp Arg Tyr Met Glu Leu Thr Arg Lys Leu Tyr
            420                 425                 430

```
Gln Phe Met Thr Pro Phe Val Ser Lys Asn Pro Arg Gln Ser Phe Phe
        435                 440                 445

Asn Tyr Arg Asp Val Asp Leu Gly Ile Asn Ser His Asn Gly Lys Ile
        450                 455                 460

Ser Ser Tyr Val Glu Gly Lys Arg Tyr Gly Lys Lys Tyr Phe Ala Gly
465                 470                 475                 480

Asn Phe Glu Arg Leu Val Lys Ile Lys Thr Arg Val Asp Ser Gly Asn
            485                 490                 495

Phe Phe Arg Asn Glu Gln Ser Ile Pro Val Leu Pro
            500                 505
```

(2) INFORMATION FOR SEQ ID NO: 74:

(i) SEQUENCE CHARACTERISTICS:
        (A) LENGTH: 1530 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: Colombia (ix) FEATURE:
        (A) NAME/KEY: CDS
        (B) LOCATION: 1..1527

(xi) SEQUENCE DESCRIPTION: SEQ ID NO: 74:

```
TCC ATC CAA GAT CAA TTC ATA AAC TGT GTC AAA AGA AAC ACA CAT GTT        48
Ser Ile Gln Asp Gln Phe Ile Asn Cys Val Lys Arg Asn Thr His Val
 1               5                  10                  15

TCT TTT CCA CTC GAG AAA ACG TTA TTC ACC CCT GCG AAA AAC GTC TCT        96
Ser Phe Pro Leu Glu Lys Thr Leu Phe Thr Pro Ala Lys Asn Val Ser
                20                  25                  30

TTG TTC AAC CAA GTC CTT GAA TCG ACG GCT CAA AAT CTC CAG TTC TTG       144
Leu Phe Asn Gln Val Leu Glu Ser Thr Ala Gln Asn Leu Gln Phe Leu
            35                  40                  45

GCA AAA TCC ATG CCT AAA CCG GGA TTC ATA TTC AGA CCG ATT CAC CAG       192
Ala Lys Ser Met Pro Lys Pro Gly Phe Ile Phe Arg Pro Ile His Gln
        50                  55                  60

TCT CAA GTC CAA GCT TCC ATC ATT TGT TCA AAG AAA CTC GGA ATT CAT       240
Ser Gln Val Gln Ala Ser Ile Ile Cys Ser Lys Lys Leu Gly Ile His
65                  70                  75                  80

TTT CGT GTT AGA AGT GGC GGT CAC GAT TTC GAG GCC TTG TCT TAT GTT       288
Phe Arg Val Arg Ser Gly Gly His Asp Phe Glu Ala Leu Ser Tyr Val
                85                  90                  95

TCA CGG ATT GAA AAA CCG TTT ATA TTA CTC GAC CTG TCA AAA TTG AAA       336
Ser Arg Ile Glu Lys Pro Phe Ile Leu Leu Asp Leu Ser Lys Leu Lys
                100                 105                 110

CAA ATC AAT GTT GAT ATT GAA TCC AAT AGT GCT TGG GTT CAA CCT GGT       384
Gln Ile Asn Val Asp Ile Glu Ser Asn Ser Ala Trp Val Gln Pro Gly
            115                 120                 125

GCT ACG CTT GGT GAG CTT TAC TAC AGA ATT GCA GAG AAG AGC AAG ATC       432
Ala Thr Leu Gly Glu Leu Tyr Tyr Arg Ile Ala Glu Lys Ser Lys Ile
        130                 135                 140

CAT GGA TTT CCC GCG GGT TTG TGC ACA AGT GTA GGC ATA GGT GGG TAT       480
His Gly Phe Pro Ala Gly Leu Cys Thr Ser Val Gly Ile Gly Gly Tyr
145                 150                 155                 160
```

-continued

| | |
|---|---|
| ATG ACA GGC GGT GGA TAC GGT ACC TTG ATG AGG AAG TAT GGT CTT GCG<br>Met Thr Gly Gly Gly Tyr Gly Thr Leu Met Arg Lys Tyr Gly Leu Ala<br>                165                    170                    175 | 528 |
| GGA GAT AAT GTT CTA GAC GTA AAG ATG GTT GAT GCA AAT GGT AAA TTA<br>Gly Asp Asn Val Leu Asp Val Lys Met Val Asp Ala Asn Gly Lys Leu<br>                180                    185                    190 | 576 |
| CTC GAC AGA GCC GCG ATG GGT GAG GAC CTA TTT TGG GCG ATT AGA GGA<br>Leu Asp Arg Ala Ala Met Gly Glu Asp Leu Phe Trp Ala Ile Arg Gly<br>            195                    200                    205 | 624 |
| GGC GGT GGA GCG AGT TTC GGG ATA GTT CTA GCA TGG AAG ATC AAG CTT<br>Gly Gly Gly Ala Ser Phe Gly Ile Val Leu Ala Trp Lys Ile Lys Leu<br>210                    215                    220 | 672 |
| GTT CCT GTT CCT AAG ACT GTT ACC GTC TTC ACT GTC ACC AAA ACG TTA<br>Val Pro Val Pro Lys Thr Val Thr Val Phe Thr Val Thr Lys Thr Leu<br>225                    230                    235                    240 | 720 |
| GAA CAA GAC GCA AGA TTG AAG ACT ATT TCT AAG TGG CAA CAA ATT TCA<br>Glu Gln Asp Ala Arg Leu Lys Thr Ile Ser Lys Trp Gln Gln Ile Ser<br>                245                    250                    255 | 768 |
| TCC AAG ATT ATT GAA GAG ATA CAC ATC CGA GTG GTA CTC AGA GCA GCT<br>Ser Lys Ile Ile Glu Glu Ile His Ile Arg Val Val Leu Arg Ala Ala<br>            260                    265                    270 | 816 |
| GGA AAT GAT GGA AAC AAG ACT GTG ACA ATG ACC TAC CTA GGT CAG TTT<br>Gly Asn Asp Gly Asn Lys Thr Val Thr Met Thr Tyr Leu Gly Gln Phe<br>            275                    280                    285 | 864 |
| CTT GGC GAG AAA GGC ACC TTG CTG AAG GTT ATG GAG AAG GCT TTT CCA<br>Leu Gly Glu Lys Gly Thr Leu Leu Lys Val Met Glu Lys Ala Phe Pro<br>            290                    295                    300 | 912 |
| GAA CTA GGG TTA ACT CAA AAG GAT TGT ACT GAA ATG AGC TGG ATT GAA<br>Glu Leu Gly Leu Thr Gln Lys Asp Cys Thr Glu Met Ser Trp Ile Glu<br>305                    310                    315                    320 | 960 |
| GCC GCC CTT TTC CAT GGT GGA TTT CCA ACA GGT TCT CCT ATT GAA ATT<br>Ala Ala Leu Phe His Gly Gly Phe Pro Thr Gly Ser Pro Ile Glu Ile<br>                325                    330                    335 | 1008 |
| TTG CTT CAG CTC AAG TCG CCT CTA GGA AAA GAT TAC TTC AAA GCA ACG<br>Leu Leu Gln Leu Lys Ser Pro Leu Gly Lys Asp Tyr Phe Lys Ala Thr<br>            340                    345                    350 | 1056 |
| TCG GAT TTC GTT AAA GAA CCT ATT CCT GTG ATA GGC TTC AAA GGA ATA<br>Ser Asp Phe Val Lys Glu Pro Ile Pro Val Ile Gly Phe Lys Gly Ile<br>                355                    360                    365 | 1104 |
| TTC AAA AGA TTG ATT GAA GGA AAC ACA ACA TTT CTG AAC TGG ACT CCT<br>Phe Lys Arg Leu Ile Glu Gly Asn Thr Thr Phe Leu Asn Trp Thr Pro<br>370                    375                    380 | 1152 |
| TAC GGT GGT ATG ATG TCG AAA ATC CCT GAA TCT GCG ATC CCA TTT CCG<br>Tyr Gly Gly Met Met Ser Lys Ile Pro Glu Ser Ala Ile Pro Phe Pro<br>385                    390                    395                    400 | 1200 |
| CAT AGA AAC GGA ACC CTC TTC AAG ATT CTC TAT TAC GCG AAC TGG CTA<br>His Arg Asn Gly Thr Leu Phe Lys Ile Leu Tyr Tyr Ala Asn Trp Leu<br>                405                    410                    415 | 1248 |
| GAG AAT GAC AAG ACA TCG AGT AGA AAA ATC AAC TGG ATC AAA GAG ATA<br>Glu Asn Asp Lys Thr Ser Ser Arg Lys Ile Asn Trp Ile Lys Glu Ile<br>            420                    425                    430 | 1296 |
| TAC AAT TAC ATG GCG CCT TAT GTC TCA AGC AAT CCA AGA CAA GCA TAT<br>Tyr Asn Tyr Met Ala Pro Tyr Val Ser Ser Asn Pro Arg Gln Ala Tyr<br>                435                    440                    445 | 1344 |
| GTG AAC TAC AGA GAT CTA GAC TTC GGA CAG AAC AAG AAC AAC GCA AAG<br>Val Asn Tyr Arg Asp Leu Asp Phe Gly Gln Asn Lys Asn Asn Ala Lys<br>450                    455                    460 | 1392 |
| GTT AAC TTC ATT GAA GCT AAA ATC TGG GGA CCT AAG TAC TTC AAA GGC<br>Val Asn Phe Ile Glu Ala Lys Ile Trp Gly Pro Lys Tyr Phe Lys Gly | 1440 |

```
                    465                 470                 475                 480
AAT TTT GAC AGA TTG GTG AAG ATT AAA ACC AAG GTT GAT CCA GAG AAC              1488
Asn Phe Asp Arg Leu Val Lys Ile Lys Thr Lys Val Asp Pro Glu Asn
                        485                 490                 495

TTC TTC AGG CAC GAG CAG AGT ATC CCA CCT ATG CCC TAC TAG                      1530
Phe Phe Arg His Glu Gln Ser Ile Pro Pro Met Pro Tyr
                500                 505
```

(2) INFORMATION FOR SEQ ID NO: 75:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO: 75:

```
Ser Ile Gln Asp Gln Phe Ile Asn Cys Val Lys Arg Asn Thr His Val
 1               5                  10                  15

Ser Phe Pro Leu Glu Lys Thr Leu Phe Thr Pro Ala Lys Asn Val Ser
             20                  25                  30

Leu Phe Asn Gln Val Leu Glu Ser Thr Ala Gln Asn Leu Gln Phe Leu
         35                  40                  45

Ala Lys Ser Met Pro Lys Pro Gly Phe Ile Phe Arg Pro Ile His Gln
 50                  55                  60

Ser Gln Val Gln Ala Ser Ile Ile Cys Ser Lys Lys Leu Gly Ile His
 65                  70                  75                  80

Phe Arg Val Arg Ser Gly Gly His Asp Phe Glu Ala Leu Ser Tyr Val
             85                  90                  95

Ser Arg Ile Glu Lys Pro Phe Ile Leu Leu Asp Leu Ser Lys Leu Lys
            100                 105                 110

Gln Ile Asn Val Asp Ile Glu Ser Asn Ser Ala Trp Val Gln Pro Gly
        115                 120                 125

Ala Thr Leu Gly Glu Leu Tyr Tyr Arg Ile Ala Glu Lys Ser Lys Ile
130                 135                 140

His Gly Phe Pro Ala Gly Leu Cys Thr Ser Val Gly Ile Gly Gly Tyr
145                 150                 155                 160

Met Thr Gly Gly Gly Tyr Gly Thr Leu Met Arg Lys Tyr Gly Leu Ala
            165                 170                 175

Gly Asp Asn Val Leu Asp Val Lys Met Val Asp Ala Asn Gly Lys Leu
        180                 185                 190

Leu Asp Arg Ala Ala Met Gly Glu Asp Leu Phe Trp Ala Ile Arg Gly
    195                 200                 205

Gly Gly Gly Ala Ser Phe Gly Ile Val Leu Ala Trp Lys Ile Lys Leu
210                 215                 220

Val Pro Val Pro Lys Thr Val Thr Val Phe Thr Val Thr Lys Thr Leu
225                 230                 235                 240

Glu Gln Asp Ala Arg Leu Lys Thr Ile Ser Lys Trp Gln Gln Ile Ser
            245                 250                 255

Ser Lys Ile Ile Glu Glu Ile His Ile Arg Val Val Leu Arg Ala Ala
        260                 265                 270

Gly Asn Asp Gly Asn Lys Thr Val Thr Met Thr Tyr Leu Gly Gln Phe
    275                 280                 285

Leu Gly Glu Lys Gly Thr Leu Leu Lys Val Met Glu Lys Ala Phe Pro
290                 295                 300
```

-continued

```
Glu Leu Gly Leu Thr Gln Lys Asp Cys Thr Glu Met Ser Trp Ile Glu
305                 310                 315                 320

Ala Ala Leu Phe His Gly Gly Phe Pro Thr Gly Ser Pro Ile Glu Ile
                325                 330                 335

Leu Leu Gln Leu Lys Ser Pro Leu Gly Lys Asp Tyr Phe Lys Ala Thr
            340                 345                 350

Ser Asp Phe Val Lys Glu Pro Ile Pro Val Ile Gly Phe Lys Gly Ile
        355                 360                 365

Phe Lys Arg Leu Ile Glu Gly Asn Thr Thr Phe Leu Asn Trp Thr Pro
    370                 375                 380

Tyr Gly Gly Met Met Ser Lys Ile Pro Glu Ser Ala Ile Pro Phe Pro
385                 390                 395                 400

His Arg Asn Gly Thr Leu Phe Lys Ile Leu Tyr Tyr Ala Asn Trp Leu
                405                 410                 415

Glu Asn Asp Lys Thr Ser Ser Arg Lys Ile Asn Trp Ile Lys Glu Ile
            420                 425                 430

Tyr Asn Tyr Met Ala Pro Tyr Val Ser Ser Asn Pro Arg Gln Ala Tyr
        435                 440                 445

Val Asn Tyr Arg Asp Leu Asp Phe Gly Gln Asn Lys Asn Asn Ala Lys
    450                 455                 460

Val Asn Phe Ile Glu Ala Lys Ile Trp Gly Pro Lys Tyr Phe Lys Gly
465                 470                 475                 480

Asn Phe Asp Arg Leu Val Lys Ile Lys Thr Lys Val Asp Pro Glu Asn
                485                 490                 495

Phe Phe Arg His Glu Gln Ser Ile Pro Pro Met Pro Tyr
            500                 505
```

(2) INFORMATION FOR SEQ ID NO: 76:

(i) SEQUENCE CHARACTERISTICS:
        (A) LENGTH: 539 amino acids
        (B) TYPE: amino acid
        (D) TOPOLOGY: linear (ii) MOLECULE TYPE: protein (xi) SEQUENCE DESCRIPTION: SEQ ID NO: 76:

```
Met Glu Asn Lys Thr Pro Ile Phe Phe Ser Leu Ser Ile Phe Leu Ser
1               5                   10                  15

Leu Leu Asn Cys Ala Leu Gly Gly Asn Asp Leu Leu Ser Cys Leu Thr
                20                  25                  30

Phe Asn Gly Val Arg Asn His Thr Val Phe Ser Ala Asp Ser Asp Ser
            35                  40                  45

Asp Phe Asn Arg Phe Leu His Leu Ser Ile Gln Asn Pro Leu Phe Gln
        50                  55                  60

Asn Ser Leu Ile Ser Lys Pro Ser Ala Ile Ile Leu Pro Gly Ser Lys
65                  70                  75                  80

Glu Glu Leu Ser Asn Thr Ile Arg Cys Ile Arg Lys Gly Ser Trp Thr
                85                  90                  95

Ile Arg Leu Arg Ser Gly Gly His Ser Tyr Glu Gly Leu Ser Tyr Thr
            100                 105                 110

Ser Asp Thr Pro Phe Ile Leu Ile Asp Leu Met Asn Leu Asn Arg Val
        115                 120                 125

Ser Ile Asp Leu Glu Ser Glu Thr Ala Trp Val Glu Ser Gly Ser Thr
    130                 135                 140

Leu Gly Glu Leu Tyr Tyr Ala Ile Thr Glu Ser Ser Ser Lys Leu Gly
```

-continued

```
145                 150                 155                 160
Phe Thr Ala Gly Trp Cys Pro Thr Val Gly Thr Gly His Ile Ser
                165                 170                 175
Gly Gly Gly Phe Gly Met Met Ser Arg Lys Tyr Gly Leu Ala Ala Asp
            180                 185                 190
Asn Val Val Asp Ala Ile Leu Ile Asp Ala Asn Gly Ala Ile Leu Asp
            195                 200                 205
Arg Gln Ala Met Gly Glu Asp Val Phe Trp Ala Ile Arg Gly Gly
        210                 215                 220
Gly Gly Val Trp Gly Ala Ile Tyr Ala Trp Lys Ile Lys Leu Leu Pro
225                 230                 235                 240
Val Pro Glu Lys Val Thr Val Phe Arg Val Thr Lys Asn Val Ala Ile
                245                 250                 255
Asp Glu Ala Thr Ser Leu Leu His Lys Trp Gln Phe Val Ala Glu Glu
            260                 265                 270
Leu Glu Glu Asp Phe Thr Leu Ser Val Leu Gly Gly Ala Asp Glu Lys
            275                 280                 285
Gln Val Trp Leu Thr Met Leu Gly Phe His Phe Gly Leu Lys Thr Val
        290                 295                 300
Ala Lys Ser Thr Phe Asp Leu Leu Phe Pro Glu Leu Gly Leu Val Glu
305                 310                 315                 320
Glu Asp Tyr Leu Glu Met Ser Trp Gly Glu Ser Phe Ala Tyr Leu Ala
                325                 330                 335
Gly Leu Glu Thr Val Ser Gln Leu Asn Asn Arg Phe Leu Lys Phe Asp
            340                 345                 350
Glu Arg Ala Phe Lys Thr Lys Val Asp Leu Thr Lys Glu Pro Leu Pro
            355                 360                 365
Ser Lys Ala Phe Tyr Gly Gly Leu Leu Glu Arg Leu Ser Lys Glu Pro
        370                 375                 380
Asn Gly Phe Ile Ala Leu Asn Gly Phe Gly Gly Gln Met Ser Lys Ile
385                 390                 395                 400
Ser Ser Asp Phe Thr Pro Phe Pro His Arg Ser Gly Thr Arg Leu Met
                405                 410                 415
Val Glu Tyr Ile Val Ala Trp Asn Gln Ser Glu Gln Lys Lys Lys Thr
            420                 425                 430
Glu Phe Leu Asp Trp Leu Glu Lys Val Tyr Glu Phe Met Lys Pro Phe
            435                 440                 445
Val Ser Lys Asn Pro Arg Leu Gly Tyr Val Asn His Ile Asp Leu Asp
        450                 455                 460
Leu Gly Gly Ile Asp Trp Gly Asn Lys Thr Val Val Asn Asn Ala Ile
465                 470                 475                 480
Glu Ile Ser Arg Ser Trp Gly Glu Ser Tyr Phe Leu Ser Asn Tyr Glu
                485                 490                 495
Arg Leu Ile Arg Ala Lys Thr Leu Ile Asp Pro Asn Asn Val Phe Asn
            500                 505                 510
His Pro Gln Ser Ile Pro Pro Met Ala Asn Phe Asp Tyr Leu Glu Lys
            515                 520                 525
Thr Leu Gly Ser Asp Gly Gly Glu Val Val Ile
530                 535
```

(2) INFORMATION FOR SEQ ID NO: 77:

(i) SEQUENCE CHARACTERISTICS:
        (A) LENGTH: 536 amino acids

-continued (B) TYPE: amino acid
(D) TOPOLOGY: linear (ii) MOLECULE TYPE: protein (xi) SEQUENCE DESCRIPTION: SEQ ID NO: 77:

```
Met Met Cys Arg Ser Leu Thr Leu Arg Phe Leu Phe Ile Val Leu
1               5                   10                  15

Leu Gln Thr Cys Val Arg Gly Gly Asp Val Asn Asp Asn Leu Leu Ser
                20                  25                  30

Ser Cys Leu Asn Ser His Gly Val His Asn Phe Thr Thr Leu Ser Thr
            35                  40                  45

Asp Thr Asn Ser Asp Tyr Phe Lys Leu Leu His Ala Ser Met Gln Asn
    50                  55                  60

Pro Leu Phe Ala Lys Pro Thr Val Ser Lys Pro Ser Phe Ile Val Met
65                  70                  75                  80

Pro Gly Ser Lys Glu Glu Leu Ser Ser Thr Val His Cys Cys Thr Arg
                85                  90                  95

Glu Ser Trp Thr Ile Arg Leu Arg Ser Gly Gly His Ser Tyr Glu Gly
                100                 105                 110

Leu Ser Tyr Thr Ala Asp Thr Pro Phe Val Ile Val Asp Met Met Asn
            115                 120                 125

Leu Asn Arg Ile Ser Ile Asp Val Leu Ser Glu Thr Ala Trp Val Glu
    130                 135                 140

Ser Gly Ala Thr Leu Gly Glu Leu Tyr Tyr Ala Ile Ala Gln Ser Thr
145                 150                 155                 160

Asp Thr Leu Gly Phe Thr Ala Gly Trp Cys Pro Thr Val Gly Ser Gly
                165                 170                 175

Gly His Ile Ser Gly Gly Gly Phe Gly Met Met Ser Arg Lys Tyr Gly
                180                 185                 190

Leu Ala Ala Asp Asn Val Val Asp Ala Ile Leu Ile Asp Ser Asn Gly
    195                 200                 205

Ala Ile Leu Asp Arg Glu Lys Met Gly Asp Asp Val Phe Trp Ala Ile
    210                 215                 220

Arg Gly Gly Gly Gly Val Trp Gly Ala Ile Tyr Ala Trp Lys Ile
225                 230                 235                 240

Lys Leu Leu Pro Val Pro Glu Lys Leu Thr Val Phe Arg Val Thr Lys
                245                 250                 255

Asn Val Gly Ile Glu Asp Ala Ser Ser Leu Leu His Lys Trp Gln Tyr
                260                 265                 270

Val Ala Asp Glu Leu Asp Glu Asp Phe Thr Val Ser Val Leu Gly Gly
    275                 280                 285

Val Asn Gly Asn Asp Ala Trp Leu Met Phe Leu Gly Leu His Leu Gly
    290                 295                 300

Arg Lys Asp Ala Ala Lys Thr Ile Ile Asp Glu Lys Phe Pro Glu Leu
305                 310                 315                 320

Gly Leu Val Asp Lys Glu Phe Gln Glu Met Ser Trp Gly Glu Ser Met
                325                 330                 335

Ala Phe Leu Ser Gly Leu Asp Thr Ile Ser Glu Leu Asn Asn Arg Phe
            340                 345                 350

Leu Lys Phe Asp Glu Arg Ala Phe Lys Thr Lys Val Asp Phe Thr Lys
    355                 360                 365

Val Ser Val Pro Leu Asn Val Phe Arg His His Ala Leu Glu Met Leu
370                 375                 380
```

```
Ser Glu Gln Pro Gly Gly Phe Ile Ala Leu Asn Gly Phe Gly Gly Lys
385                 390                 395                 400

Met Ser Glu Ile Ser Thr Asp Phe Thr Pro Phe Pro His Arg Lys Gly
                405                 410                 415

Thr Lys Leu Met Phe Glu Tyr Ile Ile Ala Trp Asn Gln Asp Glu Glu
                420                 425                 430

Ser Lys Ile Gly Glu Phe Ser Glu Trp Leu Ala Lys Phe Tyr Asp Tyr
            435                 440                 445

Leu Glu Pro Phe Val Ser Lys Glu Pro Arg Val Gly Tyr Val Asn His
            450                 455                 460

Ile Asp Leu Asp Ile Gly Gly Ile Asp Trp Arg Asn Lys Ser Ser Thr
465                 470                 475                 480

Thr Asn Ala Val Glu Ile Ala Arg Asn Trp Gly Glu Arg Tyr Phe Ser
                485                 490                 495

Ser Asn Tyr Glu Arg Leu Val Lys Ala Lys Thr Leu Ile Asp Pro Asn
                500                 505                 510

Asn Val Phe Asn His Pro Gln Ser Ile Pro Pro Met Met Lys Phe Glu
            515                 520                 525

Glu Ile Tyr Met Leu Lys Glu Leu
530                 535
```

ANTIFUNGAL PROTEINS, DNA CODING THEREFORE, AND HOSTS INCORPORATING SAME

This application is a continuation of International Application PCT/EP97/04923 flied on Sep. 4, 1997 and which designated the U.S., claims the benefit thereof and incorporates the same by reference; the international application in turn claims the benefit of foreign applications EPO 96 202466.7, filed Sep. 4, 1996, and EPO 97 200 831.2, filed Mar. 19, 1997.

FIELD OF THE INVENTION

The present invention relates to new oxidases, which can act as antifungal proteins, DNA coding therefor and hosts incorporating the DNA, as well as methods of combating fungal pathogens by causing said fungal pathogens to be contacted with said protein or proteins. The invention further relates to plants, incorporating and expressing DNA coding for antifungal proteins, and to plants which as a result thereof show reduced susceptibility to fungal pathogens.

BACKGROUND ART

Fungal diseases of crop plants have been one of the principal causes of crop losses throughout the history of crop cultivation. The growing of crops as monocultures encourages the proliferation of virulent races of fungal pathogens and wherever a new variety of crop plant becomes grown on a wide scale of the risks of a virulent strain of a pathogen evolving to attack that crop increase drastically. The occurrence of disease is significantly worsened by the international transport of pathogen-carrying plant materials, which can bring together plants with pathogens against which they have had no opportunity to evolve resistance. Thus by man's intervention the natural balance between host and pathogen has been disturbed with disastrous effect on a number of occasions. Catastrophic losses and even famines such as occurred in Ireland during the 19th century, caused by the potato blight fungus (*Phytophthora infestans*) have resulted from such activities. Fungal disease can also make it completely impossible to grow certain crops in large areas, as was the case when Fusarium wilt wiped out tomato growing in large areas of the Eastern USA or the downy mildew (*Plasmopara viticola*) fungus devastated vine growing in parts of Europe. Outbreaks of fungal disease can also have a severe effect on the environment as happened when almost the entire English Elm (*Ulmus procera*) population was destroyed by Dutch Elm Disease (*Ceratocystis ulmi*). In addition the losses which may be caused during the growing of crops fungal disease may contribute to further post harvest losses. Various soft rots such as *Botrytis cinerea* are particularly problematic in soft fruit, for example. The fungus *Aspergillus flavus*, although not a true disease-causing fungus, causes post-harvest rot on stored peanuts and maize, especially in tropical countries and is most serious because it produces a toxin, aflatoxin, which is very toxic to man.

The major economic problems associated with fungal diseases are found in wetter parts of the World, principally Western Europe and the humid tropics. Various crop husbandry techniques, such as crop rotation and avoiding the spread of soil on machinery etc., are used to prevent the build up and spread of severe infestations of fungal disease. Plant breeding has made a significant impact on improving the resistance of many crops to important diseases. For example, plant breeders successfully introduced resistance genes 1 and 1–2 effective against *Fusarium oxysporum* f.sp. *lycopersici* into tomato. Nonetheless, problems remain, particularly when many forms of race-specific resistance break down as new races of the pathogen rapidly evolve. In tomato, another virulent strain of *F. oxysporum* has occurred and breeders are seeking a third useful resistance gene. In cereals growing in parts of Western Europe a recent outbreak of a virulent strain of yellow rust (*Puccinia striiformis*) has lead to a rapid increase in fungicide use on varieties which remain resistant to other fungi. In these specific cases chemicals are widely used to control fungal disease, as in cases where there are simply no natural sources of resistance available to the breeder.

Chemical fungicides remain a major input in the costs of crop production in many parts of the World. In 1990 21% of all agrochemical sales were accounted for by fungicides (US $ 5.54 million). Farmers and growers have a strong motivation to reduce their input costs. Added to the economic justification is an increasingly strong environmental component in the equation. There is growing pressure in the more advanced economies, notably in North America and Western Europe, from politicians and consumers for agriculture which relies less on chemical inputs. The justification for such demands may lack focused rationale or scientific proof, but fears grow with reports of pesticides traced in groundwater or detected in quantities exceeding the minimums acceptable as food residues. In The Netherlands, for example, there is a mandatory requirement to reduce total pesticides use by 50% before 2000.

*Phytophthora infestans* belongs to the group of fungi referred to as Oomycetes. *Phytophthora infestans* infects various members of Solanaceae, such as potato, tomato and some ornamentals. It causes late blight of potatoes and tomatoes affecting all parts except roots. Geographically, the fungus is widely distributed, and it can be found in all potato-producing countries. Economically late blight in potatoes is of major importance, as infection early in the season can severely reduce crop yield. Currently the disease is controlled by spraying chemical fungicides (dithiocarbamates, such as mancozeb, manec and zineb) regularly. Both from an environmental and economical point of view, biological control of diseases caused by *Phytophthora infestans* could have advantages over the use of chemical fungicides.

Pythium also belongs to the group of fungi referred to as Oomycetes. The genus Pythium differs from the related genus Phytophthora by forming relatively undifferentiated sporangia. Geographically, this fungus is widely distributed on all continents. The first main type of disease caused by Pythium species is damping-off, due to sudden and fast developing attacks on young seedlings in the field or in nurseries. Pythium species cause a second type of disease which is root necrosis and causes a general slowing of plant growth (for example wheat and maize) and loss of yield. The main losses caused by Pythium in Europe are to field crops such as sugarbeet. In principle, losses tend to be all-or-nothing. Similarly, nursery sowings of ornamentals and forest trees may be completely destroyed. (For a review on Oomycetes, vide: European Handbook of Plant Diseases, ed. by I. M. Smith et al., 1988, Blackwell Scientific Publications, Ch.8)

Another fungus is Botrytis, especially *B. cinerea*, belonging to the group of Fungi Imperfecti, which causes gray mold blight or bud and flower blight, which is common on soft ripe fruits after harvesting, but it can also occur before harvest. It can also affect various vegetables such as lettuce, beans and tomato. Other species of Botrytis are common on flowers, such as lilies, gladiolus and tulips.

A protein with antifungal activity, isolated from TMV-induced tobacco leaves, which is capable of causing lysis of germinating spores and hyphal tips of Phytophthora infestans and which causes the hyphae to grow at a reduced rate, was disclosed in WO91/18984 A1. This protein has an apparent molecular weight of about 24 kDa and was named AP24. Comparison of its complete amino acid sequence, as deduced from the nucleic acid sequence of the AP24 gene, with proteins known from databases revealed that the protein was an osmotin-like protein.

Despite initial success in combating fungal pathogens, such as Phytophthora infestans, and the genetic engineering of plants capable of producing these antifungal proteins with activity against this fungal pathogen there remains a need to identify and isolate other proteins with antifungal activity against this fungus.

SUMMARY OF THE INVENTION

The present invention provides an isolated protein obtainable from a plant source which has antifungal activity, most effectively directed to Oomycetes, and preferably to Phytophthora and/or Pythium and a molecular weight of about 55–65 kDa as judged by SDS PAGE-electrophoresis. Preferred proteins are those that are obtainable from sunflower or lettuce plants. Even more preferred proteins are obtainable from sunflower or lettuce leaves induced with sodium salicylate. A still more preferred isolated protein is characterised in that it is selected from the group of proteins having the amino acid sequence selected from the group comprising of the amino acid sequences depicted in SEQ ID NO's: 1, 2 or 6, 16, 20, 49, 50, 51, 58, 71, 73 or 75 as well as muteins thereof which have antifungal and especially anti-Phytophthora and/or anti-Pythium activity. A still further preferred protein according to the invention is one characterised in that it comprises a protein that comprises the amino acid sequence as represented by SEQ ID NO's: 16, 20, 58, 71, 73 or 75 or by a part of said sequence like represented in SEQ ID NO: 6.

The invention also provides a new enzyme, the enzymatic activity being oxidation of carbohydrates.

The invention also embraces an isolated DNA sequence comprising an open reading frame capable of encoding a protein according to the invention, preferably characterised in that the open reading frame is capable of encoding a protein according to the invention, and DNA capable of hybridising therewith under stringent conditions.

The invention also provides a chimeric DNA sequence according to the invention further comprising a transcriptional initiation region and, optionally, a transcriptional termination region, so linked to said open reading frame as to enable the DNA to be transcribed in a living host cell when present therein, thereby producing RNA which comprises said open reading frame. A preferred chimeric DNA sequence according to the invention is one, wherein the RNA comprising said open reading frame is capable of being translated into protein in said host cell, when present therein, thereby producing said protein. Especially preferred are DNA sequences comprising a sequence as depicted in SEQ ID NO's: 15, 19, 57, 70, 72 or 74.

The invention also embraces a chimeric DNA sequence comprising a DNA sequence according to the invention, which may be selected from replicons, such as bacterial cloning plasmids and vectors, such as a bacterial expression vector, a (non-integrative) plant viral vector, a Ti-plasmid vector of Agrobacterium, such as a binary vector, and the like, as well as a host cell comprising a replicon or vector according to the invention, and which is capable of maintaining said replicon once present therein. Preferred according to that embodiment is a host cell which is a plant cell, said vector being a non-integrative viral vector.

The invention further provides a host cell stably incorporating in its genome a chimeric DNA sequence according to the invention, such as a plant cell, as well as multicellular hosts comprising such cells, or essentially consisting of such cells, such as plants. Especially preferred are plants characterised in that the chimeric DNA according to the invention is expressed in at least a number of the plant's cells causing the said antifungal protein to be produced therein.

According to yet another embodiment of the invention a method for producing a protein with carbohydrate oxidase activity is provided, characterised in that a host cell according to the invention is grown under conditions allowing the said protein to be produced by said host cell, optionally followed by the step of recovering the protein from the host cells.

Another part of the invention is directed to the antifungal use of a protein which has carbohydrate oxidase activity.

The invention provides also for the use of a protein according to the invention for retarding the growth of fungi, preferably Oomycetes and more preferably Phytophthora and Pythium. According to yet another embodiment, retarding the growth of the fungi is on or in the neighbourhood of the plant by applying a microorganism capable of producing the protein or by harvesting the protein from a microbial host and applying the protein in an agrochemical formulation.

The invention also provides a method for obtaining plants with reduced susceptibility to fungi, especially Phytophthora and/or Pythium, comprising the steps of (a) introducing into ancestor cells which are susceptible of regeneration into a whole plant,
   a chimeric DNA sequence comprising an open reading frame capable of encoding a protein according to claim 1, said open reading frame being operatively linked to a transcriptional and translational region and, optionally, a transcriptional termination region, allowing the said protein to be produced in a plant cell that is susceptible to infection by said fungus, and
   a chimeric DNA sequence capable of encoding a plant selectable marker allowing selection of transformed ancestor cells when said selectable marker is present therein, and
(b) regenerating said ancestor cells into plants under conditions favouring ancestor cells which have the said selectable marker, and
(c) identifying a plant which produces a protein according to claim 1, thereby reducing the susceptibility of said plant to infection by said fungus.

Preferred according to the invention is a method characterised in that step (a) is performed using an Agrobacterium tumefaciens strain capable of T-DNA transfer to plant cells and which harbours the said chimeric DNA cloned into binary vector pMOG800; another preferred method is when step (b) is performed in the presence of an antibiotic favouring cells which have a neomycin phosphotransferase.

The invention further provides an antifungal composition comprising a protein according to the invention and a suitable carrier.

An antibody, capable of reacting with an N-terminal fragment of a protein according to the invention, preferably to the peptide represented by SEQ ID NO's: 6, 16, 20, 58, 71, 73 or 75 is also provided. The antibody is suitably used to detect expression levels of chimeric DNA according to the invention in host cells and multicellular hosts, preferably plants, capable of producing a protein according to the invention.

The invention also provides a nucleic acid sequence obtainable from a gene encoding a protein according to the invention, said nucleic acid sequence having tissue-specific transcriptional regulatory activity in plant. The invention specifically provides a nucleic acid sequence obtainable from the region upstream of the translational initiation site of said gene, preferably at least 500 nucleotides immediately upstream of the translational initiation site of said gene.

DESCRIPTION OF THE FIGURES

FIG. 6A: SD 75 gelfiltration profile of WL64. WL64 eluates at fractions 13, 14, 15. Molecular weight markers are indicated above the arrows at the top of the plot. X-axis: fraction number. Y-axis: A280.

FIGS. 10A and B: Alignment of the proteins of the invention MS59 (SEQ ID NO: 16), WL64 (SEQ ID NO: 58) and the two homologues from *A. thaliana* At26 (SEQ ID NO: 71) and At27 (SEQ ID NO: 75) (with the known berberine bridge enzymes (EcBBE (SEQ ID NO: 76) and PsBBE (SEQ ID NO: 77)). Conserved changes are denoted in gray, while areas of identity (3 of the 6 amino acids identical) are given in black.

DETAILED DESCRIPTION OF THE INVENTION

Figure 1:
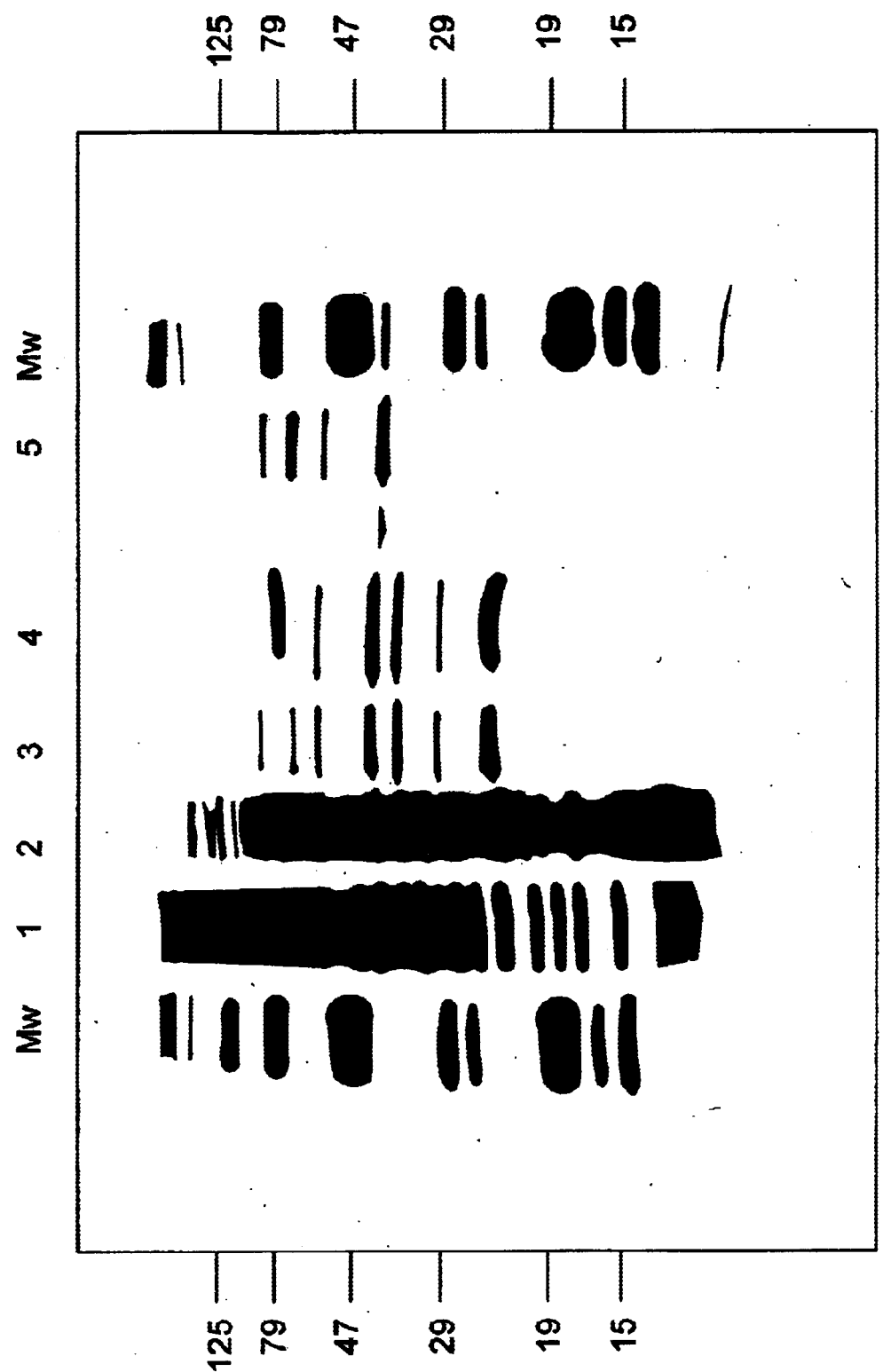
FIG. 1: SDS-PAGE (12.5%) of the different purification steps of MS59 sunflower protein. Mw=molecular weight markers; 1=crude sunflower protein extract after gel filtration (G25); 2=protein fraction bound to cation exchange chromatography (S-sepharose); 3=pool of active fractions after cation exchange chromatography (Mono S); 4=flow through from hydrophobic interaction chromatography (phenyl superose); 5=active fractions after gel filtration.

The antifungal effect of the protein(s) of the invention has been demonstrated in in vitro assays for the following fungi; *Phytophthora infestans, Phytophthora cactorum, Phytophtora nicotiana, Phytophthora megasperma, Pythium ultimum, Pythium sylvaticum, Pythium violae, Pythium paroecandrum, Rhizoctonia solani, Tanatephorus cucumeris, Helicobasidium purpureum, Sclerotium cepivorum, Pichia pastoris* and *Botrytis cinerea* for purposes of illustration. It will be clear, that the use of the protein(s) of the invention, or DNA encoding therefore, for use in a process of combating fungi is not limited to the mentioned fungi. There is no reason to assume that the protein(s) according to the invention do not possess antifungal activity against a far broader range of fungi than those tested here, especially in the class of Oomycetes.

Although the invention is illustrated in detail for transgenic tomato, tobacco, carrot, potato and *Brassica napus* plants, it should be understood that any plant species that is subject to some form of fungal attack, especially from the fungi mentioned above, may be provided with one or more plant expressible gene constructs, which when expressed overproduce the protein(s) of the invention in said plant in order to decrease the rate of infectivity and/or the effects of such attack. The invention can even be practiced in plant species that are presently not amenable for transformation, as the amenability of such species is just a matter of time and because transformation as such is of no relevance for the principles underlying the invention. Hence, plants for the purpose of this description shall include angiosperms as well as gymnosperms, monocotyledonous as well as dicotyledonous plants, be they for feed, food or industrial processing purposes; included are plants used for any agricultural or horticultural purpose including forestry and flower culture, as well as home gardening or indoor gardening, or other decorative purposes.

The protein according to the present invention may be obtained by isolating it from any suitable plant source material containing it. A particularly suitable source comprises leaves of the sunflower (Helianthus) and leaves of lettuce (*Lactuca sativa* cv. Lollo bionda). The presence of antifungal proteins according to the invention in plant source material can readily be determined for any plant species by making plant extracts from those species and testing those extracts for the presence of antifungal activity using in vitro antifungal assays as described herein, further fractionating the obtained samples by any suitable protein fractionation technique in conjunction with the in vitro assay until an antifungal fraction is obtained which comprises an approximately 55–65 kDa protein, internally denoted as MS59 or its homologue WL64, which in isolated form shows antifungal activity. Especially, fractions may be tested for antifungal activity on Oomycetes, for example, Phytophthora or *Pythium ultimum* and the like, or other fungi, such as the Basidiomycetes, Ascomycetes, Zygomycetes or other classes or subclasses.

Alternatively, antifungal proteins according to the invention may be obtained by cloning DNA comprising an open reading frame capable of encoding said protein, or the precursor thereof, linking said open reading frame to a transcriptional, and optionally a translational initiation and transcriptional termination region, inserting said DNA into a suitable host cell and allowing said host cell to produce said protein. Subsequently, the protein may be recovered from said host cells, preferably after secretion of the protein into the culture medium by said host cells. Alternatively, said host cells may be used directly in a process of combating fungal pathogens according to the invention as a pesticidal acceptable composition.

Host cells suitable for use in a process of obtaining a protein according to the invention may be selected from prokaryotic microbial hosts, such as bacteria e.g. Agrobacterium, Bacillus, Cyanobacteria, *E.coli*, Pseudomonas, and the like, as well as eukaryotic hosts including yeasts, e.g. *Saccharomyces cerevisiae*, fungi, e.g. Trichoderma and plant cells, including protoplasts.

In a method of retarding the growth of the fungi on or in the neighbourhood of the plant leaves, host cells may suitably be selected from any species routinely used as biological fungicides. Also the proteins can be produced by microorganisms, harvested and applied in a agrochemical formulation.

The word protein means a sequence of amino acids connected trough peptide bonds. Polypeptides or peptides are also considered to be proteins. Muteins of the protein of the invention are proteins that are obtained from the proteins depicted in the sequence listing by replacing, adding and/or deleting one or more amino acids, while still retaining their antifungal activity. Such muteins can readily be made by protein engineering in vivo, e.g. by changing the open reading frame capable of encoding the antifungal protein such that the amino acid sequence is thereby affected. As long as the changes in the amino acid sequences do not altogether abolish the antifungal activity such muteins are embraced in the present invention.

The present invention provides a chimeric DNA sequence which comprises an open reading frame capable of encoding a protein according to the invention. The expression chimeric DNA sequence shall mean to comprise any DNA sequence which comprises DNA sequences not naturally found in nature. For instance, chimeric DNA shall mean to comprise DNA comprising the said open reading frame in a non-natural location of the plant genome, notwithstanding the fact that said plant genome normally contains a copy of the said open reading frame in its natural chromosomal location. Similarly, the said open reading frame may be incorporated in the plant genome wherein it is not naturally found, or in a replicon or vector where it is not naturally found, such as a bacterial plasmid or a viral vector. Chimeric DNA shall not be limited to DNA molecules which are replicable in a host, but shall also mean to comprise DNA capable of being ligated into a replicon, for instance by virtue of specific adaptor sequences, physically linked to the open reading frame according to the invention. The open reading frame may or may not be linked to its natural upstream and downstream regulatory elements.

The open reading frame may be derived from a genomic library. In this latter it may contain one or more introns separating the exons making up the open reading frame that encodes a protein according to the invention. The open reading frame may also be encoded by one uninterrupted exon, or by a cDNA to the mRNA encoding a protein according to the invention. Open reading frames according to the invention also comprise those in which one or more introns have been artificially removed or added. Each of these variants is embraced by the present invention.

Also part of the invention are chimeric DNA sequences coding for an antifungal protein which comprise one or more of the EST-sequences shown in SEQ ID NO's: 21 to 48. As can be derived from the sequence listings these EST's for which no function was hitherto known share a considerable homology with the DNA sequence coding for the proteins isolated from Helianthus and Lactuca.

Another part of the invention is formed by the intrinsic activity of the proteins of the invention. They have been found to be carbohydrate oxidases, capable of oxidating a large number of different mono- and di-saccharides. The substrate specificity resembles the specificity of the enzyme hexose oxidase (EC 1.1.3.5), also known as D-hexose: oxygen 1-oxidoreductase. They have also been shown able to oxidise a purified mixture of fungal (Rhizoctonia-derived) cell wall components. It is believed that this oxidative capacity confers the antifungal properties to the proteins. In literature there is one example of an antifungal oxidase, the glucose oxidase from the fungus Aspergillus (WO 95/14784). The proteins of this invention, however, show a broader substrate spectrum like hexose oxidase and have a lower Km for the substrate.

From homology searches it has been found that some parts of the amino acid sequence of the proteins of the invention are more conserved and are related to sequences commonly found in oxidases. The highest homology has been found with reticuline oxidase, which enzyme is known from the family of Papaveraceae (Facchini, P. J. et al., Plant Physiol. 112, 1669–1677, 1996).

In order to be capable of being expressed in a host cell a chimeric DNA according to the invention will usually be provided with regulatory elements enabling it to be recognised by the biochemical machinery of the host and allowing for the open reading frame to be transcribed and/or translated in the host. It will usually comprise a transcriptional initiation region which may be suitably derived from any gene capable of being expressed in the host cell of choice, as well as a translational initiation region for ribosome recognition and attachment. In eukaryotic cells, an expression cassette usually comprises in addition a transcriptional termination region located downstream of said open reading frame, allowing transcription to terminate and polyadenylation of the primary transcript to occur. In addition, the codon usage may be adapted to accepted codon usage of the host of choice. The principles governing the expression of a chimeric DNA construct in a chosen host cell are commonly understood by those of ordinary skill in the art and the construction of expressible chimeric DNA constructs is now routine for any sort of host cell, be it prokaryotic or eukaryotic.

In order for the open reading frame to be maintained in a host cell it will usually be provided in the form of a replicon comprising said open reading frame according to the invention linked to DNA which is recognised and replicated by the chosen host cell. Accordingly, the selection of the replicon is determined largely by the host cell of choice. Such principles as govern the selection of suitable replicons for a particular chosen host are well within the realm of the ordinary skilled person in the art.

A special type of replicon is one capable of transferring itself, or a part thereof, to another host cell, such as a plant cell, thereby co-transferring the open reading frame according to the invention to said plant cell. Replicons with such capability are herein referred to as vectors. An example of such vector is a Ti-plasmid vector which, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer chimeric DNA sequences into plant cells, or protoplasts, from which new plants may be generated which stably incorporate said chimeric DNA in their genomes. A particularly preferred form of Ti-plasmid vectors are the so-called binary vectors as claimed in (EP 0 120 516 B1 and U.S. Pat. No. 4,940,838). Other suitable vectors, which may be used to introduce DNA according to the invention into a plant host, may be selected from the viral vectors, e.g. non-integrative plant viral vectors, such as derivable from the double stranded plant viruses (e.g. CaMV) and single stranded viruses, gemini viruses and the like. The use of such vectors may be advantageous, particularly when it is difficult to stably transform the plant host. Such may be the case with woody species, especially trees and vines.

The expression "host cells incorporating a chimeric DNA sequence according to the invention in their genome" shall mean to comprise cells, as well as multicellular organisms comprising such cells, or essentially consisting of such cells, which stably incorporate said chimeric DNA into their genome thereby maintaining the chimeric DNA, and preferably transmitting a copy of such chimeric DNA to progeny cells, be it through mitosis or meiosis. According to a preferred embodiment of the invention plants are provided, which essentially consist of cells which incorporate one or more copies of said chimeric DNA into their genome, and which are capable of transmitting a copy or copies to their progeny, preferably in a Mendelian fashion. By virtue of the transcription and translation of the chimeric DNA according to the invention in some or all of the plant's cells, those cells that produce the antifungal protein will show enhanced resistance to fungal infections, especially to Phytophthora infections. Although the principles as indicated above govern transcription of DNA in plant cells are not always understood, the creation of chimeric DNA capable of being expressed in substantially a constitutive fashion, that is, in substantially most cell types of the plant and substantially without serious temporal and/or developmental restrictions, is now routine. Transcription initiation regions routinely in use for that purpose are promoters obtainable from the cauliflower mosaic virus, notably the 35S RNA and 19S RNA transcript promoters and the so-called T-DNA promoters of *Agrobacterium tumefaciens*, in particular to be mentioned are the nopaline synthase promoter, octopine synthase promoter (as disclosed in EP 0 122 791 B1) and the mannopine synthase promoter. In addition plant promoters may be used, which may be substantially constitutive, such as the rice actin gene promoter, or e.g. organ-specific, such as the root-specific promoter. Alternatively, pathogen-inducible promoters may be used such as the PRP1 promoter (also named gst1 promoter) obtainable from potato (Martini N. et al. (1993), Mol. Gen. Genet. 263, 179–186). The choice of the promoter is not essential, although it must be said that constitutive high-level promoters are slightly preferred. It is further known that duplication of certain elements, so-called enhancers, may considerably enhance the expression level of the DNA under its regime (vide for instance: Kay R. et al. (1987), Science 236, 1299–1302: the duplication of the sequence between −343 and −90 of the CaMV 35S promoter increases the activity of that promoter). In addition to the 35S promoter, singly or doubly enhanced, examples of high-level promoters are the light-inducible ribulose bisphosphate carboxylase small subunit (rbcSSU) promoter and the chlorophyll a/b binding protein (Cab) promoter. Also envisaged by the present invention are hybrid promoters, which comprise elements of different promoter regions physically linked. A well known example thereof is the so-called CaMV enhanced mannopine synthase promoter (U.S. Pat. No. 5,106,739), which comprises elements of the mannopine synthase promoter linked to the CaMV enhancer.

As regards the necessity of a transcriptional terminator region, it is generally believed that such a region enhances the reliability as well as the efficiency of transcription in plant cells. Use thereof is therefore strongly preferred in the context of the present invention.

As regards the applicability of the invention in different plant species, it has to be mentioned that one particular embodiment of the invention is merely illustrated with transgenic tomato and tobacco plants as an example, the actual applicability being in fact not limited to these plant species. Any plant species that is subject to some form of fungal attack, in particular by Oomycetes such as *Phytophthora infestans*, may be treated with proteins according to the invention, or preferably, be provided with a chimeric DNA sequence according to the invention, allowing the protein to be produced in some or all of the plant's cells.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle any transformation method may be used to introduce chimeric DNA according to the invention into a suitable ancestor cell, as long as the cells are capable of being regenerated into whole plants. Methods may suitably be selected from the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-integrative) viruses and the like. A preferred method according to the invention comprises Agrobacterium-mediated DNA transfer. Especially preferred is the use of the so-called binary vector technology as disclosed in EP A 120 516 and U.S. Pat. No. 4,940,838).

Tomato transformation is preferably done essentially as described by Van Roekel et al. (Van Roekel, J. S. C., Damm, B., Melchers, L. S., Hoekema, A. (1993). Factors influencing transformation frequency of tomato (*Lycopersicon*

*esculentum*). Plant Cell Reports, 12, 644–647). Potato transformation is preferably done essentially as described by Hoekema et al. (Hoekema, A., Huisman, M. J., Molendijk, L., van den Elzen, P. J. M., and Cornelissen, B. J. C. (1989). The genetic engineering of two commercial potato cultivars for resistance to potato virus X. Bio/Technology 7, 273–278).

Generally, after transformation plant cells or cell groupings are selected for the presence of one or more markers which are encoded by plant expressible genes co-transferred with the nucleic acid sequence encoding the protein according to the invention, whereafter the transformed material is regenerated into a whole plant.

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or electroporation (Shimamoto, et al, 1989, Nature 338, 274–276). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as rice and corn are also amenable to DNA transfer by Agrobacterium strains (vide WO 94/00977; EP 0 159 418 B1; Gould J, Michael D, Hasegawa O, Ulian E C, Peterson G, Smith R H, (1991) Plant. Physiol. 95, 426–434).

Following DNA transfer and regeneration, putatively transformed plants may be evaluated, for instance using Southern analysis, for the presence of the chimeric DNA according to the invention, copy number and/or genomic organization. In addition, or alternatively, expression levels of the newly introduced DNA may be undertaken, using Northern and/or Western analysis, techniques well known to persons having ordinary skill in the art. After the initial analysis, which is optional, transformed plants showing the desired copy number and expression level of the newly introduced chimeric DNA according to the invention may be tested for resistance levels against a pathogen susceptible to the protein according to the invention, such as *Phytophthora infestans*. Alternatively, the selected plants may be subjected to another round of transformation, for instance to introduce further genes, such as genes encoding chitinases, glucanases, osmotins, magainins or the like, in order to enhance resistance levels, or broaden the resistance to other fungi found not to be susceptible to the protein according to the invention in an in vitro assay as described herein.

Other evaluations may include the testing of fungal resistance under field conditions, checking fertility, yield, and other characteristics. Such testing is now routinely performed by persons having ordinary skill in the art.

Following such evaluations, the transformed plants may be grown directly, but usually they may be used as parental lines in the breeding of new varieties or in the creation of hybrids and the like.

Many plant proteins exhibit antifungal effects, some however do not do so as such, but yield a significant synergistic antifungal effect if used in combination with other plant proteins. In European Patent Application 440 304 A1 it was disclosed that simultaneous relative over-expression of a plant expressible glucanase gene in conjunction with a basic chitinase from tobacco in transgenic plants results in a higher level of resistance to fungi than in plants expressing a plant expressible class-I chitinase alone.

Both chitinases, glucanases, osmotins, magainins and the new antifungal protein according to the invention accumulate in infected plant tissues upon an incompatible pathogen-plant interaction. From this observation and the fact that several proteins are found to synergise each others antifungal effects, we envision, that the antifungal protein according to the invention may be suitably used in conjunction with other proteins that are associated with pathogen resistance.

Examples of proteins that may be used in combination with the proteins according to the invention include, but are not limited to, β-1,3-glucanases and chitinases which are obtainable from barley (Swegle M. et al., 1989, Plant Mol. Biol. 12, 403–412; Balance G. M. et al., 1976, Can. J. Plant Sci. 56, 459–466; Hoj P. B. et al., 1988, FEBS Lett. 230, 67–71; Hoj P. B. et al., 1989, Plant Mol. Biol. 13, 31–42 1989), bean (Boller T. et al., 1983, Planta 157, 22–31; Broglie K. E. et al. 1986, Proc. Natl. Acad. Sci. USA 83, 6820–6824; Vögeli U. et al., 1988 Planta 174, 364–372); Mauch F. & Staehelin L. A., 1989, Plant Cell 1, 447–457); cucumber (Motraux J. P. & Boller T. (1986), Physiol. Mol. Plant Pathol. 28, 161–169); leek (Spanu P. et al., 1989, Planta 177, 447–455); maize (Nasser W. et al., 1988, Plant Mol. Biol. 11, 529–538), oat (Fink W. et al., 1988, Plant Physiol. 88, 270–275), pea (Mauch F. et al. 1984, Plant Physiol. 76, 607–611; Mauch F. et al., 1988, Plant Physiol. 87, 325–333), poplar (Parsons, T. J. et al, 1989, Proc. Natl. Acad. Sci. USA 86, 7895–7899), potato (Gaynor J. J. 1988, Nucl. Acids Res. 16, 5210; Kombrink E. et al. 1988, Proc. Natl. Acad. Sci. USA 85, 782–786; Laflamme D. and Roxby R., 1989, Plant Mol. Biol. 13, 249–250), tobacco (e.g. Legrand M. et al. 1987, Proc. Natl. Acad. Sci. USA 84, 6750–6754; Shinshi H. et al. 1987, Proc. Natl. Acad. Sci. USA 84, 89–93), tomato (Joosten M. H. A. & De Wit P. J. G. M. 1989, Plant Physiol. 89, 945–951), wheat (Molano J. et al., 1979, J. Biol. Chem. 254, 4901–4907), and the like.

To obtain transgenic plants capable of constitutively expressing more than one chimeric gene, a number of alternatives are available including the following:

A. The use of DNA, e.g a T-DNA on a binary plasmid, with a number of modified genes physically coupled to a selectable marker gene. The advantage of this method is that the chimeric genes are physically coupled and therefore migrate as a single Mendelian locus.

B. Cross-pollination of transgenic plants each already capable of expressing one or more chimeric genes, preferably coupled to a selectable marker gene, with pollen from a transgenic plant which contains one or more chimeric genes coupled to another selectable marker. Afterwards the seed, which is obtained by this crossing, maybe selected on the basis of the presence of the two selectable markers, or on the basis of the presence of the chimeric genes themselves. The plants obtained from the selected seeds can afterwards be used for further crossing. In principle the chimeric genes are not on a single locus and the genes may therefore segregate as independent loci.

C. The use of a number of a plurality chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second, (etc), chimeric gene with new chimeric DNA, optionally comprising a selectable marker gene. As in method B, the chimeric genes are in principle not on a single locus and the chimeric genes may therefore segregate as independent loci.

E. Combinations of the above mentioned strategies.

The actual strategy may depend on several considerations as maybe easily determined such as the purpose of the parental lines (direct growing, use in a breeding programme, use to produce hybrids) but is not critical with respect to the described invention.

In this context it should be emphasised that plants already containing chimeric DNA capable of encoding antifungal proteins may form a suitable genetic background for introducing chimeric DNA according to the invention, for instance in order to enhance resistance levels, or broaden the resistance. The cloning of other genes corresponding to proteins that can suitably be used in combination with DNA, and the obtention of transgenic plants, capable of relatively over-expressing same, as well as the assessment of their effect on pathogen resistance in planta, is now within the scope of the ordinary skilled person in the art.

The obtention of transgenic plants capable of expressing, or relatively over-expressing, proteins according to the invention is a preferred method for counteracting the damages caused by fungi, such as Oomycetes like *Phytophthora infestans*, as will be clear from the above description. However, the invention is not limited thereto. The invention clearly envisions also the use of the proteins according to the invention as such, preferably in the form of a fungicidal composition. Fungicidal composition include those in which the protein is formulated as such, but also in the form of host cells, such as bacterial cells, capable of producing the protein thereby causing the pathogen to be contacted with the protein. Suitable host cells may for instance be selected from harmless bacteria and fungi, preferably those that are capable of colonising roots and/or leaves of plants. Example of bacterial hosts that may be used in a method according to the invention are strains of Agrobacterium, Arthrobacter, Azospyrillum, Pseudomonas, Rhizobacterium, and the like, optionally after having been made suitable for that purpose.

Compositions containing antifungal proteins according to the invention may comprise in addition thereto, osmotin-like proteins as defined in WO91/18984. Independently, the invention provides antifungal compositions which further comprise inhibitory agents such as classical fungal antibiotics, SAFPs and chemical fungicides such as polyoxines, nikkomycines, carboxymides, aromatic carbohydrates, carboxines, morpholines, inhibitors of sterol biosynthesis, organophosphorus compounds, enzymes such as glucanases, chitinases, lysozymes and the like. Either per se, or in combination with other active constituents, the antifungal protein of the invention should be applied in concentrations between 1 ng/ml and 1 mg/ml, preferably between 2 ng/ml and 0.1 mg/ml, within pH boundaries of 3.0 and 9.0. In general it is desired to use buffered preparations, e.g. phosphate buffers between 1 mM and 1M, preferably between 10 mM and 100 mM, in particular between 15 and 50 mM, whereby in case of low buffer concentrations it is desired to add a salt to increase ionic strength, preferably NaCl in concentrations between 1 mM and 1M, preferably 10 mM and 100 mM.

Plants, or parts thereof, which relatively over-express a protein according to the invention, including plant varieties, with improved resistance against fungal diseases, especially diseases caused by Oomycetes like Phytophthora and Pythium may be grown in the field, in the greenhouse, or at home or elsewhere. Plants or edible parts thereof may be used for animal feed or human consumption, or may be processed for food, feed or other purposes in any form of agriculture or industry. Agriculture shall mean to include horticulture, arboriculture, flower culture, and the like. Industries which may benefit from plant material according to the invention include but are not limited to the pharmaceutical industry, the paper and pulp manufacturing industry, sugar manufacturing industry, feed and food industry, enzyme manufacturers and the like.

The advantages of the plants, or parts thereof, according to the invention are the decreased need for fungicide treatment, thus lowering costs of material, labour, and environmental pollution, or prolonging shelf-life of products (e.g. fruit, seed, and the like) of such plants. Plants for the purpose of this invention shall mean multicellular organisms capable of photosynthesis, and subject to some form of fungal disease. They shall at least include angiosperms as well as gymnosperms, monocotyledonous as well as dicotyledonous plants.

The phrase "plants which relatively over-express a protein" shall mean plants which contain cells expressing a transgene-encoded protein which is either not naturally present in said plant, or if it is present by virtue of an endogenous gene encoding an identical protein, not in the same quantity, or not in the same cells, compartments of cells, tissues or organs of the plant. It is known for instance that proteins which normally accumulate intracellularly may be targeted to the apoplastic space.

According to another aspect of the invention the regulatory region of a plant gene coding for the antifungal protein of the invention may be used to express other heterologous sequences under the control thereof. The use of a regulatory element of at least 1000 bp directly upstream of the gene coding region is sufficient for obtaining expression of any heterologous sequence.

Heterologous sequences in this respect means gene regions not naturally associated to said regulatory region, and they comprise both different gene coding regions, as well as antisense gene regions. Heterologous coding sequences that may be advantageously expressed in the vascular tissue comprise those coding for antipathogenic proteins, e.g. insecticidal, bactericidal, fungicidal, and nematicidal proteins. In such a strategy it may prove exceptionally advantageous to select a protein with activity against a pathogen or pest which has a preference for phloem as source of nutrients (e.g. aphids), or as entrance to invade the plant. Examples are extensin, lectin, or lipoxidase against aphids (See WO93/04177). Assuming that the regulatory region according to the invention is active in xylem, antifungal proteins may be expressed under the control of said regulatory region to combat Fusarium, Verticillium, Alternaria and Ceratocystus species.

The use of the regulatory region according to the invention may also be used advantageously to regulate or control phloem transport processes. Numerous other applications will readily occur to those of skill in the art.

The expression of part of (part of) an endogenous gene in the antisense orientation (such as disclosed in EP 0 233 399 A), can effectively down-regulate expression of said endogenous gene, with interesting applications. Moreover, the gene encoding the antifungal protein according to the invention itself may be down-regulated using the antisense approach which may help establishing the nature and function of the protein. The regions responsible for tissue-specific expression may be unravelled further using the GUS-marker in a way analogous to the way illustrated herein.

The following state of the art may be taken into consideration, especially as illustrating the general level of skill in the art to which this invention pertains.
EP-A 392 225 A2; EP-A 440 304 A1; EP-A 460 753 A2; WO90/07001 A1; U.S. Pat. No. 4,940,840.

Yet another part of the invention is directed at the production of a novel oxidative enzyme, capable of oxidising carbohydrates even at low concentrations due to its low Km. Most specifically hexoses are the substrate of the enzymatic activity although also other sugars are affected to some lesser extent. The enzymes can be isolated from the sources in which they naturally occur (according to the method described in this invention) or they can be isolated from plants or other organisms transformed with an expressible gene encoding the protein. These oxidases can be used in industrial processes for the oxidation of carbohydrates, such as glucose, mannose, galactose, cellobiose, maltose and lactose.

Evaluation of Transgenic Plants

Subsequently transformed plants are evaluated for the presence of the desired properties and/or the extent to which the desired properties are expressed. A first evaluation may include the level of expression of the newly introduced genes, the level of fungal resistance of the transformed plants, stable heritability of the desired properties, field trials and the like.

Secondly, if desirable, the transformed plants can be crossbred with other varieties, for instance varieties of higher commercial value or varieties in which other desired characteristics have already been introduced, or used for the creation of hybrid seeds, or be subject to another round of transformation and the like.

Synergy

The combination of one of the antifungal protein according to the instant invention and other antifungal proteins of plant or microbial source are predicted to show a drastic synergistic antifungal effect. Similar synergistic antifungal effects were shown if combinations of antifungal CBPs or Chi-V are combined with either β-1,3-glucanases or chitinases from other plant origins. Apparently, the synergizing effect of combinations of pathogen induced proteins is a more general phenomenon that has important consequences for the engineering of fungal resistant plants.

Plants, or parts thereof of commercial interest, with improved resistance against phytopathogenic fungi can be grown in the field or in greenhouses, and subsequently be used for animal feed, direct consumption by humans, for prolonged storage, used in food- or other industrial processing, and the like. The advantages of the plants, or parts thereof, according to the invention are the decreased need for fungicide treatment, thus lowering costs of material, labour, and environmental pollution, or prolonged shelf-life of products (e.g. fruit, seed, and the like) of such plants.

Experimental Part

Standard methods for the isolation, manipulation and amplification of DNA, as well as suitable vectors for replication of recombinant DNA, suitable bacterium strains, selection markers, media and the like are described for instance in Maniatis et al., molecular cloning: A Laboratory Manual 2nd. edition (1989) Cold Spring Harbor Laboratory Press; DNA Cloning: Volumes I and II (D. N. Glover ed. 1985); and in: From Genes To Clones (E. L. Winnacker ed. 1987).

In Vitro Antifungal Assay

All fungi were cultured on potato dextrose agar (Difco) at 25° C., except *Botrytis cinerea* and *Phoma lingam* which were grown on oat meal agar (Difco) at 25° C. *Phytophthora infestans* was grown on rye agar at 18° C. in the dark (Caten and Jinks, 1968). *Botrytis cinerea* and *Phoma lingam* were cultivated under UV. Spores of sporulating fungi were harvested by flooding the agar plates with water. The spore concentration was adjusted to 10,000 sp/mL. In the case of *Rhizoctonia solani* and *Pythium ultimum* liquid shake cultures were grown in potato dextrose broth at 25° C. To prepare inoculum from these shake cultures, mycelium was harvested and vortexed for 1 minute. After passage through a fine sieve, inoculum density was adjusted to 2500–5000 fragments, of 1 to 3 cells each, per mL.

In case of sporulating fungi, all were tested both with and without pregerminating the spores before application of the protein samples. In case of non-sporulating fungi, hyphal fragments were used.

The antifungal activity was monitored during purification in a microtiter plate assay using the fungi *Phytophthora infestans* and *Pythium ultimum* according to Woloshuk et al., 1991 or using other fungi in a similar way. In each well of a 24-well microtiter dish 250 μl potato dextrose agar (PDA) was pipetted. Fungal spores in the case of e.g. *Phytophthora infestans* and hyphal fragments in the case of e.g. *Pythium ultimum* were suspended in water and 400–600 spores or 200 fragments in 50 μl were added to the wells. Subsequently 100 μl filter sterilized (0.22 μm filter) protein solution (in 50 mM MES, pH 6.0) was added. Microtiter dishes were wrapped with Parafilm and incubated at room temperature. At several timepoints after the initiation of incubation the fungus was monitored microscopically for effects of the added protein. After 2–3 days the mycelium of the growing fungus in the wells was stained with lactophenol cotton blue and the extent of growth was estimated.

GI: growth inhibition; a scale of 0–4 is used, 0=no visible inhibition, 1=weak inhibition (0 to 30%) inhibition, 2=moderate (30 to 60%) inhibition, 3=strong (60 to 90%) inhibition, 4=very strong (100%) inhibition.

EXAMPLE 1

Purification of an Antifungal Protein MS59 from Sunflower Induced with Salicylic Acid Leaves of 7 to 8 weeks old sunflower (*Helianthus annuus* cv. zebulon) plants were sprayed daily for 5 times with 10 mM sodium salicylate. After 3 hours the plants were extensively rinsed with water to remove the sodium salicylate. Three days after the final spray, leaves (400 gram) were harvested into liquid nitrogen and homogenized at 4° C. in 500 ml 0.5 M NaOAc pH5.2, and 4 gram active carbon, using a Waring blender. The homogenate was filtered over four layers of cheese cloth and subsequently the filtrate was centrifuged for 50 minutes at 20,000 g at 4° C. and desalted by passage through a Sephadex G25 column (medium course; Pharmacia), length 60 cm, diameter 11.5 cm, equilibrated in 40 mM NaOAc pH5.2. The desalted protein solution was stored overnight at 4° C. and subsequently centrifuged for 45 minutes at 20,000 g at 4° C. The supernatant was passed through a S-sephadex (Fast-flow, Pharmacia) column, length 5 cm, diameter 5 cm, which was equilibrated with 40 mM NaOAc pH 5.2. The column was washed with the above mentioned buffer (flow rate 400 to 500 ml/hr) until the $OD_{280}$ dropped to zero. The bound proteins were eluted using 400 mM NaCl in 200 ml of the above mentioned buffer.

After dialysis against 50 mM MES pH 6.0 the eluate was analyzed for antifungal activity. Antifungal activity was monitored in a microtiter plate assay using the fungus *Phytophthora infestans* and *Pythium ultimum*. See above for details concerning in vitro assaying. Subsequently, cation-exchange chromatography was reapplied whereby the eluate was passed through an FPLC Mono-S HR 5/5 (Pharmacia) and eluted with a linear gradient from 0 to 400 mM NaCl. All fractions were analyzed by electrophoresis (Laemmli (1970), Nature 227:680–685) using a 12.5% polyacrylamide gel in the presence of sodium dodecyl sulphate (SDS), using prestained molecular weight markers (15–105 kDa) as reference. Additionally, of all fractions antifungal activity towards *Phytophthora infestans* and *Pythium ultimum* was monitored. Antifungal activity eluted from the column between 45–60 mM NaCl and in all active fractions a 59 kD band was visible. Fractions containing the antifungal activity were pooled and dialysed to 1 M ammonium sulphate in 50 mM potassium phosphate, pH 7. The pool was subjected to hydrophobic interaction chromatography, whereby the sample was applied to an FPLC Phenyl Superose HR 5/5 (Pharmacia) equilibrated in the same buffer and eluted with a linear decreasing gradient from 1 to 0 M ammonium sulphate in 50 mM potassium phosphate, pH 7. As above again all fractions were analyzed on SDS-PAGE and monitored for antifungal activity. Also the pool of proteins not capable of binding to this column (Flow Through, FT) was thus analyzed at the conditions chosen here. Antifungal activity was present most abundantly in the FT and secondly also in the fractions eluting between 0.76 and 0.45 mM ammonium sulphate. In both cases a 59 kD protein was visible on SDS-PAGE. FT and the gradient fractions were separately dialysed to 50 mM MES, 0.2 M NaCl and separately chromatographed on a FPLC Superdex 75 HR 10/30 column (Pharmacia) equilibrated to the same buffer. Proteins elute from this column according to their molecular size. In both cases again the presence of a 59 kD protein coincided with antifungal activity towards *Phytophthora infestans* and *Pythium ultimum* as judged from SDS-PAGE and in vitro antifungal assays. The 59 kD protein present in the FT of the hydrophobic interaction column was most abundant and termed MS59 and its purification is visualized in FIG. 1. Results of its separation over the gelfiltration column and subsequent analysis both on SDS-PAGE and on *Phytophthora infestans* is shown in FIG. 2. Several characteristics (antifungal activity, chromatographical properties, molecular mass) of the gradient protein and MS59 indicate that the two proteins are very similar.

To characterize MS59 further its amino acid sequence was partially determined. Therefore, MS59 was separated in the presence of 0.1 mM thioglycolate in the upper reservoir buffer and SDS on a 12.5% polyacrylamide gel, which was prerun for 2 hours at 50 V with 0.05 mM glutathione in the upper reservoir buffer. The gel was stained with 5% (w/v) Serva Blue G in 45% (v/v) methanol and 10% acetic acid for 30 minutes and destained in 20% (v/v) acetic acid for 30 minutes and the 59 kDa band was cut out and sequenced using Edman degradation on an Applied Biosystems 477A protein sequencer according to the protocol provided by the manufacturer. N-terminal amino acid sequencing of MS59 revealed that the N-terminus was blocked. To obtain internal sequences, MS59 was digested with trypsin. Trypsin cleaves protein at arginine and lysine residues. The digestion products were separated on a reversed-phase column and analyzed by Edman degradation. Two tryptic fragments were sequenced: Pep1 and Pep2. Of Pep1 25 amino acid residues were identified: S-I-N-V-D-I-E-Q-E-T-A-W-V-Q-A-G-A-T-L-G-E-V-Y-Y-R (SEQ ID NO: 1).

The amino acid sequence is given using the one-letter code. Of Pep2 a further 25 amino acid residues were identified: D-P-S-F-P-I-T-G-E-V-Y-T-P-G-(?)-S-S-F-P-T-V-L-Q-N-Y (SEQ ID NO: 2).

The amino acid residue between brackets could not be identified unambiguously.

EXAMPLE 2

Elution of Antifungal Protein from Native PAGE and Subsequent Testing

Figure 2A:
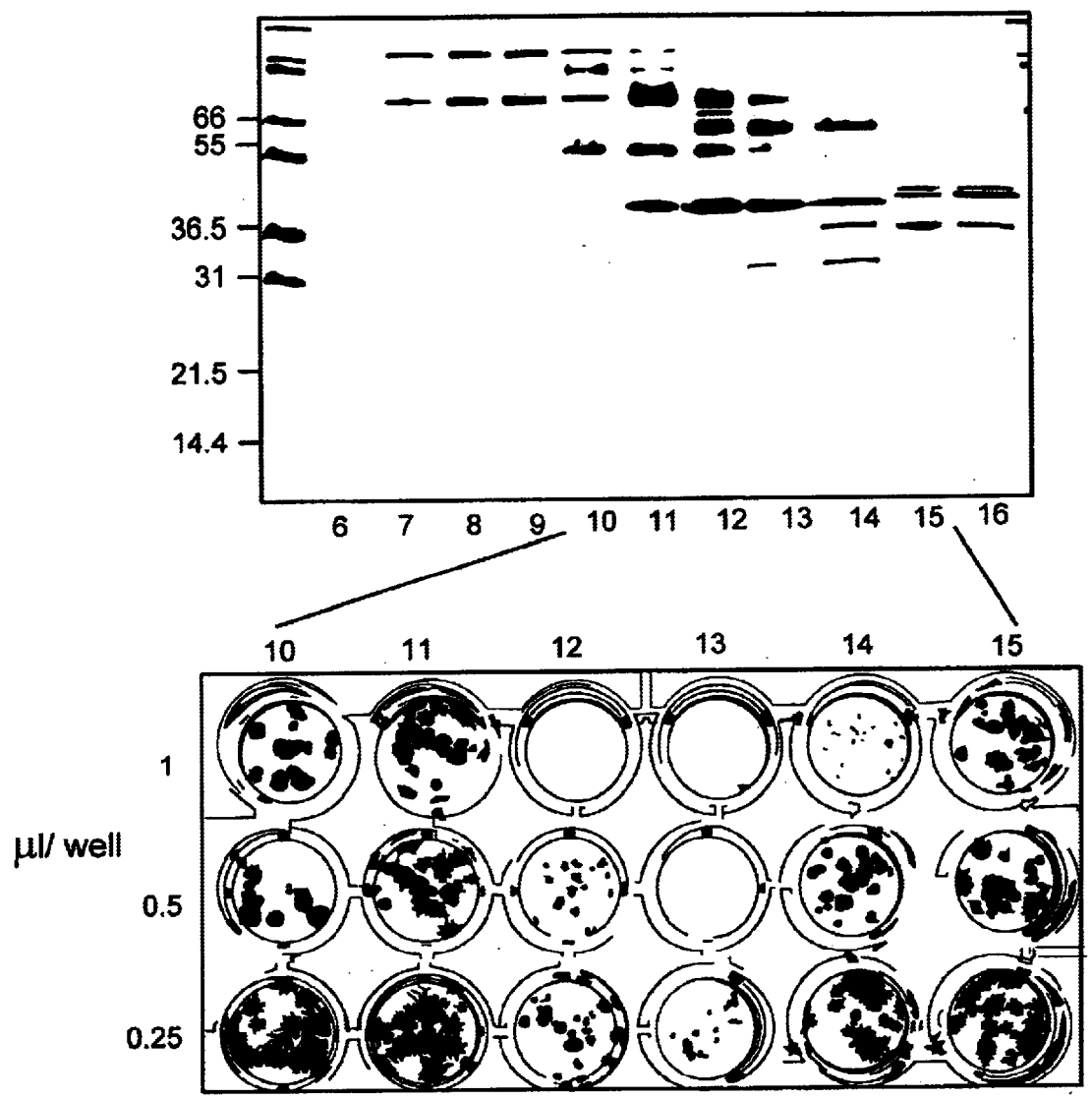
FIG. 2: SDS-PAGE (12.5%) of different fractions (number 6 to 16) of the gelfiltration (SD75) column. Fraction 10 to 15 was tested in 3 dilutions for growth inhibition on *Phytophthora infestans* (PANEL A) and on *Pythium ultimum* (PANEL B)
Figure 2B:
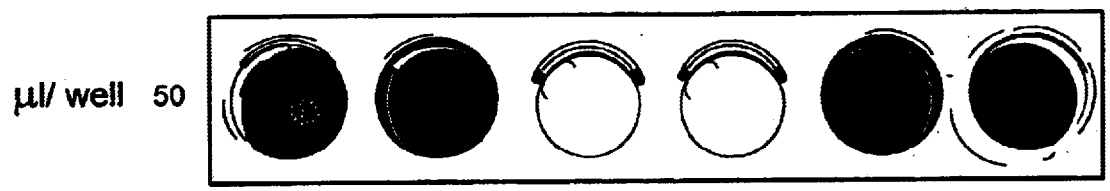
Figure 3:
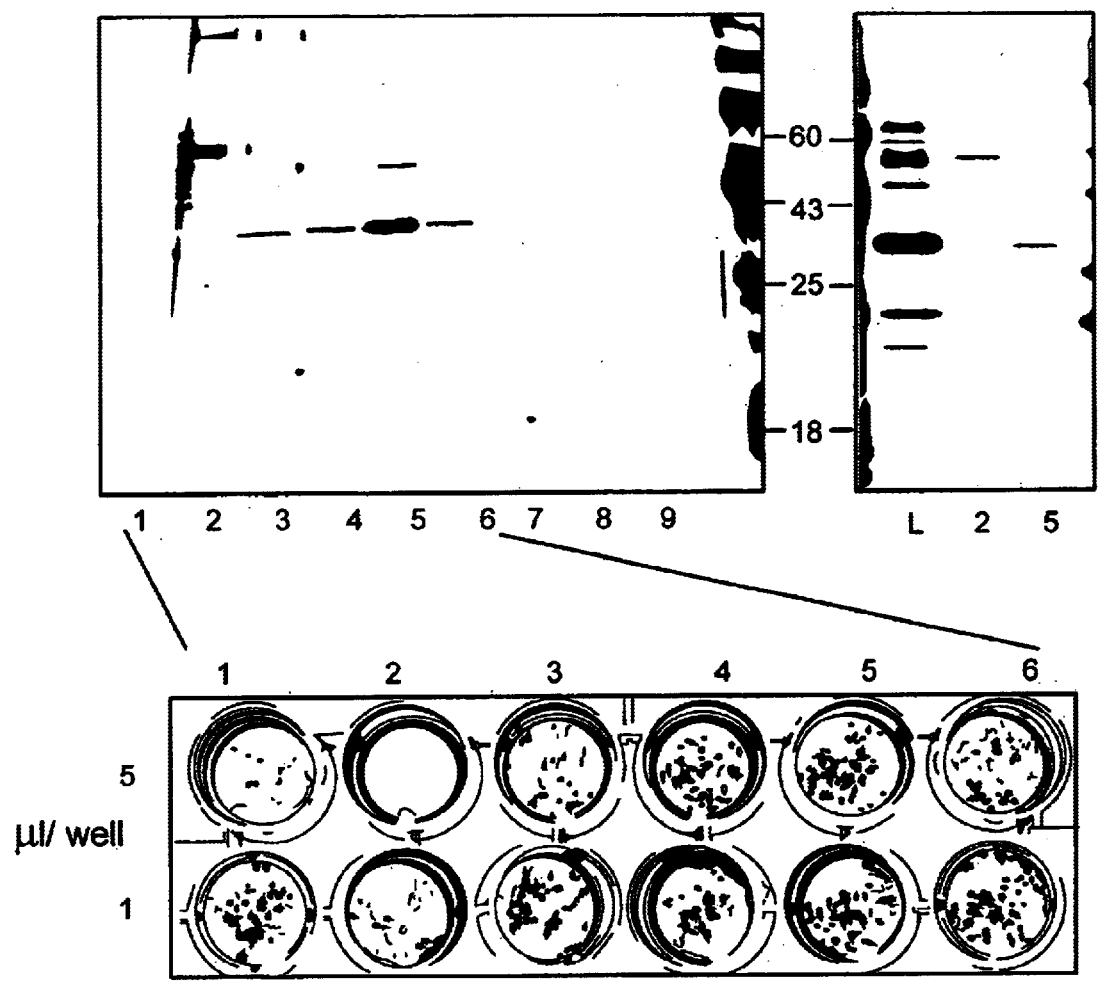
FIG. 3: SDS-PAGE (12.5%) of fractions eluted from nine gel slices (lane 1 to 9) of a native PAGE in which a MS59 containing SD75 fraction (SD75 fraction 13) was separated. Right panel: SDS-PAGE (12.5%) with SD75 fraction 13 (L) and two fractions of elution experiment fraction 2 (with MS59) and fraction 5 (with a ~30 kD protein). Bottom panel: growth inhibition of *Phytophthora infestans* tested with elution fraction 1 to 6, with 5 µl and 1 µl added per well.
Figure 4:
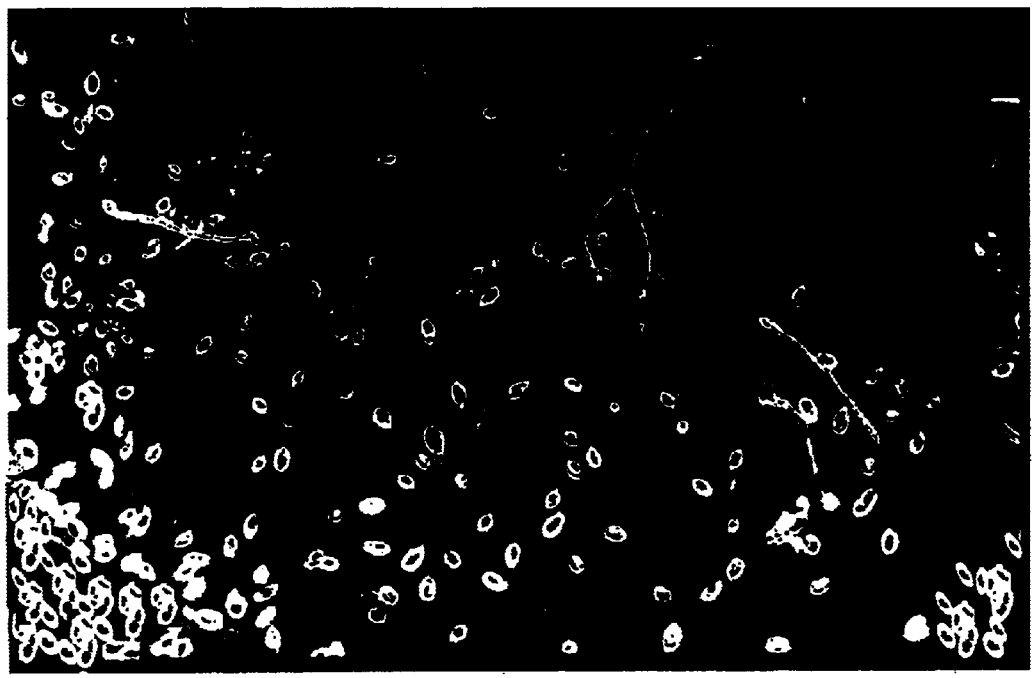
FIG. 4: Microscopical analysis of an in vitro fungal inhibition assay 24 hours after addition of *Phytophthora infestans* zoosporangia to PDA medium. Left panel: control incubation, only MES buffer was added. Right panel: *E. coli*-produced MS59 in MES buffer was added to the incubation.
Figure 4:
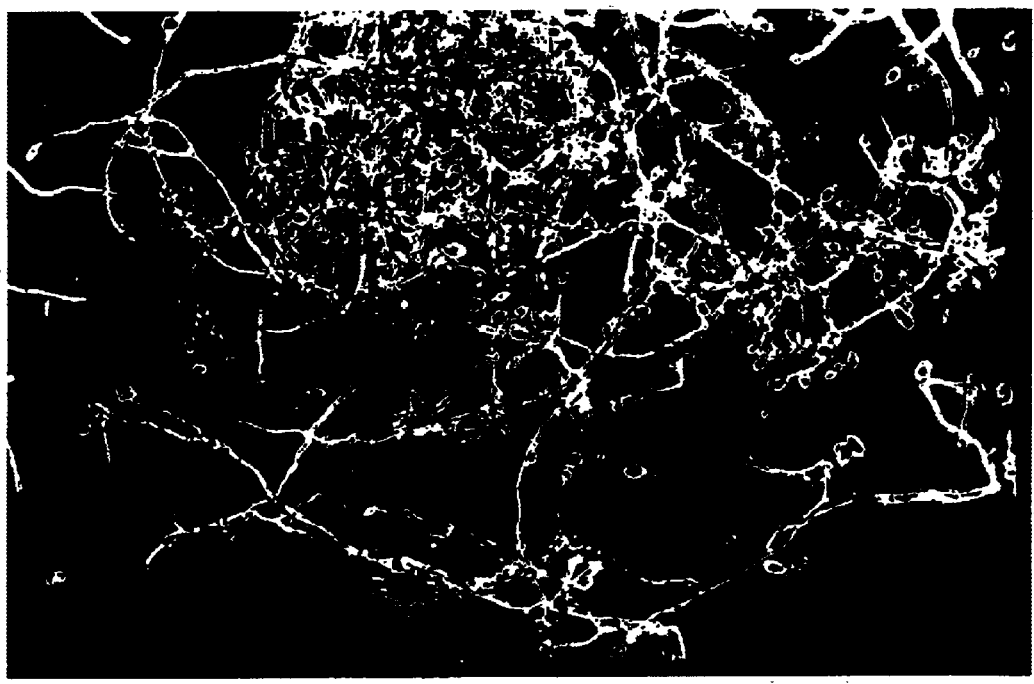
Figure 5:
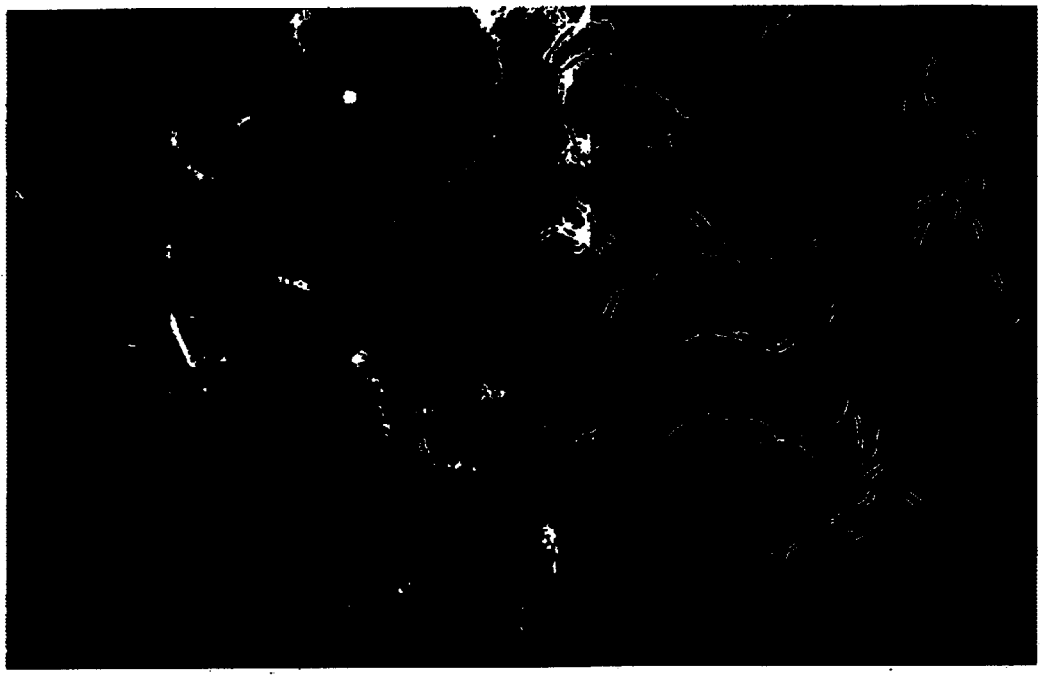
FIG. 5: Microscopical analysis of an in vitro fungal inhibition assay 24 hours after addition of *Pythium ultimum* hyphal fragments to PDA medium. Left panel: control incubation, only MES buffer was added. Right panel: *E. coli*-produced MS59 in MES buffer was added to the incubation.
Figure 5:
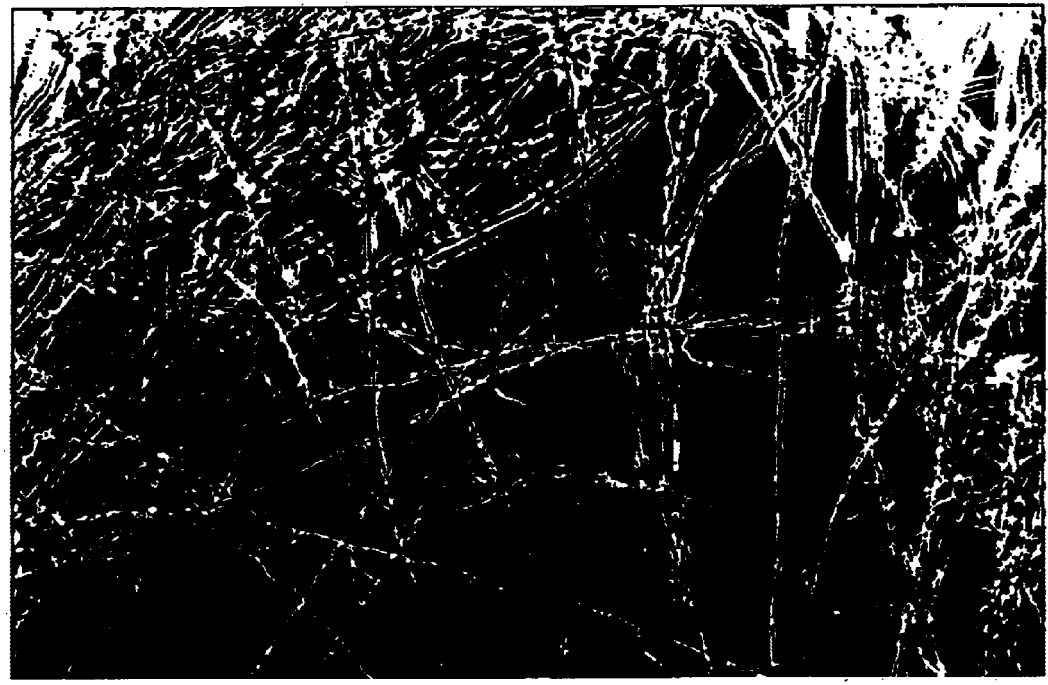

It is obvious from FIGS. 1 and 2 that MS59 is not completely pure. To further ensure that indeed the 59 kDa protein is responsible for the observed antifungal activity, the fraction containing the peak amount of 59 kDa was electrophoresed on a native gel, using the same system as described above however without SDS and without boiling the samples before loading. The gel lane was sliced in 0.5 cm horizontal pieces and each piece was eluted individually for 48 hours in 50 mM Mes, pH 6. After centrifugation the resulting supernatant was analyzed both on SDS-PAGE and in vitro for antifungal activity. Results are shown in FIG. 3. Only in those fractions containing MS59, was antifungal activity observed against *Phytophthora infestans* and *Pythium ultimum*.

EXAMPLE 3

In Vitro Antifungal Assays on Non-Oocym tes

In vitro fungal assays were performed as described in the general experimental part. As positive control *Phytophthora infestans* was tested. The peak of MS59 is located in fraction 4. Results are shown in Table 1.

TABLE 1

Antifungal effects of MS59 containing fractions from Mono-S, pH 6

| fungus | spore stage *) | fraction number | | | | | | |
|---|---|---|---|---|---|---|---|---|
| | | 1 | 2 | 3 | 4 | 5 | 6 | 7/8 |
| *Fusarium oxysporum* | spore | 0 | 0 | 0 | 0 | 0 | 0 | 0 |
| | germl. | 2 | 2 | 2 | 2 | 3 | 3.5 | 3.5 | 3.5 |
| *Fusarium solani* | spore | 0 | 0 | 0 | 0 | 0 | 0 | 0 |
| *Phytophthora infestans* | spore | 0 | 2 | 2 | 4 | 3.5 | 2 | 1 | 0 |
| *Phytophthora nicotianae* | hyph | 0 | 1 | 2 | 4 | 4 | 2 | 1 | 0 |
| *Phytophthora cactorum* | hyph | 0 | 0 | 2 | 4 | 4 | 1 | 1 | 0 |
| *Pythium ultimum* | hyph | 0 | 0 | 0 | 4 | 4 | 0 | 0 | 0 |
| *Pythium sylvaticum* | hyph | 0 | 0 | 0 | 2 | 1 | 0 | 0 | 0 |
| *Pythium paroecandrum* | hyph | 0 | 0 | 0 | 2 | 2 | 0 | 0 | 0 |

*) spore = no pregermination, germl = germination until the germtube is 3–5 times the length of the spore, hyph. = hyphal fragments were used as starting inoculum.
GI: growth inhibition; a scale of 0–4 is used, 0 = no visible growth inhibition, 1 = weak (0 to 30%) inhibition, 2 = moderate (30 to 60%) inhibition, 3 = strong (60 to 90%) inhibition, 4 = very strong (100%) inhibition.

As can be seen Phytophthora and Pythium spp., appeared very sensitive to MS59.

EXAMPLE 4

Purification of an Antifungal Protein WL64 from Lettuce Induced with Salicylic Acid Leaves of 7 to 8 weeks old lettuce (*Lactuca sativa* cv. Lollo bionda) plants were sprayed daily with 10 mM salicylate for 4 days. After two hours the plants were extensively rinsed with water to remove the sodium salicylate. On day 5, the leaves were harvested into liquid nitrogen and stored at −80° C. until further use.

Lettuce leaves were thawed and homogenized at 4° C. in 0.5M NaOAc pH 5.2, 0.1% β-mercaptoethanol (lettuce:buffer=1:1.5 (w/v)), and 10 grams active carbon per kg leaves, using a Waring blender. The homogenate was centrifuged for 60 minutes at 9,000 g at 4° C. The supernatant was subsequently filtered over 10 layers of cheese cloth. The filtrate was brought to 40% saturation with ammonium sulphate and centrifuged for 30 minutes at 9,000 g. The resulting supernatant, containing 85% of protein and >95% of antifungal activity relative to the crude homogenate, was subjected to hydrophobic interaction chromatography.

The supernatant was filtered over a paper filter and applied to a phenyl-sepharose 6FF High sub column (Pharmacia, 100 ml bed volume in a Pharmacia XK 50/20 column) pre-equilibrated with 40% (1.45M) ammonium sulphate in 50 mM potassium-phosphate buffer, pH 6.0 (referred to as buffer A) at a flow rate of 10 ml/min or less. The column was washed with at least 10 column volumes of buffer A after which bound protein was eluted with a decreasing salt gradient from 100% buffer A to 20% buffer A (50 mM KPi pH 6.0 as buffer B) over a period of 40 min at a flow rate of 10 ml/min, followed by a linear decreasing gradient from 20% A to 0% A (=100% B) over a period of 30 min at the same flow rate. The column was washed for another 45 min with buffer B, after which the eruption was completed. One-minute fractions were collected (10 ml/fraction). Fractions 40–75 (called the HIC-peak) contained antifungal activity.

The pooled fractions were concentrated (using a stirred flow cell and a YM 30 kDa membrane (Amicon)) and subsequently 15 times diluted with 25 mM sodium acetate, pH 4.5. This solution was applied to a pre-packed Source S column (16/20, Pharmacia) with a flow rate of 10 ml/min. After washing of the column with 5 column volumes of said buffer, protein was eluted from the column with an increasing NaCl gradient (0–0.4M NaCl in 25 mM NaOAc, pH 4.5) over a 60 min period, 2.5 ml/min, 1 min fractions. Fractions were collected in 250 μl 1M potassium phosphate, pH 7.0, in order to neutralize the relatively acidic NaOAc buffer. The fractions containing antifungal activity (fractions 25–45 (0.2–0.3M NaCl)) were pooled and are referred to as the Source S-peak.

The Source S-peak was concentrated and buffer exchanged to 25 mM NaOAc, pH 4.5, resulting in a fraction of about 10 ml, and subjected to cation-exchange chromatography using a Mono S column (5/5, Pharmacia). The column is eluted with the following NaCl gradients (NaCl in 25 mM NaOAc, pH 4.5): 0–5 min, 0–0.1M NaCl; 5–20 min, 0.1–0.16M NaCl; 20–21 min, 0.16–0.25M NaCl; 21–31 min, 0.25M NaCl; 31–32 min, 0.25–1.0M NaCl, followed by 1.0M NaCl for 10 min after which the elution is completed. The antifungal activity eluted from the column during the 0.25M NaCl step (usually fractions 22–30; the Mono-S peak). Flow-rate 1 ml/min, 1 ml fractions, collected in 100 μl 1M potassium phosphate, pH 7.0.

Figure 6B:
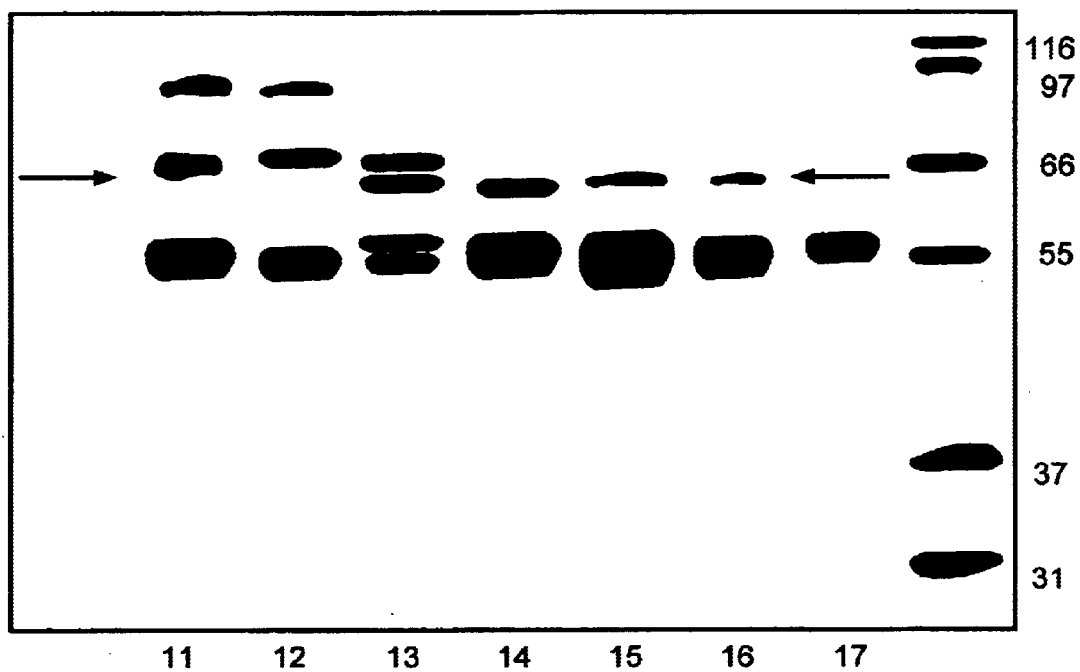
FIG. 6B: Coomassie stained 12.5% SDS-PAGE gel of fractions 11–17 of the SD 75 gelfiltration profile. Molecular weight markers are indicated on the right and are in kDa. The protein bands that correlate with antifungal activity are indicated between the arrows.
Figure 6C:
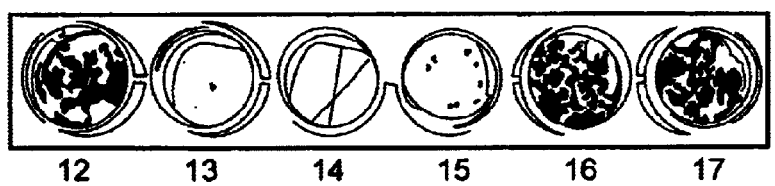
FIG. 6C: In vitro antifungal assay. Ten microlitres of the respective fractions (500 µl total) were used to screen the growth inhibition of *Rhizoctonia solani* hyphal fragments.

The Mono S-peak was concentrated to about 0.5–1.0 ml and subjected to gelfiltration chromatography (Superdex 75, 10/30, Pharmacia), with 200 mM NaCl in 50 mM potassium phosphate, pH 7.0 as the running buffer. The sample volume was 200 μl; flow rate 0.5 ml/min; 0.5 ml/fraction. The antifungal activity elutes from the column at the position of the 66 kDa marker. Comparison of the active fractions (SD 75 peak) with the protein pattern on SDS-PAGE reveals a 64 kDa protein as the most likely candidate for the lettuce-antifungal protein (FIGS. 6A–C). This protein was named WL64.

Figure 7:
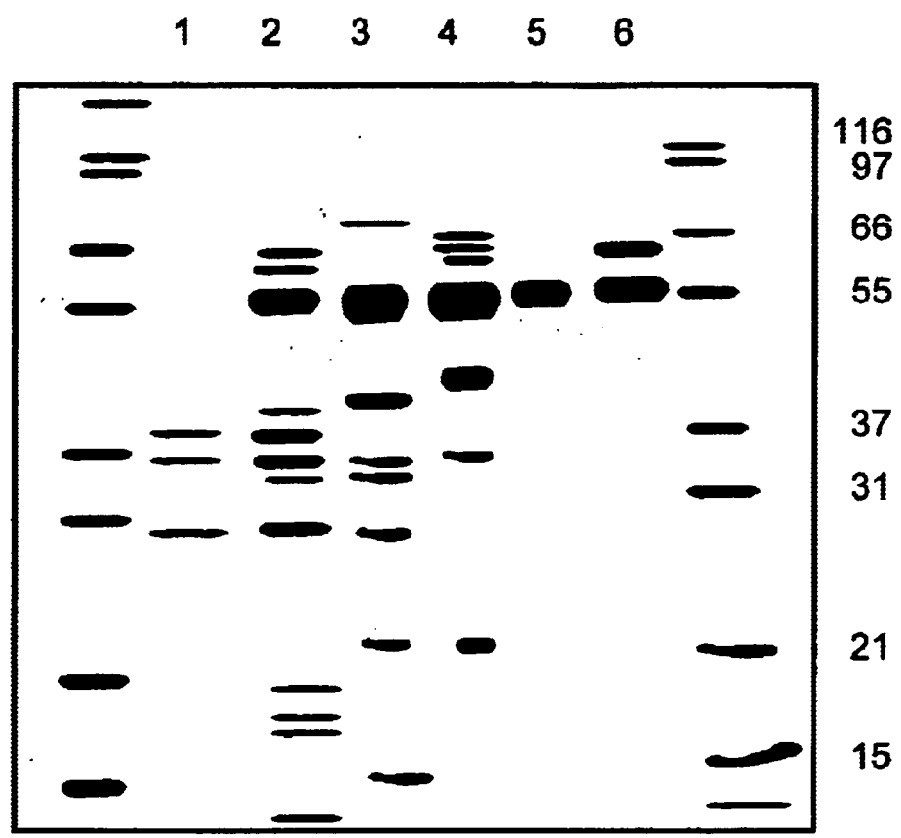
FIG. 7: Coomassie stained 12.5% SDS-PAGE gel of the purification of WL64. Lane 1, lettuce extract; lane 2, HIC peak; lane 3, Source S peak; lane 4, Mono S peak; lane 5, SD 75 peak; lane 6, Mono P peak. Molecular weight markers are indicated on both sides of the figure and are in kDa.

The SD 75-peak was buffer-exchanged to pH 9.5 for chromatophocusing on a Mono P column (Pharmacia) according to the manufacturers instructions. All activity was found in the flow-through of the column (even in the case when the column was equilibrated to pH 11.0) although there was some separation (3 overlapping peaks in flow-through). The flow-rate was 0.5 ml/min; 0.5 ml/fraction. The fractions containing the anti-fungal activity were pooled and buffer-exchanged to 50 mM MES, pH 6.0. Coomassie staining of the highest purified protein fraction after SDS-PAGE revealed about 6 protein bands of which two bands of 64 kDa and 55 kDa, were the most prominent ones (FIG. 7). The estimated relative amounts of both proteins in the final fraction was ⅙–⅛ for the 64 kDa protein and ½–⅓ for the 55 kDa protein. Although on gel it is shown that this column clearly contributes to the purification of the 64 kDa protein, the specific activity, as well as the recovery of the protein in the pooled fractions dropped considerably (see table 2).

A representative purification procedure is summarized in table 2.

TABLE 2

Purification of WL 64

| Sample or Column | Protein (mg) | Activity (GI-units) | Spec. act. (GI-u/mg) | Purification (x-fold) | Recovery (%) |
|---|---|---|---|---|---|
| Lettuce (1.54 kg) | | | | | |
| Extract | 685 | | | | |
| (NH₄)₂SO₄ sup | 584 | 101250 | 173 | 1 | 100 |
| HIC | 174 | 44000 | 253 | 1.46 | 43 |
| Source S | 38.7 | 32400 | 837 | 4.84 | 32 |
| Mono S | 2.3 | 8960 | 3896 | 22.5 | 8.8 |
| SD-75 | 0.452 | 8200 | 18142 | 105 | 8.1 |
| Mono p | 0.137 | 1752 | 12788 | 74 | 1.7 |

The activity is represented as growth inhibition units (GI-units). Four GI units represent the amount of protein that results in a growth inhibition of 100% in the in vitro assay as described in the general part of the Examples.

EXAMPLE 5

Elution of WL64 from Native PAGE and Subsequent Testing

Since WL64 was not completely pure, it was further investigated wether or not the 64 kDa protein was indeed responsible for the observed antifungal activity. The Mono P fraction containing the peak amount of antifungal activity was submitted to electrophoresis on a native 10% polyacrylamide gel under acidic conditions, in the absence of SDS and β-mercaptoethanol and without boiling. Two adjacent gel lanes were sliced in 0.3 cm horizontal pieces. One part was used directly in the antifungal assay, the other part was subjected to SDS-PAGE under denaturing conditions. Growth inhibition clearly correlated to the 64 kDa protein and not to the 55 kDa protein.

EXAMPLE 6

Glycosylation of WL64

WL64, as well as the 55 kDa protein are glycosylated as illustrated by binding to concanavalin A and by the DIG- Glycan-detection kit (Boehringer). Both proteins were not sensitive to glycopeptidase-F treatment, indicating that the glycosylation is probably O-linked.

EXAMPLE 7

Amino Acid Sequencing of WL64

For N-terminal amino acid sequencing an amount of 21 μg of purified protein (representing about 4 μg WL64) was separated on a 7.5% polyacrylamide gel and was subsequently blotted onto PVDF membrane. The membrane was stained with 0.1% Serva Blue G in 45% methanol, 10% acetic acid for 5 minutes at room temperature and destained with 45% methanol, 10% acetic acid. The 64 kDa band was cut out and sequenced using Edman degradation on an Applied Biosystems 477A protein sequencer according to the protocol provided by the manufacturer.

For internal protein sequencing 105 μg of purified protein (representing about 20 μg WL64) was separated on a 7.5% SDS-polyacrylamide gel. The gel was stained with 0.2% Serva Blue G in 20% methanol, 0.5% acetic acid for 20 min at room temperature and destained with 30% methanol at room temperature for about 1 hour. The 64 kDa band was cut out and the protein was subsequently digested with trypsin. The digestion products were separated on a reverse phase column and analyzed by Edman degradation.

Besides the N-terminal sequence (SEQ ID NO: 49), two tryptic fragments were sequenced (SEQ ID NO: 50 and SEQ ID NO: 51).
SEQ ID NO: 49: Thr-Ser-Thr-Ser-Ile-Ile-Asp-Arg-Phe-Thr-Gln-(Cys/Ser)-Leu-Asn-Asn-Arg-Ala-Asp-Pro-(Ser)-(Phe)-
SEQ ID NO: 50: (Ser)-Ile-(???)-Val-(Ser)-Ile-Glu-Asp-Glu-Thr-Ala-(Trp)-Val-Gln-Ala-Gly-Ala-Thr-Leu-Gly-Glu-Val-Tyr-(Tyr)-
SEQ ID NO: 51: Ala-Asp-Pro-Ser-Phe-Pro-Leu-Ser-Gly-Gln-Leu-Tyr-Thr-Pro- The amino acid residues between brackets could not be identified unambiguously.

EXAMPLE 8

Anti-fungal Activity of MS59 and WL64

Based on the sequence homology between MS59 and WL64, both proteins appear to be very related to each other. This might also be the case for their anti-fungal activity, as well as for their specific activities towards the respective fungi. This hypothesis was tested and the results are summarized in table 3.

TABLE 3

Anti-fungal activity of MS59 and WL64[1]

| Pathogen | Amount of WL64 needed for complete inhibition (GI 4) (ngram per assay) | Amount of MS59 needed for complete inhibition (GI 4) (ngram per assay) |
| --- | --- | --- |
| Phytophthora infestans | 10 | 5 |
| Pythium ultimum | 10 | 5 |
| Rhizoctonia solani | 20 | 10 |
| Tanatephorus cucumeris | 20 | n.t. |
| Helicobasidium purpureum | 15 | 7.5 |
| Sclerotium cepivorum | 40 | 20 |
| Pichia pastoris | n.t. | 5 |
| Botrytis cinerea | 200 | 10 | n.t. = not tested

TABLE 3-continued

Anti-fungal activity of MS59 and WL64[1]

| Pathogen | Amount of WL64 needed for complete inhibition (GI 4) (ngram per assay) | Amount of MS59 needed for complete inhibition (GI 4) (ngram per assay) |
| --- | --- | --- |

[1]Antifungal assays were carried out as described in the general experimental part.
Note that the amounts of protein were estimated by means of Coomassie staining on SDS-PAGE gels, meaning that the amounts of protein depicted here are indicative, rather than absolute.

EXAMPLE 9

Oxidase Activities

A 50 ml culture of Rhizoctonia solani in potato dextrose broth was extensively sonicated on ice and subsequently centrifuged at 3,000 g for 20 minutes at 4° C. The resulting supernatant was then centrifuged at 25,000 g for 1 hour. The pellet was washed twice with demineralized water and resuspended in 1 ml water containing 1.0% Triton X-100. In this way a fungal cell wall suspension was obtained.

Oxidase activity was measured utilizing the reagent 4-amino-antipyrine (4-AAP), based on Gallo, 1981 (Gallo, Methods in Enzymology, 71:665–668, 1981). A reaction volume of 500 μl contained 50 mM potassium phosphate buffer pH 7.0, 25 μM FAD, 10 mM $NaN_3$, 0.01% Triton X-100, 6 mM 2,4,6,tribromohydroxybenzoic acid, 2 mM 4-AAP, and 10 units horseradish peroxidase. Hydrogenperoxide production was measured at 510 nm. Known amounts of hydrogen peroxide were included for calibration.

WL64, as well as MS59, performed oxidase activities using the fungal cell wall suspension as substrate. Different substances were subsequently tested as possible substrates, a.o. some carbohydrates and amino acids (see example 10). Glucose, and other carbohydrates were found to serve as substrate for the oxidase activity of both MS59 and WL64.

Figure 8A:
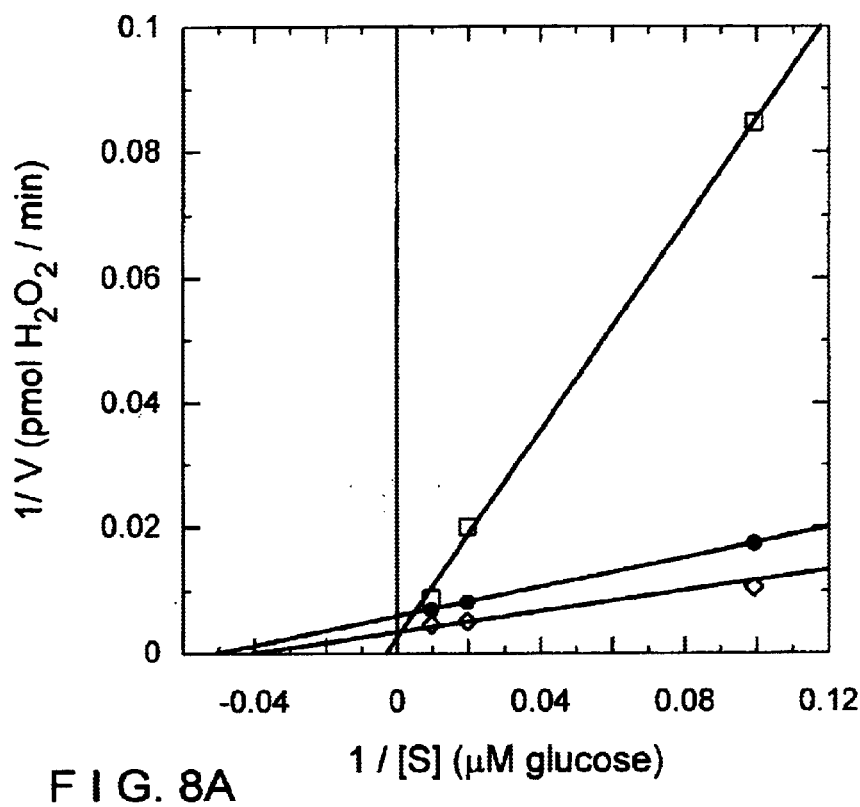
FIG. 8A: Lineweaver-Burk plot of MS59 (open diamonds), WL64 (closed circles), and GOX (open squares) oxidase activities with glucose as substrate. Amounts of protein per assay were 17, 29, and 45 ng for MS59, WL64 and GOX respectively.

Since MS59 and WL64 displayed carbohydrate and especially glucose oxidase activity it was investigated whether the fungal cell wall suspension could serve as a substrate for glucose oxidase (GOX) from Aspergillus niger (Sigma, G 2133). This was indeed the case. Kinetic studies showed that MS59, WL64 and GOX display Michaelis-Menten kinetics when glucose is used as substrate, as illustrated by means of a Lineweaver-Burk plot (FIG. 8A). The $K_m$ values for MS59 and WL64 were more than one order of magnitude lower than that for GOX: 19.5 μM and 23.3 μM for WL64 and MS59 respectively and 359 μM for GOX. This means that the affinity for glucose is much higher for MS59 and WL64 than that of GOX. The $V_{max}$ values were, however, comparable being 5.7, 16.8, and 9.7 μmol $H_2O_2$/min/mg protein for WL64, MS59 and GOX, respectively.

Figure 8B:
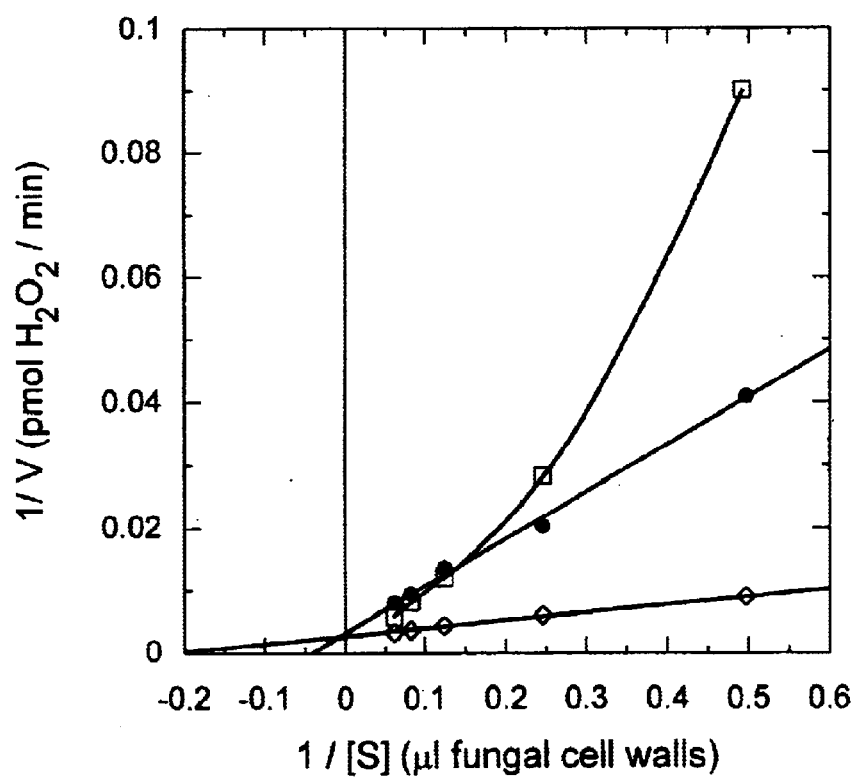
FIG. 8B: Lineweaver-Burk plot of MS59 (open diamonds), WL64 (closed circles), and GOX (open squares) oxidase activities with fungal cell walls as substrate. Amounts of protein per assay were 17, 29, and 225 ng for MS59, WL64 and GOX respectively.

Kinetic studies using the fungal cell wall suspension as substrate showed Michaelis-Menten kinetics for both MS59 and WL64, but not for GOX as shown in FIG. 8B. The $K_m$ values for MS59 and WL64 were 4.7 μl and 24.3 μl respectively, using the suspension described above. The $V_{max}$ values were 22.0 and 11.2 μmol $H_2O_2$/min/mg protein for respectively MS59 and WL64. Since GOX with fungal cell walls as substrate does not show a linear relationship in a Lineweaver-Burk plot, the $K_m$ and $V_{max}$ could not be extrapolated from the plot. The kinetic data are summarized in table 4.

TABLE 4

Kinetic parameters of MS59, WL64 and glucose oxidase

| Enzyme | Glucose | | Fungal Cell Wall Suspension | |
|---|---|---|---|---|
| | $K_m$ ($\mu$M) | $V_{max}$ ($\mu$molH$_2$O$_2$/ min/mg) | $K_m$ ($\mu$l) | $V_{max}$ ($\mu$molH$_2$O$_2$/ min/mg) |
| MS59 | 23.3 | 16.8 | 4.7 | 22.0 |
| WL64 | 19.5 | 5.7 | 24.3 | 11.2 |
| GOX | 359 | 9.7 | | |

EXAMPLE 10

Substrate Specificities

Figure 9:
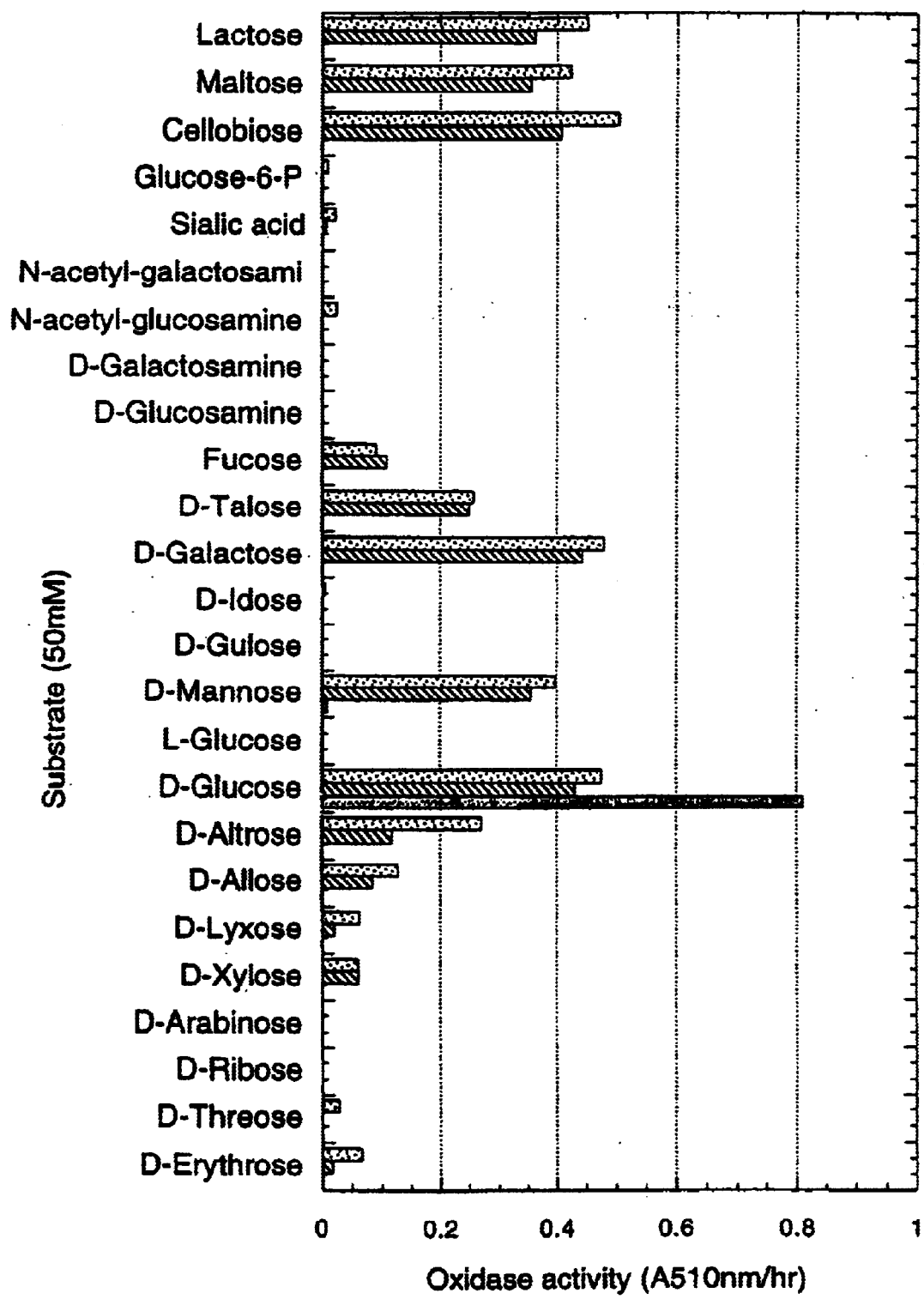
FIG. 9: Substrate specificity for the oxidase activities of MS59 (dotted bars), WL64 (diagonal striped bars), and GOX (filled bars).

Different substances were tested as possible substrates. Among sucrose, sorbitol, fructose, c.m. cellulose, β-alanine, aspartic acid, chitine, cellulose, glutamate, glycine—glycine, laminarin, and glucose, only the latter served as substrate for at least WL64. Concentrations of the various substrates varied between 5 mM and 50 mM. It was further investigated whether glucose was the only substrate for MS59 and WL64 or that other carbohydrates could also be oxidized. The enzyme assays were performed as described in. Example 9, the substrate concentrations being 50 mM. GOX was shown to oxidase glucose exclusively (FIG. 9). Same figure shows that MS59 and WL64 display a much broader substrate specificity, ranging from C$_4$-sugars to di- and polysaccharides. The highest (and almost equal activities) were obtained with D-glucose, D-mannose, D-galactose, cellobiose, maltose, and lactose (FIG. 9). This range of substrates resembles the range found to be converted by hexose oxidase (EC. 1.1.3.5).

EXAMPLE 11

Identification and Characterization of Genes Homologous to the Deduced MS59 Nucleotide Sequence Based on the amino acid sequences of pep1 (a.a. 12 to 22 of SEQ ID NO: 1) and pep2 (a.a. 2 to 12 of SEQ ID NO: 2), primers were designated for PCR. Genomic DNA was isolated from sunflower cv. Zebulon and PCR primers 4 (5'AAC TTC TCC IAG IGT IGC ICC IGC TTG IAC CCA3', SEQ ID NO: 3) and 5 (5'GAT CCI TCT TTC CCI ATT ACT GGI GAG GTT TA3', SEQ ID NO: 4) were used to amplify a 354 bp DNA fragment from the sunflower genome with PCR. PCR products corresponding to this fragment size were cloned (SEQ ID NO: 5). Sequence analysis of the product revealed the presence of an uninterrupted Open Reading Frame (ORF) (SEQ ID NO: 6) of which the first and last stretch of amino acids corresponded with the amino acid sequences of SEQ ID NO: 1 and SEQ ID NO: 2. Several clones sequenced contained point mutations, varying from 1 to 4 in this PCR fragment. All but one of these mutations were silent mutations (nucleotide nr 57 T to C, nucleotide nr 63 C to A, nucleotide nr 225 A to G) which therefore did not alter amino acid sequences encoded. One clone however did contain a point mutation (nucleotide nr 203 G to A) which altered the amino acid sequence at amino acid 68 from Arg to Lys.

A southern blot of sunflower genomic DNA., probed with SEQ ID NO: 5 indicated the existence of multiple homologous sequences in the genome. Using SphI, 6 bands were detected, EcoRV 5 bands, SpeI 3 bands and NdeI 4 bands. With other enzymes 3–4 bands were previously discerned. This analysis suggests the existence of 3 genes with (partial) homology to the ms59 sequences.

New PCR primers were developed based on the non-variable areas between the original PCR primer sequences. Primers: for 3' RACE: 5' CAG GCA GCT GTG GTT TGT GGC 3' (SEQ ID NO: 7), for 5' RACE: 5' GTC CAC AAT GAA GAA GGG TTG 3' (SEQ ID NO: 8) and for nested 3'RACE: 5' ACG TAG ATA TCG AAC AAG AAA CCG C 3' (SEQ ID NO: 9).

Poly(A) containing RNA was isolated from sunflower leaf material that was induced by spraying 5 times with a 10 mM sodium salicylate solution. cDNA was prepared and 5' and 3' RACE PCR reactions were performed as described in the instructions of the Marathon™ kit (Clontech laboratories, Inc., Palo Alto, Calif.). Partial cDNA clones were isolated by 5' and 3' RACE PCR reactions. Sequence analysis confirmed the identity of the partial cDNA clones.

Again new PCR and nested PCR primers were developed based on newly obtained sequence information from cloned 5' and 3' RACE PCR products. Primers for 5'RACE: 5' CTG GGG AAG CCC GTG TAG TAA AGC 3' (SEQ ID NO: 11), 5' CGG GAA GTT GCA GAA GAT TGG GTT G 3' (SEQ ID NO: 13), for nested 5'RACE: 5' GAG CAA GAG AAG AAG GAG AC 3' (SEQ ID NO: 14), for 3' RACE: 5' GCT TTA CTA CAC GGG CTT CCC CAG 3' (SEQ ID NO: 10), and for nested 3' RACE: 5' GGT ACT CCA ACC ACG GCG CTC 3' (SEQ ID NO: 12). Four partial cDNA clones were isolated which together encode all of the Open Reading Frame including a putative signal peptide followed by an approximately 59 kDa protein, and 5' and 3' UTR's (untranslated regions)(SEQ ID NO: 15). A full length cDNA clone of 1784 bp, of which the ORF (pos. 21 to pos. 1608) encodes 529 amino acid residues (SEQ ID NO: 16), could be assembled out of these four partial cDNA clones and the PCR fragment mentioned above (SEQ ID NO: 5).

The amino-terminal signal sequence (Von Heijne et al., 1983 and Von Heijne, 1985) is not likely fully presented within the first 19 amino acid residues. A prediction of the putative cleavage site was made.

The amino acid sequence of this cDNA clone was used in a BLAST homology search. This sequence revealed high homology to the Berberine Bridge Enzymes (BBE) from Californian poppy (*Eschscholtzia californica*) (Dittrich and Kutchan, 1991, Proc. Natl. Acad. Sci. USA 88, 9969–9973) and Opium poppy (*Papaver somniferum*) (Facchini et al., 1996, Plant Physiol. 112, 1669–1677).

BLAST screening of Expressed Sequence Tag (dbEST) databases with the amino acid sequence as shown in SEQ ID NO: 16 revealed homologues of the MS59 protein in *Arabidopsis thaliana* (SEQ ID NO: 21 to SEQ ID NO: 47) and rice (SEQ ID NO: 48).

The EST sequences are listed in the sense orientation considering the orientation of homology to MS59. Sequences of the EST clones were altered by inserting one or two extra unknown nucleotides (N or NN) at frameshift positions in order to obtain one single translation frame with homology to MS59.

EXAMPLE 12

Isolation of the Gene Encoding WL64 and Determination of the Nucleotide Sequence Based on the amino acid sequence of the amino-terminus of the WL64 protein (SEQ ID NO: 49, Thr-Ser-Thr-Ser-Ile-Ile-Asp-Arg-Phe-Thr-Gln-(Cys/Ser)-Leu-Asn-Asn-Arg-Ala-Asp-Pro-(Ser)-(Phe)-) a primer (a.a. 1 to 11 of SEQ ID NO: 49) was developed for PCR.

The N-terminal amino acid sequence (SEQ ID NO: 49) revealed high homology to the corresponding portion of the MS59 protein (amino acid residues 20 to 39 in SEQ ID NO: 16).

cDNA was prepared from Poly(A) containing RNA that was isolated from lettuce (*Lactuca sativa* cv. Lollo bionda) leaves that were induced by spraying 5 times with a 10 mM sodium salicylate solution. PCR primers FR-WL64–142 (5'ACT TCT ACT TCT ATT ATT GAT AGG TTT ACT CA3', SEQ ID NO: 52) and MS59 primer 4 (5'AAC TTC TCC IAG IGT IGC ICC IGC TTG IAC CCA3', SEQ ID NO: 3) were used to amplify a 405 bp fragment from the lettuce cDNA pool. PCR products corresponding to this PCR fragment were cloned and sequenced (SEQ ID NO: 53) and revealed an uninterrupted open reading frame (SEQ ID NO: 54).

TABLE 5

EST sequences showing homology to MS59.
Frameshifts were introduced for optimal aligning of the EST's with the MS59 sequence. In the columns with frameshift 1 and frameshift 2 the position of the frameshift and the shift (frame ---> frame) are listed.
The (—) mark means, no frameshift present.

| SEQ ID NO: | EST name | GenBank accession | Frame (1, 2, 3) | Frameshift 1 | Frameshift 2 |
|---|---|---|---|---|---|
| 21 | ATTS5925 | F19886 | 2 | — | — |
| 22 | ATTS0345 | Z17771 | 2 | 202, 2 ---> 1 | — |
| 23 | ATTS5268 | F14356 | 2 | 298, 2 ---> 3 | — |
| 24 | TC13883 | — | 1 | 177, 1 ---> 2 | — |
| 25 | TC11550 | — | 2 | — | — |
| 26 | P_16053 | R84094 | 1 | — | — |
| 27 | P_22214 | N97049 | 2 | 310, 2 ---> 3 | — |
| 28 | P_16873 | R90518 | 3 | 317, 3 ---> 2 | — |
| 29 | ATTS2532 | Z30784 | 3 | 188, 3 ---> 1 | 312, 1 ---> 2 |
| 30 | TC11456 | — | 3 | — | — |
| 31 | P_8818 | T45555 | 1 | 98, 1 ---> 3 | — |
| 32 | P_21340 | N96011 | 1 | — | — |
| 33 | P_22585 | W43206 | 2 | 367, 2 ---> 1 | — |
| 34 | Q_ATTS2533 | Z30785 | 2 | — | — |
| 35 | P_17333 | H76902 | 2 | — | — |
| 36 | P_9615 | T46352 | 1 | — | — |
| 37 | Q_ATTS2959 | Z33920 | 2 | — | — |
| 38 | P_2730 | T20722 | 1 | — | — |
| 39 | TC9870 | — | 2 | — | — |
| 40 | P_14876 | H36354 | 2 | 241, 2 ---> 1 | — |
| 41 | P_21353 | N96040 | 1 | 89, 1 ---> 2 | — |
| 42,43 | Q_ATTS3343 | Z34583 | 1 | — | — |
| 44 | Q_ATTS4954 | F14032 | 2 | 139, 2 ---> 1 | — |
| 45 | Q_ATTS1606 | Z26512 | 2 | — | — |
| 46 | P_7866 | T44603 | 1 | 222, 1 ---> 3 | — |
| 47 | AA0410042 | 24308 | 2 | 421, 2 ---> 1 | — |
| 48 | RICS2381A | D40415 | 3 | — | — |

New PCR primers were developed based on the sequence of SEQ ID NO: 53 that is located between the original PCR primers. Primers for 5' RACE: 5'CAC GTT TAT GGA GCG TAA GTT GAA C3' (SEQ ID NO: 55) and for 3' RACE: 5'CAC CCT TCA CAC ATT CAA GCA GC3' (SEQ ID NO: 56) were synthesized and used in 5' and 3' RACE PCR reactions, performed as described in the instructions of the Marathon™ cDNA amplification kit (Clontech laboratories, Inc., Palo Alto, Calif.). Two partial cDNA clones were amplified by 5' and 3' RACE reactions. Sequence analysis confirmed the identity of the partial cDNA clones which together encode all of the open reading frame including a putative signal peptide and 5' and 3' UTR's (untranslated regions). A full length cDNA clone of 1981 bp (SEQ ID NO: 57) was assembled of which the ORF (pos. 7 to pos. 1629) encodes 540 amino acid residues (SEQ ID NO: 58). The amino terminal signal sequence is represented by the first 27 amino acid residues.

EXAMPLE 13

Characterization and Isolation of Berberine Bridge Enzyme Genes from *Papaver somniferum* and *Eschscholtzia californica*

Genomic DNA was prepared from leaves of full grown Californian poppy (*Eschscholtzia californica*) and Opium poppy (*Papaver somniferum* cv Marianne) plants.

Primers were designed for the Californian poppy gene (EcBBE) at the start of the mature protein (5' GGT AAT GAT CTC CTT TCT TGT TTG ACC 3', SEQ ID NO: 59) and at the stop codon introducing a Not I restriction site just downstream of the TAG stop codon (5' AGA GCG GCC GCT ATA TTA CAA CTT CTC CAC CAT CAC TCC TC 3', SEQ ID NO: 60).

For the Opium poppy gene (PsBBE) primers were designed in a similar way at the start of the presumed mature protein (5' GGT GAT GTT AAT GAT AAT CTC CTC 3', SEQ ID NO: 61) and at the TAG stop codon introducing a Not I restriction site (5' AGA GCG GCC GCT ACA ATT CCT TCA ACA TGT AAA TTT CCT C 3', SEQ ID NO: 62).

These primers were used to amplify the mature portion of both the BBE genes.

The PCR products were digested with Not I and ligated into vector pET32a (Novagen, Madison, Wis.) digested with EcoR V and Not I. The correct insertion of the fragment was confirmed using restriction enzyme analysis and DNA sequencing.

EXAMPLE 14

Characterization and Isolation of MS59 Homologues from *Arabidopsis thaliana*

In our blast screening we identified 26 EST's with homology to MS59. One EST was found in Rice and the remaining 25 were all found in *A. thaliana*. Homologous EST's were found over the entire length of the MS59 sequence. Analysis of the Arabidopsis expressed sequence tags revealed that there are 3 EST's with high homology at the 5' end of the protein (SEQ ID NO: 21, SEQ ID NO: 39 and SEQ ID NO: 40) of which SEQ ID NO: 39 and SEQ ID NO: 40 are overlapping sequences. The 3' part of MS59 showed homology to 7 EST sequences (SEQ ID NO: 24, 27, 32, 34, 41, 43 and 45) of which SEQ ID NO: 24 is overlapping with SEQ ID NO: 43 and SEQ ID NO: 32 is overlapping with SEQ ID NO: 45.

Primers were designed, located at the start of the presumed mature part (possible cleavage sites were predicted according to consensus sequences described by Von Heijne et al., 1983 and Von Heijne, 1985) of the two different EST's homologous with the 5' part of MS59 (SEQ ID NO: 16).

The EST sequence represented by SEQ ID NO: 21 possibly missed the first three amino acid residues of the predicted mature part when compared to the MS59 amino acid sequence (SEQ ID NO: 16) and, therefore, A.a. residues 20 to 22 of SEQ ID NO: 16 were introduced by including 9 nucleotides at the 5' end of the primer.

Primer located 5' in SEQ ID NO: 21, adding residues 20 to 22 of MS59 (SEQ ID NO: 16): 5' ACT TCC CGT AGA AAC TCG GAG ACT TTC ACA CAA TGC 3' (SEQ ID NO: 63).

Primer located behind the predicted cleavage site of SEQ ID NO: 39 and SEQ ID NO: 40:5' TCC ATC CAA GAT CAA TTC ATA AAC TGT GTC (SEQ ID NO: 64).

Primers were also made located around the stopcodon of the five different EST's homologous with the 3' part of the MS59 a.a. sequence (SEQ ID NO: 16) and introducing a Not I restriction site for cloning in the pET32a *E. coli* expression vector.

Primer located in SEQ ID NO: 24 and SEQ ID NO: 43, 5' AGA GCG GCC GCT TTC ATG AAC CTA GCT TCT AGT AGG 3' (SEQ ID NO: 65). Primer in SEQ ID NO 27, 5' AGA GCG GCC GCG AAA TGG CCC CCC TTT TAA AAC GGG G 3' (SEQ ID NO: 66). Primer in SEQ ID NO: 32 and SEQ ID NO: 41, 5' AGA GCG GCC GCA AAT GAT ATC TTC AGG TAA CTT TGT TCA C (SEQ ID NO: 67). Primer in SEQ ID NO: 34, 5' AGA GCG GCC GCA TAA TCA AAT AAA TAC ACT TAT GGT AAC ACA G (SEQ ID NO: 68) and the primer in SEQ ID NO: 45, 5' AGA GCG GCC GCT GGT TTT GTA TTG AGG ACT CAA AAC AG 3' (SEQ ID NO: 69).

All possible combinations of the 5' primers with the 3' primers were used in a PCR on genomic DNA isolated from *Arabidopsis thaliana* cv Columbia. In a PCR with the primers SEQ ID NO: 63 and SEQ ID NO: 68 an approximately 1800 bp band was amplified. This band was cloned and identity of the PCR product was confirmed by DNA sequencing. The cloned PCR product of 1757 bp (SEQ ID NO: 70) contained an intron from position 570 to position 801, the open reading frame of SEQ ID NO: 70 consists of 508 amino acid residues (SEQ ID NO: 71).

Total RNA was isolated from *Arabidopsis thaliana* Col-0 from 12 days old sterile etiolated seedlings grown in the dark on Murashige and Skoog agar, from 12 days old sterile seedlings grown in liquid Murashige and Skoog medium with a 16 hour photoperiod and from leaves, stems, flowers and siliques from full grown plants (Newman et al., 1994 Plant Physiol. 106:1241–1255). The RNA from the different developmental stages was pooled. Poly(A)+ RNA was isolated using the Poly(A) Quick® mRNA Isolation kit (Stratagene, La Jolla, Calif.) and cDNA was prepared using the Marathon™ cDNA Amplification Kit (Clontech Laboratories Inc., Palo Alto, Calif.).

PCR reactions were set up with the cDNA pool with different combinations of 5' primers and 3' primers. A PCR product was amplified with the primer combination SEQ ID NO: 63 and SEQ ID NO: 68 of approximately 1600 bp. The PCR product was cloned in the EcoR V and Not I restriction sites of the bacterial expression vector pET32a (Novagen, Madison, Wis.). The sequence of the PCR product was determined and revealed an uninterrupted open reading frame of 1527 bp (SEQ ID NO: 72) representing a protein of 508 amino acid residues (SEQ ID NO: 73).

A second cDNA clone of about 1600 bp was amplified with the primer combination SEQ ID NO: 64 and SEQ ID NO: 65. This cDNA clone was also ligated into the EcoR V and Not I restriction sites of pET32a (Novagen, Madison, Wis.). This cDNA PCR clone was also characterized by DNA sequencing and consisted of an uninterrupted open reading frame of 1530 bp (SEQ ID NO: 74) encoding 509 amino acid residues (SEQ ID NO: 75).

EXAMPLE 15

Expression of MS59, the Berberine Bridge Enzymes from *Papaver somniferum* and *Eschscholtzia californica* and Two Homologous Proteins from *Arabidopsis thaliana* cv Columbia in *E. coli*

A PCR fragment containing the presumed mature portion of MS59 was introduced in vector pET32c (Novagen, Madison, Wis.), and the correct insertion of the fragment is confirmed using DNA sequencing. Then, the plasmid was introduced into *E. coli* AD494 (DE3) pLysS (Novagen, Madison, Wis.). Small scale cultures (2 ml) of several colonies were then started of which half is induced by the addition of IPTG to 1 mM final concentration. Total extracts from *E.coli* were run on SDS gels and analyzed by Coomassie Brilliant Blue staining. Several clones exhibited strong overexpression of the MS59 protein. A clone which had strong overexpression was selected for a large scale culture. Five hundred ml of LB supplemented with 0.4 mM glucose was inoculated with a culture of this *E. coli* and grown to an optical density of 0.5–0.7. Then, IPTG was added to a final concentration of 1 mM and protein production allowed for 3 hours at 30° C. A large proportion of the MS59 protein was found in the insoluble protein fraction, a small amount appeared soluble. The resulting insoluble protein preparation contained mainly MS59 protein. This preparation is used for raising antibodies (Example 17). The soluble fraction was used in an in vitro assay to test whether the MS59 protein still exhibited antifungal activity.

The pET32a plasmids containing the open reading frames of the four MS59/WL64 homologues were introduced into *E.coli* AD494(DE3)pLysS (Novagen, Madison, Wis.). Small scale cultures (25 ml) of several independent clones were grown to an optical density of 0.5–0.7. Then IPTG was added to a final concentration of 1 mM and protein production was allowed for 4 hours at 30° C.

Soluble and total protein fractions were isolated. The samples were analyzed using SDS-PAGE followed by Neuhoff staining and Western analysis using the S-Tag Western Blotting detection kit (Novagen, Madison, Wis.). A large portion of the protein was found in the insoluble fraction, only a small amount appeared to be soluble. Clones which strongly overexpressed the homologous proteins were selected for production of the proteins in large scale cultures of 1.5 liter each.

EXAMPLE 16

In Vitro Antifungal Assays of MS59, MS59/WL64 Homologues from Californian poppy (*Eschscholtzia californica*) and Opium Poppy (*Papaver somniferum*) and Two Homologous Proteins from *Arabidopsis thaliana*

The MS59 protein produced in *E. coli* contained N-terminal trxA-, His- and S-Tags. The His-tag was used for purification of the soluble MS59 on an IMAC (immobilized metal affinity chromatography) column, charged with $Ni^{2+}$. Bound protein was eluted by increasing the imidazole concentration. The peak fraction from this purification contains some contaminating *E. coli* proteins.

The peak fraction of this MS59 purification was dialysed into 50 mM MES, pH 6.0, and used in an in vitro assay with *Phytophthora infestans* and *Pythium ultimum*. For the standard setup of the in vitro antifungal assay with *Phytophthora infestans* and *Pythium ultimum* see above.

As control treatment we assayed an unrelated His-tagged protein purified from the same expression host, with some *E.coli* protein background. Also a boiled MS59 control (heated 10 minutes at 100° C.) was included. Approximately 40 ng of fusion protein was tested in the *Phytophthora infestans* assay, twice that amount was used for the *Pythium ultimum* inhibition assay.

Microtiter dishes were wrapped with Parafilm and incubated in the dark at room temperature. After 2–3 days the mycelium of the growing fungus in the wells was stained with lactophenol cotton blue and the extent of growth was estimated.

IMAC fractions from the soluble fraction of E.coli containing MS59 showed complete inhibition of P.infestans and P.ultimum at concentrations of 20–40 ng.

TABLE 6

Antifungal effects of MS59 from E. coli on Phytophthora infestans

| Fraction | MS59 E. coli | MS59 E. coli boiled | His-protein E. coli | MES buffer |
|---|---|---|---|---|
| Growth inhibition | 4 | 0 | 0 | 0 |
| amount of extract | 5 µl | 5 µl | 5 µl | |

Growth inhibition (GI) is scored visually on a linear scale of 0 (no inhibition) to 4 (complete growth inhibition).

TABLE 7

Antifungal effects of MS59 from E. coli on Pythium ultimum

| Fraction | MS59 E. coli | MS59 E. coli boiled | His-protein E. coli | MES buffer |
|---|---|---|---|---|
| Growth inhibition | 4 | 0 | 0 | 0 |
| amount of extract | 10 µl | 10 µl | 10 µl | |

Microscopical analysis of the wells indicate the rapid germination and subsequent growth of *Phytophthora infestans* zoospores in each of the controls. Germination is near completely inhibited in the reactions containing the MS59 protein from *E. coli*. Some spores do germinate, but hyphal tip growth appears to stop soon after initiation. After 48 hours growth of *Phytophthora infestans* mycelium is abundant in the controls, but almost undetectable in the assay containing MS59. Even after 72 hours no substantial growth is observed. Fungal hyphae appear somewhat granular and thickened in the reactions containing MS59 protein. Examples of the characteristic patterns of fungal growth in incubations with and without *E. coli*-produced MS59 are depicted in FIG. 4. After 48 and 72 hours fungal growth in the control incubations is so extensive no photographic material could be gathered. Incubations in the presence of MS59 leads to complete blockage of further growth, the germination tubes observed at 24 hours do not noticeably extend further.

Likewise, in the *Pythium ultimum* inhibition assay, where mycelium fragments are used, no growth is apparent upon treatment with MS59 (see FIG. 5). After 24 hours the control reactions were completely overgrown by mycelium. Only small mycelium fragments are at that stage apparent in the MS59-treated sample.

The poppy homologues were expressed in *E. coli* (pET32a) and tested for in vitro antifungal activity on *Phytophtora infestans* and *Pythium ultimum. Phytophthora infestans* spores and hyphal fragments of *Pythium ultimum* were suspended in respectively sterile water or potato dextrose broth (PDB). 400–600 spores or 200 fragments/50 μl were added to each well.

The expressed proteins were partially purified by means of IMAC column chromatography. Fractions containing the expressed proteins were buffer exchanged to 50 mM MES, pH 6.0, filter sterilized, and tested for their antifungal activity, with IMAC purified *E. coli* pET32-MS59 as a positive control.

No antifungal activity was observed for both *Eschscholtzia californica* and *Papaver somniferum* MS59/WL64 homologues, not even at concentrations ten times higher than that of the positive control, leading to a 100% growth inhibition of both fungi. This could mean that these *E. coli* expressed proteins did not have the correct folding and therefore showed no biological activity.

EXAMPLE 17

Raising Antibodies Against Denatured MS59

Antibodies were raised in rabbits against denatured MS59 (the solubilized form from the insoluble *E.coli* fraction) in PAG-slices. The antibodies showed cross-reaction with a band of about 60 kDa only in the IF of pMOG1180 (Examples 18 and 19) tobacco plants containing antifungal and glucose oxidase activity. Surprisingly, no cross-reaction with WL64 is found.

EXAMPLE 18

Tailoring a MS59 Clone for Expression in Transgenic Plants

PCR primers were developed based on the sequence around the ATG start codon and the TGA stop codon for cloning of the open reading frame (ORF). A NcoI restriction site was introduced at the ATG start codon for fusion to a constitutive promoter by PCR using primer: 5' CC GCC ATG GAG ACT TCC ATT CTT ACT C 3' (SEQ ID NO: 16). The second codon of the ORF was changed from caa (Q) to gag (E) as a result of the introduced NcoI restriction site. Downstream of the TGA stop codon a BamHI restriction site was introduced by PCR using primer: 5' GCC GGA TCC TCA AGA TGA CAA AGT TGG GAT GCT 3' (SEQ ID NO: 18).

Using a PCR reaction with Pfu DNA polymerase, we amplified the entire ORF, using the PCR primers to introduce the NcoI restriction site on the startcodon ATG and the BamHI restriction enzyme recognition site just downstream of the stopcodon. The integrity of the DNA sequence was confirmed by sequencing (SEQ ID NO: 19). The entire ORF was linked to a constitutive promoter which allows high level protein expression in most parts of the plant. After the ORF a 3' untranslated region of the potato proteinase inhibitor II (Thornburg et al., 1987, Proc. Natl. Acad. Sci. USA 84, 744–748), which contains sequences needed for polyadenylation (An et al., 1989, Plant Cell 1, 115–122), was introduced. The chimeric gene produced was introduced into binary vector pMOG800 (deposited at the Centraal Bureau voor Schimmelcultures, Baarn, The Netherlands, under CBS 414.93, on Aug. 12, 1993). The resulting clone pMOG1180, which harbours the MS59 construct under control of the ocs-mas hybrid promoter (WO95/14098) was introduced in *Agrobacterium tumefaciens* strain EHA105, suitable for transformation of target crops tomato and potato, strain MOG101 for transformation of tobacco and Arabidopsis and MOG301 for transformation of *Brassica napus.*

EXAMPLE 19

Production and Analysis of Transgenic Tobacco and Potato Plants Containing the MS59 Gene Construct Using Agrobacterium mediated transformation system binary constructs containing the MS59 gene construct as described in Example 18 were introduced into tobacco and potato. The transgenic shoots of these different plant species were regenerated into whole plants and subsequently, primary transformants were analyzed for expression of the newly introduced MS59 gene. For this analysis use was made of Western blotting techniques, using antibodies against MS59 specific peptide coupled to BSA. All antisera were diluted 1:5,000. A concentration series of purified proteins (12.5, 25, 50 and 100 ng) was used to judge the expression level of the introduced proteins in the transgenic plants. Transgenic samples were homogenized in 50 mM sodium acetate buffer pH 5.2 and the extracts were clarified by centrifugation. The supernatants were either directly analyzed or left overnight to precipitate on ice. Overnight precipitation was always followed by clarification (by centrifugation). The protein concentration of the supernatants obtained in either way was determined using Bradford reagent (Bradford 1976, Anal. Biochem. 72, 248–254) and BSA as the standard protein. As much protein as possible (but never more than 10 μg) was loaded on a 12.5% SDS-PAA gel (Laemmli, supra) and immunoblotted as previously described (Ponstein et al. supra).

Extracts from leaves of ms59-transgenic tobacco and potato plants were made by pottering leaf fragments in a buffer containing 50 mM NaAc, (pH=5.2). After this, insoluble protein was removed by centrifugation. Total soluble protein content was measured and the equivalent of 10 μg was loaded on a SDS-gel. After running the gel the proteins were transferred to blot. This blot was developed using the antiserum raised against purified MS59 (Example 17). The MS59-specific antiserum was used in a 1:5,000 dilution. Purified MS59 was also run alongside on the gel, and is included for reference.

A number of transformed plants selected based on their high level expression of MS59 protein and S1 progeny plants will be tested in fungal infection assays.

EXAMPLE 20

Purification of MS59 Transproteins from Tobacco Transgenics

Transgenic tobacco plants were produced expressing MS59 constitutively. Levels of expression are determined using Western analysis. Extracts of the transgenic material are assayed for in vitro growth inhibitory activity against *Phytophthora infestans* and *Pythium ultimum*. Small scale total extracts were made from in vitro leaves of tobacco containing the pMOG1180 construct (mas-ocs-promotor-MS59) and of tobacco control lines. The extracts were made by grinding leaf material in 50 mM NaAc pH 5.2. The supernatant was dialysed against 50 mM MES pH 6.0 and tested for in vitro antifungal activity according to the methods described in the general experimental part. Some of the tobacco pMOG1180 lines showed high antifungal activity on *P.infestans* and *P.ultimum* compared to other lines or control lines.

EXAMPLE 21

Carbohydrate Oxidase Activity/Localization of MS59 in Transganic Tobacco

Equal amounts of partial purified soluble MS59 and soluble homologue fractions (Papaver, Eschscholzia, Arabidopsis-A11 and -B7) were tested for carbohydrate oxidase activity. Carbohydrate oxidase activity for MS59 was 0.011 ODu/min and for the homologues 0.0003–0.0012 ODu/min, a difference of a factor 10.

From the transgenic pMOG1180 tobacco lines of Example 20 that showed antifungal activity in vitro IF was isolated at a later stage and tested for carbohydrate oxidase activity. Also the material that was left after IF isolation (called "–IF") was tested. The same lines that showed antifungal activity have high carbohydrate oxidase activity. The activity is located in the IF.

EXAMPLE 22

Introduction of the Four Genes Construct Containing Chi-I, Glu-I, AP24 and MS59 Under Control of a Constitutive Plant Promoter, into Tomato, Potato, Carrot, *Brassica napus* and Arabidopsis Using Agrobacterium mediated transformation system binary construct pMOG1145 and pMOG1180 containing the genes encoding Chi-I, Glu-I, AP24 and MS59 or pMOG1146 containing the genes encoding Chi-I, Glu-I, bPR-1 and MS59 is introduced into different crop species including, tomato, potato, carrot, *Brassica napus* and Arabidopsis. S1 progeny plants are tested in fungal infection assays.

What is claimed is:

1. An isolated protein comprising
   (a) an amino acid sequence encoded by SEQ ID NO 15 which has antifungal activity; or a mutein of the amino acid sequence encoded by SEQ ID NO 15 wherein said mutein has antifungal activity; or a part of the amino acid sequence of SEQ ID NO 15 having antifungal activity; or
   (b) an amino acid sequence encoded by SEQ ID NO 19 which has antifungal activity; or a mutein of the amino acid sequence encoded by SEQ ID NO 19 wherein said mutein of the amino acid sequence encoded by SEQ ID NO 19 has antifungal activity; or a part of the amino acid sequence of SEQ ID NO 19 having antifungal activity; or
   (c) an amino acid sequence encoded by SEQ ID NO 57 which has antifungal activity; or a mutein of the amino acid sequence encoded by SEQ ID NO 57 wherein said mutein of the amino acid sequence encoded by SEQ ID NO 57 has antifungal activity; or a part of the amino acid sequence of SEQ ID NO 57 having antifungal activity; or
   (d) an amino acid sequence encoded by SEQ ID NO 70 which has antifungal activity; or a mutein of the amino acid sequence encoded by SEQ ID NO 70 wherein said mutein of the amino acid sequence encoded by SEQ ID NO 70 has antifungal activity; or a part of the amino acid sequence of SEQ ID NO 70 having antifungal activity; or
   (e) an amino acid sequence encoded by SEQ ID NO 72 which has antifungal activity; or a mutein of the amino acid sequence encoded by SEQ ID NO 72 wherein mutein of the amino acid sequence encoded by SEQ ID NO 72 has antifungal activity; or a part of the amino acid sequence of SEQ ID NO 72 having antifungal activity; or
   (f) an amino acid sequence encoded by SEQ ID NO. 74 which has antifungal activity; or a mutein of the amino acid sequence encoded by SEQ ID NO 74 wherein said mutein of the amino acid sequence encoded by SEQ ID NO 74 has antifungal activity; or a part of the amino acid sequence of SEQ ID NO 74 having antifungal activity, wherein the muteins in subparagraphs (a)–(f) differ from the respective amino acid sequences of which they are muteins only by the replacement, addition or deletion of one amino acid.

2. An isolated protein according to claim 1, wherein the protein naturally occurs in sunflower or lettuce.

3. An isolated protein according to claim 1, wherein the protein has anti-Oomycete activity or anti-Phytophthora activity or anti-Pythium activity or a combination thereof.

4. An anti-fungal composition comprising
   (a) the isolated protein of claim 1; and
   (b) a suitable carrier.

5. An isolated antifungal protein comprising the amino acid sequence encoded by the open reading frame of SEQ ID NO 15 or a part of said amino acid sequence having antifungal activity.

6. An isolated antifungal protein comprising the amino acid sequence encoded by the open reading frame represented by SEQ ID NO 19 or a part of said amino acid sequence having antifungal activity.

* * * * *